(12) United States Patent
Hada et al.

(10) Patent No.: US 8,808,959 B2
(45) Date of Patent: Aug. 19, 2014

(54) RESIST COMPOSITION, METHOD OF FORMING RESIST PATTERN, NOVEL COMPOUND, AND ACID GENERATOR

(75) Inventors: Hideo Hada, Kawasaki (JP); Yoshiyuki Utsumi, Kawasaki (JP); Takehiro Seshimo, Kawasaki (JP); Akiya Kawaue, Kawasaki (JP)

(73) Assignee: Tokyo Ohka Kogyo Co., Ltd., Kanagawa-ken (JP)

( * ) Notice: Subject to any disclaimer, the term of this patent is extended or adjusted under 35 U.S.C. 154(b) by 540 days.

(21) Appl. No.: 12/591,152

(22) Filed: Nov. 10, 2009

(65) Prior Publication Data

US 2010/0119974 A1    May 13, 2010

(30) Foreign Application Priority Data

Nov. 13, 2008 (JP) ............... P2008-291054
Nov. 13, 2008 (JP) ............... P2008-291055
Nov. 13, 2008 (JP) ............... P2008-291056

(51) Int. Cl.
*G03F 7/038* (2006.01)
*G03F 7/039* (2006.01)
*G03F 7/20* (2006.01)
*G03F 7/30* (2006.01)

(52) U.S. Cl.
USPC ........ 430/270.1; 430/311; 430/325; 430/326; 430/910; 430/921; 430/923; 430/925

(58) Field of Classification Search
None
See application file for complete search history.

(56) References Cited

U.S. PATENT DOCUMENTS

| | | | |
|---|---|---|---|
| 5,548,055 A | 8/1996 | Narang et al. | |
| 5,945,517 A | 8/1999 | Nitta et al. | |
| 6,153,733 A | 11/2000 | Yukawa et al. | |
| 6,395,450 B1 | 5/2002 | Park et al. | |
| 6,624,328 B1 | 9/2003 | Guerra | |
| 7,074,543 B2 | 7/2006 | Iwai et al. | |
| 7,396,960 B2 | 7/2008 | Iwabuchi et al. | |
| 7,618,765 B2 | 11/2009 | Nishi et al. | |
| 2002/0015906 A1 | 2/2002 | Lee et al. | |
| 2004/0110085 A1 | 6/2004 | Iwai et al. | |
| 2006/0166136 A1* | 7/2006 | Kanda | 430/270.1 |
| 2007/0219368 A1* | 9/2007 | Iwabuchi et al. | 544/5 |
| 2008/0081292 A1 | 4/2008 | Tsuchihashi et al. | |
| 2008/0187860 A1* | 8/2008 | Tsubaki et al. | 430/270.1 |
| 2008/0220371 A1 | 9/2008 | Kodama | |
| 2008/0248420 A1 | 10/2008 | Kanna | |
| 2008/0254386 A1 | 10/2008 | Nishi et al. | |
| 2009/0111047 A1* | 4/2009 | Yamashita | 430/270.1 |
| 2010/0119972 A1* | 5/2010 | Houlihan et al. | 430/281.1 |

FOREIGN PATENT DOCUMENTS

| | | |
|---|---|---|
| JP | 9-208554 | 8/1997 |
| JP | 11-035551 | 2/1999 |
| JP | 11-035552 | 2/1999 |
| JP | 11-035573 | 2/1999 |
| JP | 11-502543 | 3/1999 |
| JP | 11-322707 | 11/1999 |
| JP | 2001-019799 | 1/2001 |
| JP | 2002-053618 | 2/2002 |
| JP | 2003-241385 | 8/2003 |

(Continued)

OTHER PUBLICATIONS

Office Action issued Apr. 16, 2013 in Japanese Application No. 2008-291054.

(Continued)

*Primary Examiner* — Sin J. Lee
(74) *Attorney, Agent, or Firm* — Wenderoth, Lind & Ponack, L.L.P.

(57) ABSTRACT

A resist composition including a base component (A) which exhibits changed solubility in an alkali developing solution under action of acid and an acid-generator component (B) including a compound represented by (b1-1), a compound represented by (b1-1') and/or a compound represented by (b1-1") ($R^{1''}$-$R^{3''}$ represents an aryl group or an alkyl group, provided that at least one of $R^{1''}$-$R^{3''}$ represents a substituted aryl group being substituted with a group represented by (b1-1-0), and two of $R^{1''}$-$R^{3''}$ may be mutually bonded to form a ring with the sulfur atom; X represents a $C_3$-$C_{30}$ hydrocarbon group; $Q^1$ represents a carbonyl group-containing divalent linking group; $X^{10}$ represents a $C_1$-$C_{30}$ hydrocarbon group; $Q^3$ represents a single bond or a divalent linking group; $Y^{10}$ represents —C(=O)— or —$SO_2$—; $Y^{11}$ represents a $C_1$-$C_{10}$ alkyl group or a fluorinated alkyl group: $Q^2$ represents a single bond or an alkylene group; and W represents a $C_2$-$C_{10}$ alkylene group).

[Chemical Formula 1]

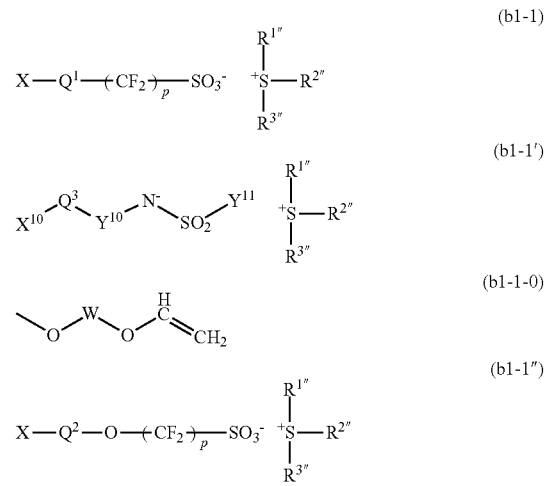

9 Claims, No Drawings

(56) References Cited

FOREIGN PATENT DOCUMENTS

| | | |
|---|---|---|
| JP | 2005-037888 | 2/2005 |
| JP | 2006-348382 | 12/2006 |
| JP | 2007-206639 | 8/2007 |
| JP | 2007-277219 | 10/2007 |
| JP | 2008-89790 | 4/2008 |
| JP | 2008-170535 | 7/2008 |
| JP | 2008-189601 | 8/2008 |
| JP | 2008-191413 | 8/2008 |
| JP | 2008-257198 | 10/2008 |
| JP | 2008-268921 | 11/2008 |
| WO | 2004/074242 | 9/2004 |
| WO | 2010/055406 | 5/2010 |

OTHER PUBLICATIONS

Office Action issued Apr. 16, 2013 in Japanese Application No. 2008-291055.

Office Action issued Apr. 16, 2013 in Japanese Application No. 2008-291056.

Notice of Allowance issued Jun. 3, 2014 in Japanese Application No. 2013-127033, with English language translation thereof.

* cited by examiner

RESIST COMPOSITION, METHOD OF FORMING RESIST PATTERN, NOVEL COMPOUND, AND ACID GENERATOR

TECHNICAL FIELD

The present invention relates to a resist composition, a method of forming a resist pattern using the same, a novel compound useful as an acid generator for a resist composition, and an acid generator.

Priority is claimed on Japanese Patent Application No. 2008-291054, filed Nov. 13, 2008, Japanese Patent Application No. 2008-291055, filed Nov. 13, 2008, and Japanese Patent Application No. 2008-291056, filed Nov. 13, 2008, the contents of which are incorporated herein by reference.

BACKGROUND ART

In lithography techniques, for example, a resist film composed of a resist material is formed on a substrate, and the resist film is subjected to selective exposure of radial rays such as light or electron beam through a mask having a predetermined pattern, followed by development, thereby forming a resist pattern having a predetermined shape on the resist film. A resist material in which the exposed portions become soluble in a developing solution is called a positive-type, and a resist material in which the exposed portions become insoluble in a developing solution is called a negative-type.

In recent years, in the production of semiconductor elements and liquid crystal display elements, advances in lithography techniques have lead to rapid progress in the field of pattern miniaturization.

Typically, these miniaturization techniques involve shortening the wavelength of the exposure light source. Conventionally, ultraviolet radiation typified by g-line and i-line radiation has been used, but nowadays KrF excimer lasers and ArF excimer lasers are starting to be introduced in mass production. Furthermore, research is also being conducted into lithography techniques that use an exposure light source having a wavelength shorter than these excimer lasers, such as $F_2$ excimer lasers, electron beam, extreme ultraviolet radiation (EUV), and X-ray.

Resist materials for use with these types of exposure light sources require lithography properties such as a high resolution capable of reproducing patterns of minute dimensions, and a high level of sensitivity to these types of exposure light sources. As a resist material which satisfies these conditions, a chemically amplified resist is used, which includes a base resin that exhibits a changed solubility in an alkali developing solution under action of acid and an acid generator that generates acid upon exposure. For example, a chemically amplified positive resist contains, as a base resin, a resin which exhibits increased solubility in an alkali developing solution under action of acid, and an acid generator. In the formation of a resist pattern, when acid is generated from the acid generator upon exposure, the exposed portions become soluble in an alkali developing solution.

Until recently, polyhydroxystyrene (PHS) or derivative resins thereof in which the hydroxyl groups are protected with acid-dissociable, dissolution-inhibiting groups (PHS-based resins), which exhibit high transparency to a KrF excimer laser (248 nm), have been used as the base resin component of chemically amplified resists. However, because PHS-based resins contain aromatic rings such as benzene rings, their transparency is inadequate for light with wavelengths shorter than 248 nm, such as light of 193 nm. Accordingly, chemically amplified resists that use a PHS-based resin as the base resin component suffer from low levels of resolution in processes that use light of 193 nm. As a result, resins that contain structural units derived from (meth)acrylate esters within the main chain (acrylic resins) are now widely used as base resins for resists that use ArF excimer laser lithography, as they exhibit excellent transparency in the vicinity of 193 nm. In the case of a positive resist, as the base resin, those which have a structural unit derived from (meth)acrylate ester including an aliphatic polycyclic group-containing, tertiary alkyl ester-type acid dissociable, dissolution inhibiting group, such as a structural unit derived from 2-alkyl-2-adamantyl(meth)acrylate are mainly used (for example, see Patent Document 1).

Here, the term "(meth)acrylate ester" is a generic term that includes either or both of the acrylate ester having a hydrogen atom bonded to the α-position and the methacrylate ester having a methyl group bonded to the α-position. The term "(meth)acrylate" is a generic term that includes either or both of the acrylate having a hydrogen atom bonded to the α-position and the methacrylate having a methyl group bonded to the α-position. The term "(meth)acrylic acid" is a generic term that includes either or both of acrylic acid having a hydrogen atom bonded to the α-position and methacrylic acid having a methyl group bonded to the α-position.

On the other hand, as acid generators usable in a chemically amplified resist, various types have been proposed including, for example, onium salt acid generators such as iodonium salts and sulfonium salts; oxime sulfonate acid generators; diazomethane acid generators; nitrobenzylsulfonate acid generators; iminosulfonate acid generators; and disulfone acid generators.

Currently, as acid generators, onium salt acid generators having an onium ion such as triphenylsulfonium as the cation moiety are used. As the anion moiety for onium salt acid generators, an alkylsulfonate ion or a fluorinated alkylsulfonate ion in which part or all of the hydrogen atoms within the aforementioned alkylsulfonate ion has been substituted with fluorine atoms is typically used (for example, see Patent Document 2).

[Patent Document 1] Japanese Unexamined Patent Application, First Publication No. 2003-241385 [Patent Document 2] Japanese Unexamined Patent Application, First Publication No. 2005-037888

SUMMARY OF THE INVENTION

Currently, among the aforementioned onium salt-based acid generators, onium salt-based acid generators having a perfluoroalkylsulfonic acid ion as the anion moiety are generally used.

However, in recent years, as miniaturization of resist patterns progress, further improvement in resist pattern shape and various lithography properties have been demanded for conventional resist compositions containing an onium salt-based acid generator having a perfluoroalkylsulfonic acid ion as the anion moiety.

Therefore, development of a novel compound which is more favorable as an acid generator for a resist composition has been demanded.

The present invention takes the above circumstances into consideration, with an object of providing a novel compound useful as an acid generator for a resist composition, an acid generator using the compound, a resist composition containing the acid generator, and a method of forming a resist pattern using the resist composition.

For solving the above-mentioned problems, the present invention employs the following aspects.

Specifically, a first aspect of the present invention is a resist composition including a base component (A) which exhibits changed solubility in an alkali developing solution under action of acid and an acid-generator component (B) which generates acid upon exposure, the acid-generator component (B) including at least one member selected from the group consisting of an acid generator (B1) including a compound represented by general formula (b1-1) shown below, an acid generator (B1') represented by general formula (b1-1') shown below and an acid generator (B1") represented by general formula (b1-1") shown below.

[Chemical Formula 1]

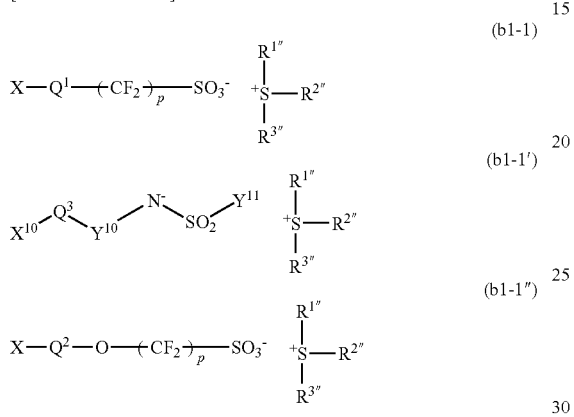

In the formulas, each of $R^{1''}$ to $R^{3''}$ independently represents an aryl group which may have a substituent or an alkyl group which may have a substituent, with the provision that at least one of $R^{1''}$ to $R^{3''}$ represents a substituted aryl group having part of the hydrogen atoms substituted with a group represented by general formula (b1-1-0) shown below, and two of $R^{1''}$ to $R^{3''}$ may be bonded to each other to form a ring with the sulfur atom; X represents a hydrocarbon group of 3 to 30 carbon atoms which may have a substituent; $Q^1$ represents a divalent linking group containing a carbonyl group; p represents an integer of 1 to 3; $X^{10}$ represents a hydrocarbon group of 1 to 30 carbon atoms which may have a substituent; $Q^3$ represents a single bond or a divalent linking group; $Y^{10}$ represents —C(=O)— or —SO$_2$—; $Y^{11}$ represents an alkyl group of 1 to 10 carbon atoms which may have a substituent or a fluorinated alkyl group which may have a substituent: and $Q^2$ represents a single bond or an alkylene group.

[Chemical Formula 2]

In formula (b1-1-0), W represents a linear or branched alkylene group of 2 to 10 carbon atoms.

A second aspect of the present invention is a method of forming a resist pattern, including forming a resist film on a substrate using a resist composition according to the first aspect, subjecting the resist film to exposure, and subjecting the resist film to alkali developing to form a resist pattern.

A third aspect of the present invention is a compound including at least one member selected from the group consisting of a compound (B1) represented by general formula (b1-1) shown below, a compound (B1') represented by general formula (b1-1') shown below and a compound (B1") represented by general formula (b1-1") shown below.

[Chemical Formula 3]

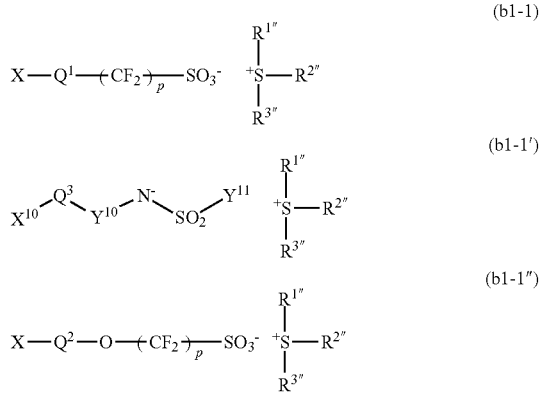

In the formulas, each of $R^{1''}$ to $R^{3''}$ independently represents an aryl group which may have a substituent or an alkyl group which may have a substituent, with the provision that at least one of $R^{1''}$ to $R^{3''}$ represents a substituted aryl group having part of the hydrogen atoms substituted with a group represented by general formula (b1-1-0) shown below, and two of $R^{1''}$ to $R^{3''}$ may be bonded to each other to form a ring with the sulfur atom; X represents a hydrocarbon group of 3 to 30 carbon atoms which may have a substituent; $Q^1$ represents a divalent linking group containing a carbonyl group; p represents an integer of 1 to 3; $X^{10}$ represents a hydrocarbon group of 1 to 30 carbon atoms which may have a substituent; $Q^3$ represents a single bond or a divalent linking group; $Y^{10}$ represents —C(=O)— or —SO$_2$—; $Y^{11}$ represents an alkyl group of 1 to 10 carbon atoms which may have a substituent or a fluorinated alkyl group which may have a substituent: and $Q^2$ represents a single bond or an alkylene group.

[Chemical Formula 4]

In formula (b1-1-0), W represents a linear or branched alkylene group of 2 to 10 carbon atoms.

A fourth aspect of the present invention is an acid generator including the compound of the third aspect.

In the present description and claims, an "alkyl group" includes linear, branched or cyclic, monovalent saturated hydrocarbon, unless otherwise specified.

The term "alkylene group" includes linear, branched or cyclic divalent saturated hydrocarbon, unless otherwise specified.

A "lower alkyl group" is an alkyl group of 1 to 5 carbon atoms.

A "halogenated alkyl group" is a group in which part or all of the hydrogen atoms of an alkyl group is substituted with halogen atoms. Examples of the halogen atom include a fluorine atom, a chlorine atom, a bromine atom and an iodine atom.

The term "structural unit" refers to a monomer unit that contributes to the formation of a polymeric compound (polymer, copolymer).

The term "exposure" is used as a general concept that includes irradiation with any form of radiation.

According to the present invention, there are provided a novel compound useful as an acid generator for a resist composition, an acid generator using the compound, a resist composition containing the acid generator, and a method of forming a resist pattern using the resist composition.

DETAILED DESCRIPTION OF THE INVENTION

<<Resist Composition>>

The resist composition according to the first aspect of the present invention includes a base component (A) which exhibits changed solubility in an alkali developing solution under action of acid (hereafter, referred to as "component (A)") and an acid-generator component (B) which generates acid upon exposure (hereafter, referred to as "component (B)").

With respect to a resist film formed using the resist composition, when a selective exposure is conducted during formation of a resist pattern, acid is generated from the component (B), and the generated acid acts on the component (A) to change the solubility of the component (A) in an alkali developing solution. As a result, the solubility of the exposed portions in an alkali developing solution is changed, whereas the solubility of the unexposed portions in an alkali developing solution remains unchanged. Therefore, the exposed portions are dissolved and removed by alkali developing in the case of a positive resist composition, whereas unexposed portions are dissolved and removed in the case of a negative resist composition, and hence, a resist pattern can be formed.

The resist composition of the present invention may be either a negative resist composition or a positive resist composition.

<Component (A)>

As the component (A), an organic compound typically used as a base component for a chemically amplified resist composition can be used alone, or two or more of such organic compounds can be mixed together.

Here, the term "base component" refers to an organic compound capable of forming a film, and is preferably an organic compound having a molecular weight of 500 or more. When the organic compound has a molecular weight of 500 or more, the film-forming ability is improved, and a resist pattern of nano level can be easily formed.

The organic compounds having a molecular weight of 500 or more are broadly classified into low molecular weight organic compounds having a molecular weight of 500 to less than 2,000 (hereafter, referred to as "low molecular weight materials") and high molecular weight resins having a molecular weight of 2,000 or more (namely, "polymeric materials"). Generally, as the aforementioned low molecular weight compound, a non-polymer is used. With respect to the aforementioned resin (polymer or copolymer), the molecular weight is the polystyrene equivalent value determined by gel permeation chromatography (GPC). Hereafter, a "resin" refers to a resin having a molecular weight of 2,000 or more.

As the component (A), a resin which exhibits changed solubility in an alkali developing solution under action of acid may be used. Alternatively, as the component (A), a low molecular weight material which exhibits changed solubility in an alkali developing solution under action of acid may be used.

When the resist composition of the present invention is a negative resist composition, for example, as the component (A), a base component that is soluble in an alkali developing solution is used, and a cross-linking agent is blended in the negative resist composition.

In the negative resist composition, when acid is generated from the component (B) upon exposure, the action of the generated acid causes cross-linking between the base component and the cross-linking agent, and the cross-linked portion becomes insoluble in an alkali developing solution. Therefore, in the formation of a resist pattern, by conducting selective exposure of a resist film formed by applying the negative resist composition onto a substrate, the exposed portions become insoluble in an alkali developing solution, whereas the unexposed portions remain soluble in an alkali developing solution, and hence, a resist pattern can be formed by alkali developing.

Generally, as the component (A) for a negative resist composition, a resin that is soluble in an alkali developing solution (hereafter, referred to as "alkali-soluble resin") is used.

As the alkali-soluble resin, it is preferable to use a resin having structural units derived from at least one of an α-(hydroxyalkyl)acrylic acid and a lower alkyl ester of an α-(hydroxyalkyl)acrylic acid, as such resins enable the formation of a satisfactory resist pattern with minimal swelling. Here, the term "α-(hydroxyalkyl)acrylic acid" refers to one or both of acrylic acid in which a hydrogen atom is bonded to the carbon atom on the α-position having the carboxyl group bonded thereto, and α-hydroxyalkylacrylic acid in which a hydroxyalkyl group (preferably a hydroxyalkyl group of 1 to 5 carbon atoms) is bonded to the carbon atom on the α-position.

As the cross-linking agent, typically, an amino-based cross-linking agent such as a glycoluril having a methylol group or alkoxymethyl group is preferable, as it enables formation of a resist pattern with minimal swelling. The amount of the cross-linker added is preferably within a range from 1 to 50 parts by weight, relative to 100 parts by weight of the alkali-soluble resin.

When the resist composition of the present invention is a positive resist composition, as the component (A), a base component that exhibits increased solubility in an alkali developing solution under the action of acid is used. More specifically, the component (A) is substantially insoluble in an alkali developing solution prior to exposure, but when acid is generated from the component (B) upon exposure, the action of this acid causes an increase in the solubility of the base component in an alkali developing solution. Therefore, in the formation of a resist pattern, by conducting selective exposure of a resist film formed by applying the positive resist composition onto a substrate, the exposed portions changes from an insoluble state to a soluble state in an alkali developing solution, whereas the unexposed portions remain insoluble in an alkali developing solution, and hence, a resist pattern can be formed by alkali developing.

In the resist composition of the present invention, the component (A) is preferably a base component that exhibits increased solubility in an alkali developing solution under the action of acid. That is, the resist composition of the present invention is preferably a positive resist composition.

The component (A) may be a resin component (A1) that exhibits increased solubility in an alkali developing solution under the action of acid (hereafter, frequently referred to as "component (A1)"), a low molecular weight compound (A2) that exhibits increased solubility in an alkali developing solution under the action of acid (hereafter, frequently referred to as "component (A2)"), or a mixture thereof. Of these, the component (A) preferably includes the component (A1).

[Component (A1)]

As the component (A1), a resin component (base resin) typically used as a base component for a chemically amplified resist composition can be used alone, or two or more of such resin components can be mixed together.

In the present embodiment, it is preferable that the component (A1) include a structural unit derived from an acrylate ester.

In the present descriptions and claims, the term "structural unit derived from an acrylate ester" refers to a structural unit which is formed by the cleavage of the ethylenic double bond of an acrylate ester.

The term "acrylate ester" is a generic term that includes acrylate esters having a hydrogen atom bonded to the carbon atom on the α-position, and acrylate esters having a substituent (an atom other than a hydrogen atom or a group) bonded to the carbon atom on the α-position. As the substituent, a lower alkyl group or a halogenated lower alkyl group can be used.

With respect to the "structural unit derived from an acrylate ester", the "α-position (the carbon atom on the α-position)" refers to the carbon atom having the carbonyl group bonded thereto, unless specified otherwise.

With respect to the acrylate ester, specific examples of the lower alkyl group for the substituent at the α-position include linear or branched alkyl groups such as a methyl group, an ethyl group, a propyl group, an isopropyl group, an n-butyl group, an isobutyl group, a tert-butyl group, a pentyl group, an isopentyl group, and a neopentyl group.

Further, specific examples of the halogenated lower alkyl group include groups in which part or all of the hydrogen atoms of the aforementioned "lower alkyl group for the substituent at the α-position" have been substituted with halogen atoms. Examples of halogen atoms include fluorine atoms, chlorine atoms, bromine atoms and iodine atoms, and fluorine atoms are particularly desirable.

In the present invention, it is preferable that a hydrogen atom, a lower alkyl group or a halogenated lower alkyl group is bonded to the α-position of the acrylate ester, a hydrogen atom, a lower alkyl group or a fluorinated lower alkyl group is more preferable, and in terms of industrial availability, a hydrogen atom or a methyl group is the most desirable.

It is particularly desirable that the component (A1) have a structural unit (a1) derived from an acrylate ester containing an acid dissociable, dissolution inhibiting group.

Further, it is preferable that the component (A1) have a structural unit (a2) derived from an acrylate ester containing a lactone-containing cyclic group, as well as the structural unit (a1).

Furthermore, it is preferable that the component (A1) have a structural unit (a3) derived from an acrylate ester containing a polar group-containing aliphatic hydrocarbon group, as well as the structural unit (a1), or the structural unit (a1) and the structural unit (a2).

—Structural Unit (a1)

As the acid dissociable, dissolution inhibiting group in the structural unit (a1), any of the groups that have been proposed as acid dissociable, dissolution inhibiting groups for the base resins of chemically amplified resists can be used, provided the group has an alkali dissolution-inhibiting effect that renders the entire component (A1) insoluble in an alkali developing solution prior to dissociation, and then following dissociation by action of acid, increases the solubility of the entire component (A1) in the alkali developing solution. Generally, groups that form either a cyclic or chain-like tertiary alkyl ester with the carboxyl group of the (meth)acrylic acid, and acetal-type acid dissociable, dissolution inhibiting groups such as alkoxyalkyl groups are widely known.

Here, a tertiary alkyl ester describes a structure in which an ester is formed by substituting the hydrogen atom of a carboxyl group with a chain-like or cyclic tertiary alkyl group, and a tertiary carbon atom within the chain-like or cyclic tertiary alkyl group is bonded to the oxygen atom at the terminal of the carbonyloxy group (—C(O)—O—). In this tertiary alkyl ester, the action of acid causes cleavage of the bond between the oxygen atom and the tertiary carbon atom.

The chain-like or cyclic alkyl group may have a substituent.

Hereafter, for the sake of simplicity, groups that exhibit acid dissociability as a result of the formation of a tertiary alkyl ester with a carboxyl group are referred to as "tertiary alkyl ester-type acid dissociable, dissolution inhibiting groups".

Examples of tertiary alkyl ester-type acid dissociable, dissolution inhibiting groups include aliphatic branched, acid dissociable, dissolution inhibiting groups and aliphatic cyclic group-containing acid dissociable, dissolution inhibiting groups.

The term "aliphatic branched" refers to a branched structure having no aromaticity.

The "aliphatic branched, acid dissociable, dissolution inhibiting group" is not limited to be constituted of only carbon atoms and hydrogen atoms (not limited to hydrocarbon groups), but is preferably a hydrocarbon group. Further, the "hydrocarbon group" may be either saturated or unsaturated, but is preferably saturated.

Examples of aliphatic branched, acid dissociable, dissolution inhibiting groups include tertiary alkyl groups of 4 to 8 carbon atoms, and specific examples include a tert-butyl group, tert-pentyl group and tert-heptyl group.

The term "aliphatic cyclic group" refers to a monocyclic group or polycyclic group that has no aromaticity.

The "aliphatic cyclic group" within the structural unit (a1) may or may not have a substituent. Examples of substituents include lower alkyl groups of 1 to 5 carbon atoms, lower aloxy groups of 1 to 5 carbon atoms, fluorine atom, fluorinated lower alkyl groups of 1 to 5 carbon atoms, and oxygen atom (=O).

The basic ring of the "aliphatic cyclic group" exclusive of substituents is not limited to be constituted from only carbon and hydrogen (not limited to hydrocarbon groups), but is preferably a hydrocarbon group. Further, the "hydrocarbon group" may be either saturated or unsaturated, but is preferably saturated. Furthermore, the "aliphatic cyclic group" is preferably a polycyclic group.

As such aliphatic cyclic groups, groups in which one or more hydrogen atoms have been removed from a monocycloalkane or a polycycloalkane such as a bicycloalkane, tricycloalkane or tetracycloalkane which may or may not be substituted with a lower alkyl group, a fluorine atom or a fluorinated lower alkyl group, may be used. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane.

As the aliphatic cyclic group-containing acid dissociable, dissolution inhibiting group, for example, a group which has a tertiary carbon atom on the ring structure of the cycloalkyl group can be used. Specific examples include 2-methyl-2-adamantyl group and a 2-ethyl-2-adamantyl group. Further, groups having an aliphatic cyclic group such as an adamantyl group, cyclohexyl group, cyclopentyl group, norbornyl group, tricyclodecanyl group or tetracyclododecanyl group, and a branched alkylene group having a tertiary carbon atom bonded thereto, as the groups bonded to the oxygen atom of the carbonyl group (—C(O)—O—) within the structural units represented by general formulas (a1"-1) to (a1"-6) shown below, can be used.

[Chemical Formula 5]

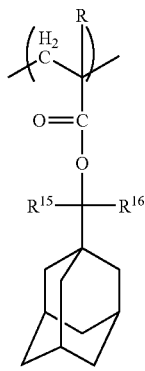

(a1"-1)

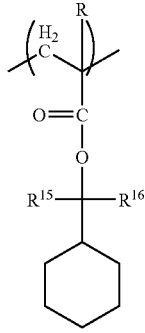

(a1"-2)

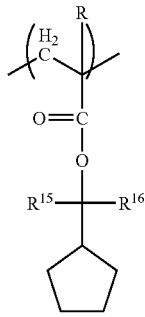

(a1"-3)

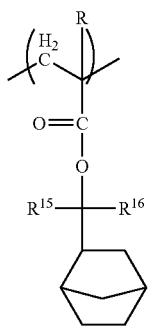

(a1"-4)

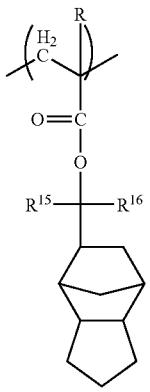

(a1"-5)

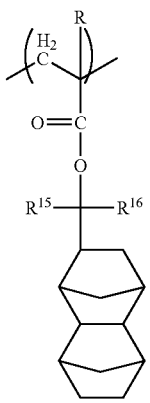

(a1"-6)

In the formulas, R represents a hydrogen atom, a lower alkyl group or a halogenated lower alkyl group; and $R^{15}$ and $R^{16}$ each independently represent an alkyl group (which may be linear or branched, and preferably has 1 to 5 carbon atoms).

In general formulas (a1"-1) to (a1"-6) above, the lower alkyl group or halogenated lower alkyl group for R are the same as the lower alkyl group or halogenated lower alkyl group which can be bonded to the α-position of the aforementioned acrylate ester.

An "acetal-type acid dissociable, dissolution inhibiting group" generally substitutes a hydrogen atom at the terminal of an alkali-soluble group such as a carboxy group or hydroxyl group, so as to be bonded with an oxygen atom. When acid is generated upon exposure, the generated acid acts to break the bond between the acetal-type acid dissociable, dissolution inhibiting group and the oxygen atom to which the acetal-type, acid dissociable, dissolution inhibiting group is bonded.

Examples of acetal-type acid dissociable, dissolution inhibiting groups include groups represented by general formula (p1) shown below.

[Chemical Formula 6]

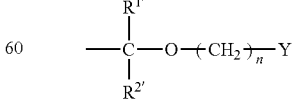

(p1)

In the formula, $R^{1'}$ and $R^{2'}$ each independently represent a hydrogen atom or a lower alkyl group; n represents an integer of 0 to 3; and Y represents a lower alkyl group or an aliphatic cyclic group.

In general formula (p1) above, n is preferably an integer of 0 to 2, more preferably 0 or 1, and most preferably 0.

As the lower alkyl group for $R^{1'}$ and $R^{2'}$, the same lower alkyl groups as those described above for R can be used, although a methyl group or ethyl group is preferable, and a methyl group is particularly desirable.

In the present invention, it is preferable that at least one of $R^{1'}$ and $R^{2'}$ be a hydrogen atom. That is, it is preferable that the acid dissociable, dissolution inhibiting group (p1) is a group represented by general formula (p1-1) shown below.

[Chemical Formula 7]

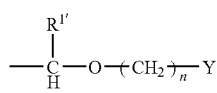

(p1-1)

In the formula, $R^{1'}$, n and Y are the same as defined above.

As the lower alkyl group for Y, the same as the lower alkyl groups for R above can be used.

As the aliphatic cyclic group for Y, any of the aliphatic monocyclic/polycyclic groups which have been proposed for conventional ArF resists and the like can be appropriately selected for use. For example, the same groups described above in connection with the "aliphatic cyclic group" can be used.

Further, as the acetal-type, acid dissociable, dissolution inhibiting group, groups represented by general formula (p2) shown below can also be used.

[Chemical Formula 8]

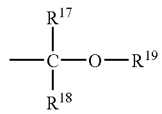

(p2)

In the formula, each of $R^{17}$ and $R^{18}$ independently represents a linear or branched alkyl group or a hydrogen atom; and $R^{19}$ represents a linear, branched or cyclic alkyl group; or $R^{17}$ and $R^{19}$ each independently represents a linear or branched alkylene group, and the terminal of $R^{17}$ is bonded to the terminal of $R^{19}$ to form a ring.

The alkyl group for $R^{17}$ and $R^{18}$ preferably has 1 to 15 carbon atoms, and may be either linear or branched. As the alkyl group, an ethyl group or a methyl group is preferable, and a methyl group is most preferable.

It is particularly desirable that either one of $R^{17}$ and $R^{18}$ be a hydrogen atom, and the other be a methyl group.

$R^{19}$ represents a linear, branched or cyclic alkyl group which preferably has 1 to 15 carbon atoms, and may be any of linear, branched or cyclic.

When $R^{19}$ represents a linear or branched alkyl group, it is preferably an alkyl group of 1 to 5 carbon atoms, more preferably an ethyl group or methyl group, and most preferably an ethyl group.

When $R^{19}$ represents a cycloalkyl group, it preferably has 4 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Examples of such groups include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane. Among these, a group in which one or more hydrogen atoms have been removed from adamantane is preferable.

In general formula (p2) above, $R^{17}$ and $R^{19}$ may each independently represent a linear or branched alkylene group (preferably an alkylene group of 1 to 5 carbon atoms), and the terminal of $R^{19}$ may be bonded to the terminal of $R^{17}$.

In such a case, a cyclic group is formed by $R^{17}$, $R^{19}$, the oxygen atom having $R^{19}$ bonded thereto, and the carbon atom having the oxygen atom and $R^{17}$ bonded thereto. Such a cyclic group is preferably a 4 to 7-membered ring, and more preferably a 4 to 6-membered ring. Specific examples of the cyclic group include tetrahydropyranyl group and tetrahydrofuranyl group.

As the structural unit (a1), it is preferable to use at least one member selected from the group consisting of structural units represented by formula (a1-0-1) shown below and structural units represented by formula (a1-0-2) shown below.

[Chemical Formula 9]

(a1-0-1)

In the formula, R represents a hydrogen atom, a lower alkyl group or a halogenated lower alkyl group; and $X^1$ represents an acid dissociable, dissolution inhibiting group.

[Chemical Formula 10]

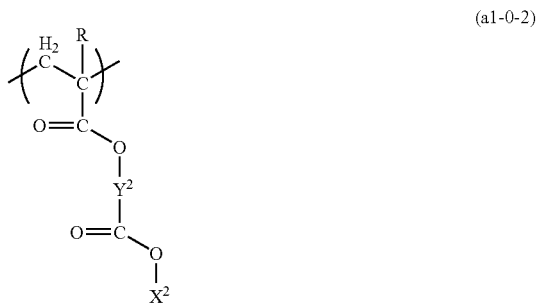

(a1-0-2)

In the formula, R represents a hydrogen atom, a lower alkyl group or a halogenated lower alkyl group; $X^2$ represents an acid dissociable, dissolution inhibiting group; and $Y^2$ represents a divalent linking group.

In general formula (a1-0-1) shown above, lower alkyl group and halogenated lower alkyl group for R are the same as the lower alkyl group and halogenated lower alkyl group which can be bonded to the α-position of the aforementioned acrylate ester.

$X^1$ is not particularly limited as long as it is an acid dissociable, dissolution inhibiting group. Examples thereof include the aforementioned tertiary alkyl ester-type acid dissociable, dissolution inhibiting groups and acetal-type acid dissociable, dissolution inhibiting groups, and tertiary alkyl ester-type acid dissociable, dissolution inhibiting groups are preferable.

In general formula (a1-0-2), R is the same as defined above.

$X^2$ is the same as defined for $X^1$ in general formula (a1-0-1).

As the divalent linking group for $Y^2$, an alkylene group, a divalent aliphatic cyclic group or a divalent linking group containing a hetero atom can be mentioned.

As the aliphatic cyclic group, the same as those used above in connection with the explanation of "aliphatic cyclic group" can be used, except that two hydrogen atoms have been removed therefrom.

When $Y^2$ represents an alkylene group, it preferably has 1 to 10 carbon atoms, more preferably 1 to 6, still more preferably 1 to 4, and most preferably 1 to 3.

When $Y^2$ represents a divalent aliphatic cyclic group, it is particularly desirable that the divalent aliphatic cyclic group be a group in which two or more hydrogen atoms have been removed from cyclopentane, cyclohexane, norbornane, isobornane, adamantane, tricyclodecane or tetracyclododecane.

When $Y^2$ represents a divalent linking group containing a hetero atom, examples thereof include —O—, —C(=O)—O—, —C(=O)—, —O—C(=O)—, —C(=O)—NH—, —NH— (H may be substituted with a substituent such as an alkyl group or an acyl group), —S—, —S(=O)$_2$—, —S(=O)$_2$—O—, and "—$Y^a$—O—$Y^b$—" (wherein O is an oxygen atom, and each of $Y^a$ and $Y^b$ independently represents a divalent hydrocarbon group which may have a substituent).

When $Y^2$ represents a divalent linking group —NH— and the H in the formula is replaced with a substituent such as an alkyl group or an acyl group, the substituent preferably has 1 to 10 carbon atoms, more preferably 1 to 8 carbon atoms, and most preferably 1 to 5 carbon atoms.

When $Y^2$ represents "$Y^a$—O—$Y^b$", each of $Y^a$ and $Y^b$ independently represents a divalent hydrocarbon group which may have a substituent.

A hydrocarbon "has a substituent" means that part or all of the hydrogen atoms within the hydrocarbon group is substituted with groups or atoms other than hydrogen atom.

The hydrocarbon group for $Y^a$ may be either an aliphatic hydrocarbon group, or an aromatic hydrocarbon group. An "aliphatic hydrocarbon group" refers to a hydrocarbon group that has no aromaticity.

The aliphatic hydrocarbon group for $Y^a$ may be either saturated or unsaturated. In general, the aliphatic hydrocarbon group is preferably saturated.

As specific examples of the aliphatic hydrocarbon group for $Y^a$, a linear or branched aliphatic hydrocarbon group, and an aliphatic hydrocarbon group having a ring in the structure thereof can be given.

The linear or branched aliphatic hydrocarbon group preferably has 1 to 10 carbon atoms, more preferably 1 to 8, still more preferably 2 to 5, and most preferably 2.

As a linear aliphatic hydrocarbon group, a linear alkylene group is preferable, and specific examples include a methylene group, an ethylene group [—(CH$_2$)$_2$—], a trimethylene group [—(CH$_2$)$_3$—], a tetramethylene group [—(CH$_2$)$_4$—] and a pentamethylene group [—(CH$_2$)$_5$—].

As a branched aliphatic hydrocarbon group, a branched alkylene group is preferable, and specific examples include alkylmethylene groups such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)—, and —C(CH$_2$CH$_3$)$_2$—; alkylethylene groups such as —CH(CH$_3$)CH$_2$—, —CH(CH$_3$)CH(CH$_3$)—, —C(CH$_3$)$_2$CH$_2$—, —CH(CH$_2$CH$_3$)CH$_2$—, and —CH(CH$_2$CH$_3$)CH$_2$—; alkyltrimethylene groups such as —CH(CH$_3$)CH$_2$CH$_2$—, and —CH$_2$CH(CH$_3$)CH$_2$—; and alkyltetramethylene groups such as —CH(CH$_3$)CH$_2$CH$_2$CH$_2$—, and —CH$_2$CH(CH$_3$)CH$_2$CH$_2$—. As the alkyl group within the alkylalkylene group, a linear alkyl group of 1 to 5 carbon atoms is preferable.

The linear or branched aliphatic hydrocarbon group (chain-like aliphatic hydrocarbon group) may or may not have a substituent. Examples of substituents include a fluorine atom, a fluorinated lower alkyl group of 1 to 5 carbon atoms, and an oxygen atom (=O).

As examples of the hydrocarbon group containing a ring, a cyclic aliphatic hydrocarbon group (a group in which two hydrogen atoms have been removed from an aliphatic hydrocarbon ring), and a group in which the cyclic aliphatic hydrocarbon group is bonded to the terminal of the aforementioned chain-like aliphatic hydrocarbon group or interposed within the aforementioned chain-like aliphatic hydrocarbon group, can be given.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic group, a group in which two hydrogen atoms have been removed from a monocycloalkane of 3 to 6 carbon atoms is preferable. Examples of the monocycloalkane include cyclopentane and cyclohexane.

As the polycyclic group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

The cyclic aliphatic hydrocarbon group may or may not have a substituent. Examples of substituents include a lower alkyl group of 1 to 5 carbon atoms, a fluorine atom, a fluorinated lower alkyl group of 1 to 5 carbon atoms, and an oxygen atom (=O).

As $Y^a$, a linear aliphatic hydrocarbon group is preferable, more preferably a linear alkylene group, still more preferably a linear alkylene group of 2 to 5 carbon atoms, and most preferably an ethylene group.

As the hydrocarbon group for $Y^b$, the same divalent hydrocarbon groups as those described above for $Y^a$ can be mentioned.

As $Y^b$, a linear or branched aliphatic hydrocarbon group is preferable, and a methylene group or an alkylmethylene group is particularly desirable.

The alkyl group within the alkyl methylene group is preferably a linear alkyl group of 1 to 5 carbon atoms, more preferably a linear alkyl group of 1 to 3 carbon atoms, and most preferably a methyl group.

Specific examples of the structural unit (a1) include structural units represented by general formulas (a1-1) to (a1-4) shown below.

[Chemical Formula 11]

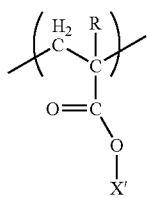
(a1-1)

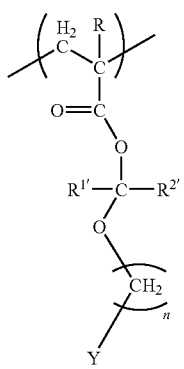
(a1-2)

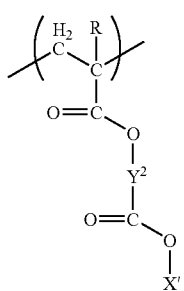
(a1-3)

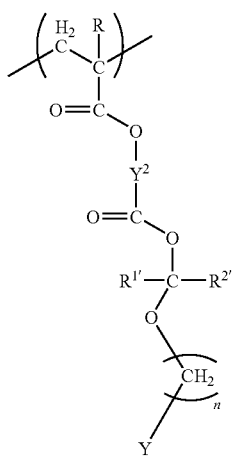
(a1-4)

In the formulas, X' represents a tertiary alkyl ester-type acid dissociable, dissolution inhibiting group; Y represents a lower alkyl group of 1 to 5 carbon atoms or an aliphatic cyclic group; n represents an integer of 0 to 3; $Y^2$ represents a divalent linking group; R is the same as defined above; and each of $R^{1\prime}$ and $R^{2\prime}$ independently represents a hydrogen atom or a lower alkyl group of 1 to 5 carbon atoms.

Examples of the tertiary alkyl ester-type acid dissociable, dissolution inhibiting group for X' include the same tertiary alkyl ester-type acid dissociable, dissolution inhibiting groups as those described above for $X^1$.

As $R^{1\prime}$, $R^{2\prime}$, n and Y are respectively the same as defined for $R^{1\prime}$, $R^{2\prime}$, n and Y in general formula (p1) described above in connection with the "acetal-type acid dissociable, dissolution inhibiting group".

As examples of $Y^2$, the same groups as those described above for $Y^2$ in general formula (a1-0-2) can be given.

Specific examples of structural units represented by general formula (a1-1) to (a1-4) are shown below.

In the formulas shown below, $R^\alpha$ represents a hydrogen atom, a methyl group or a trifluoromethyl group.

[Chemical Formula 12]

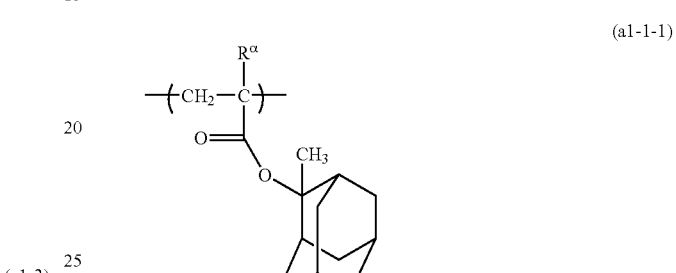
(a1-1-1)

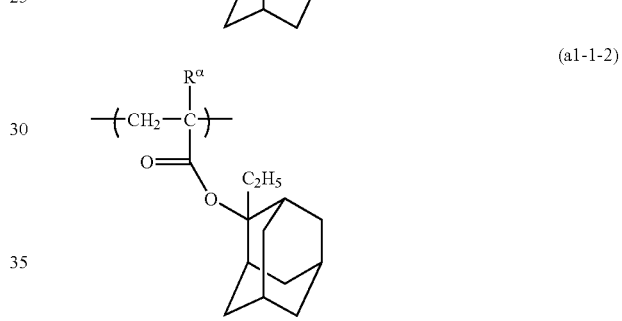
(a1-1-2)

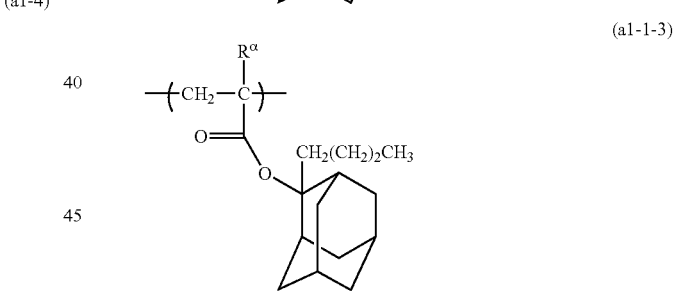
(a1-1-3)

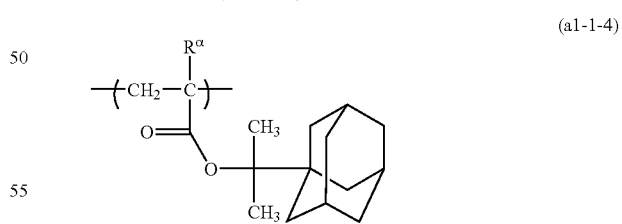
(a1-1-4)

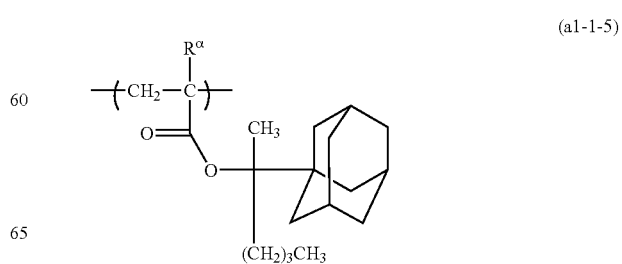
(a1-1-5)

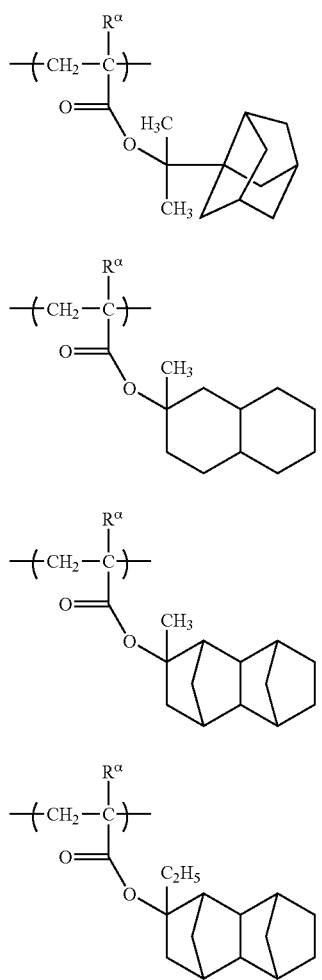
(a1-1-6)
(a1-1-7)
(a1-1-8)
(a1-1-9)
[Chemical Formula 13]
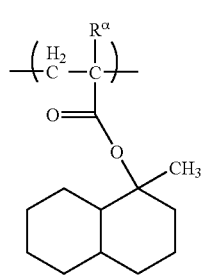
(a1-1-10)
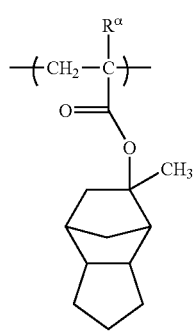
(a1-1-11)
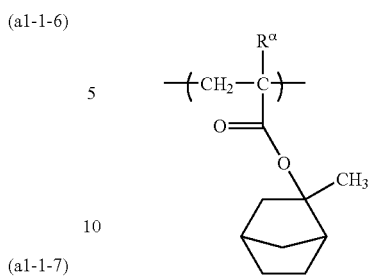
(a1-1-12)
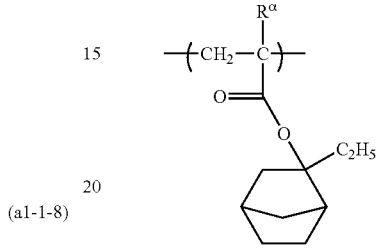
(a1-1-13)
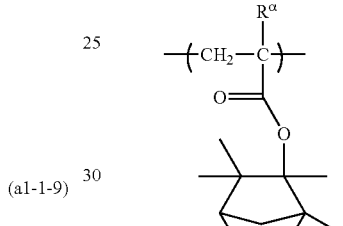
(a1-1-14)
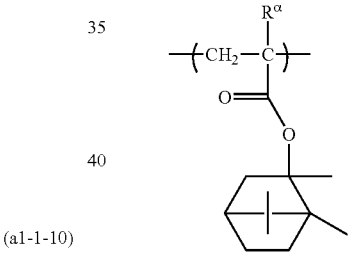
(a1-1-15)
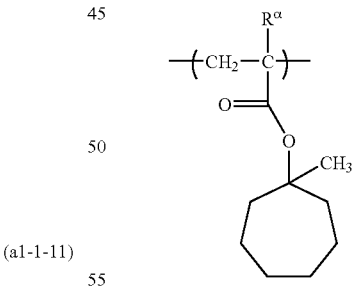
(a1-1-16)
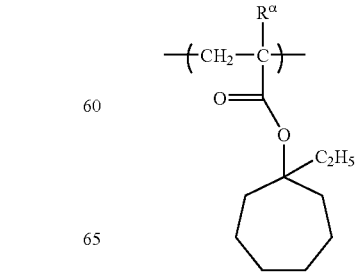
(a1-1-17)

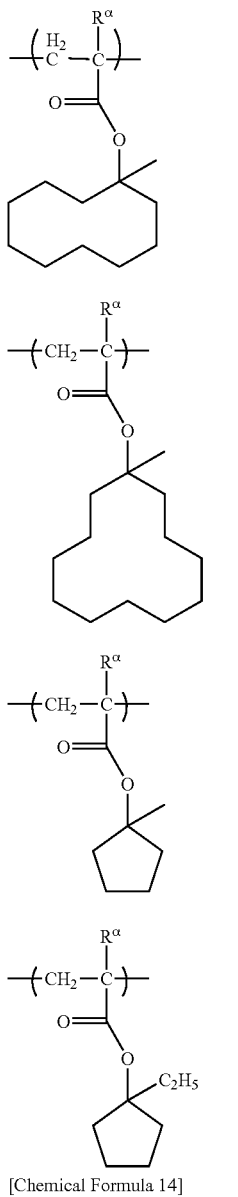
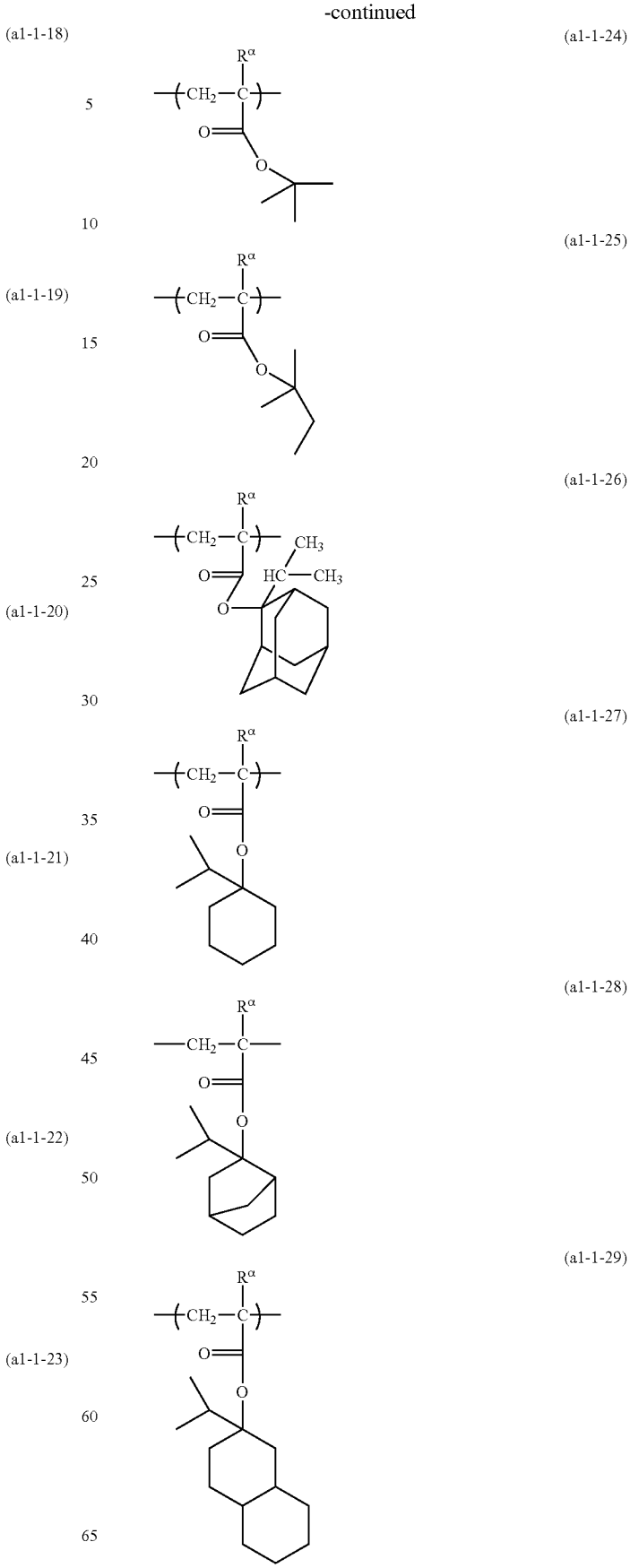

-continued
(a1-1-30)
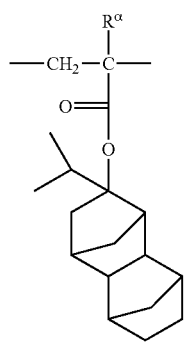
(a1-1-31)
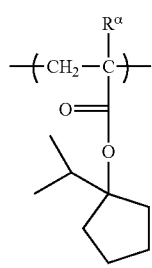
(a1-1-32)
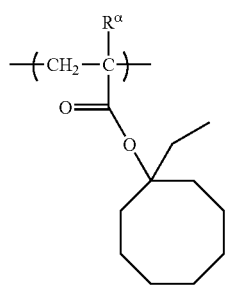
[Chemical Formula 15]
(a1-2-1)
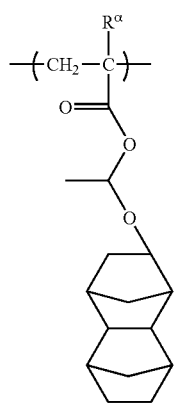
-continued
(a1-2-2)
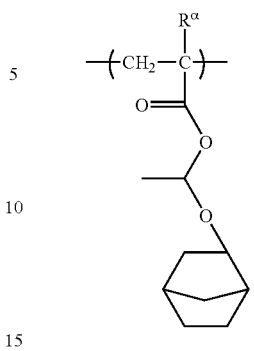
(a1-2-3)
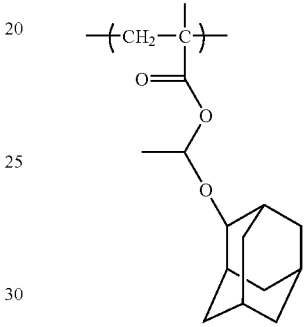
(a1-2-4)
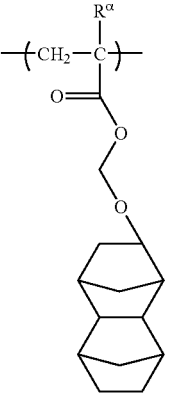
(a1-2-5)
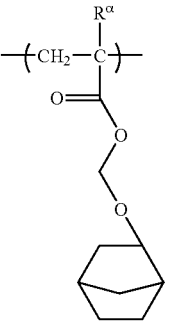

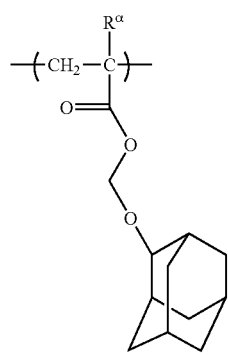
(a1-2-6)
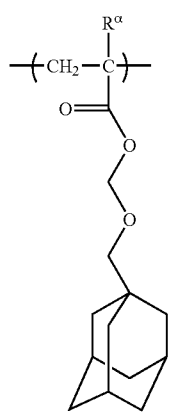
(a1-2-7)
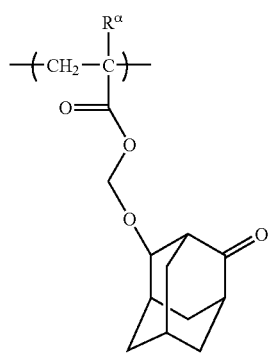
(a1-2-8)
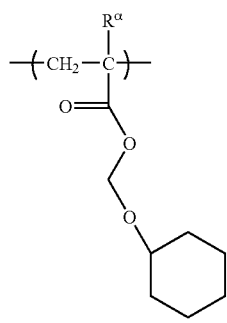
(a1-2-9)
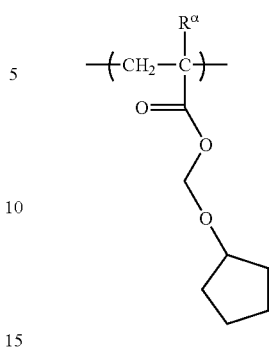
(a1-2-10)
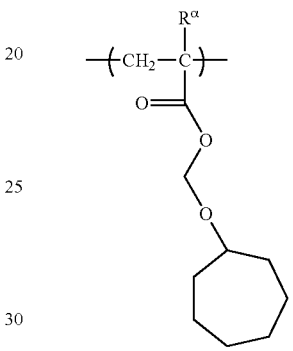
(a1-2-11)
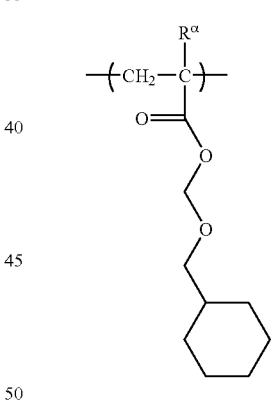
(a1-2-12)
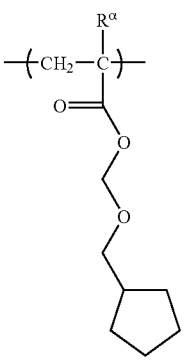
(a1-2-13)

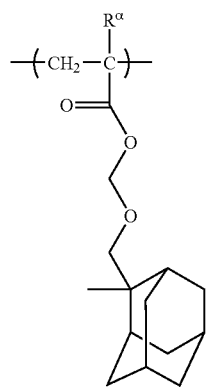
(a1-2-14)
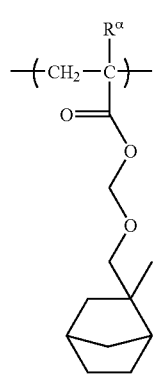
(a1-2-15)
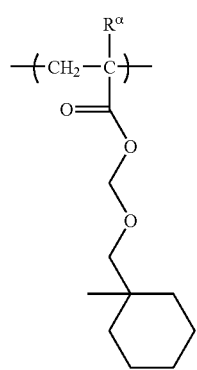
(a1-2-16)
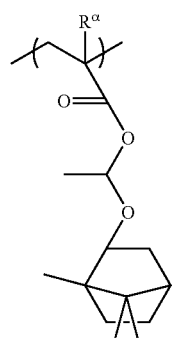
(a1-2-17)
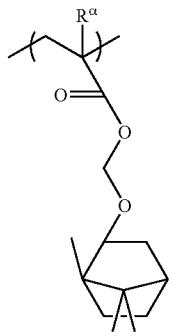
(a1-2-18)
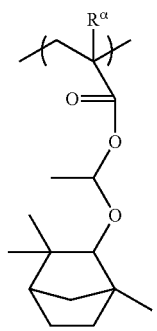
(a1-2-19)
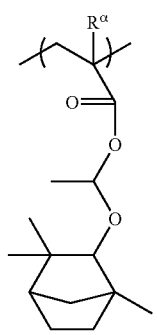
(a1-2-20)
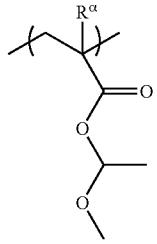
(a1-2-21)
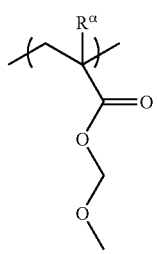
(a1-2-22)

(a1-2-23)
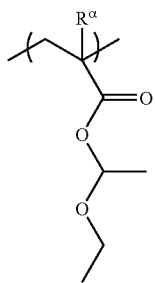
(a1-2-24)
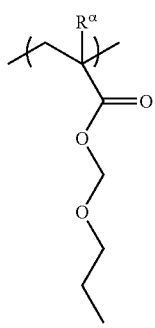
[Chemical Formula 16]
(a1-3-1)
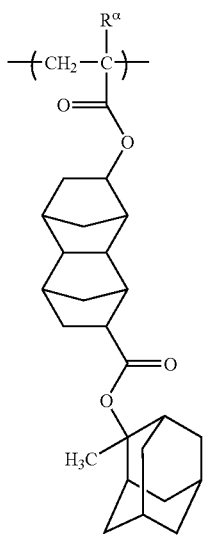
(a1-3-2)
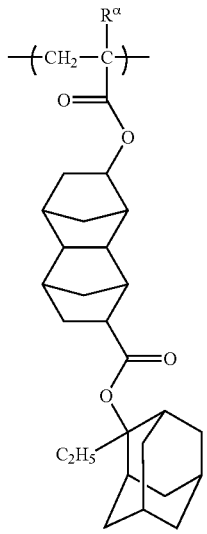
(a1-3-3)
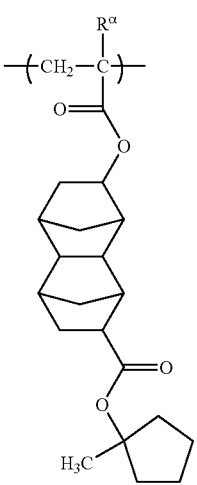
(a1-3-4)
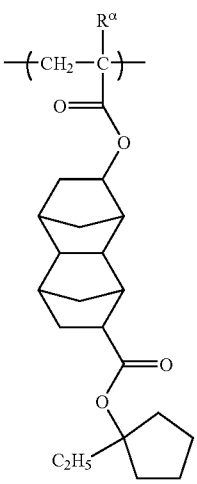

(a1-3-5)
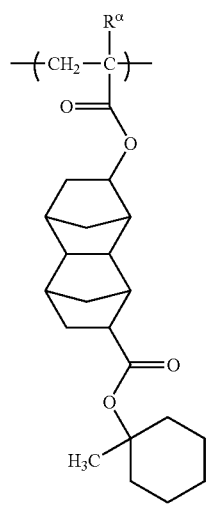
(a1-3-8)
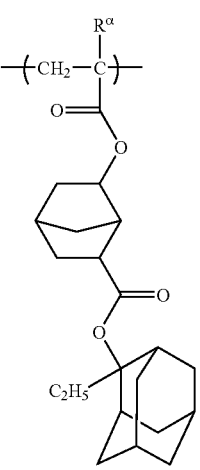
(a1-3-6)
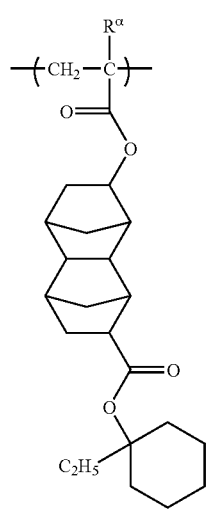
(a1-3-9)
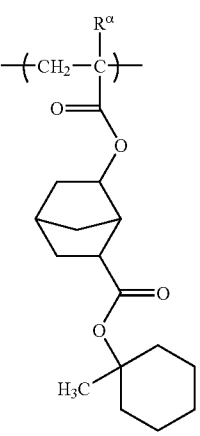
(a1-3-7)
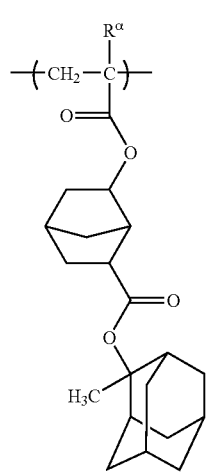
(a1-3-10)
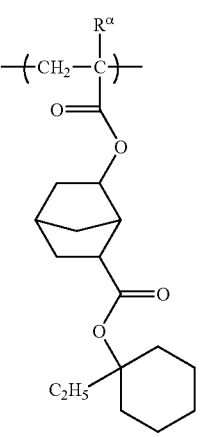

-continued
(a1-3-11) 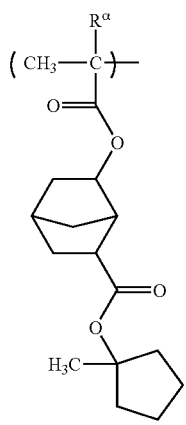
(a1-3-12) 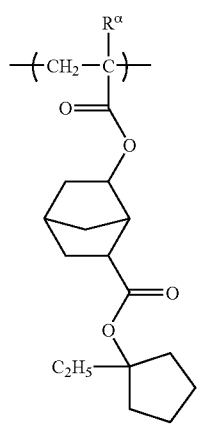
(a1-3-13) 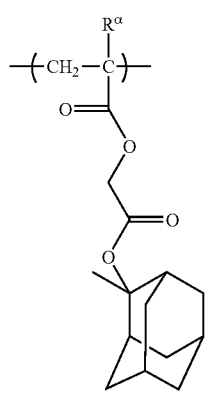
(a1-3-14) 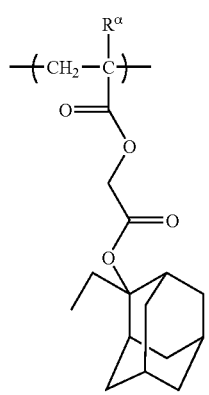
-continued
(a1-3-15) 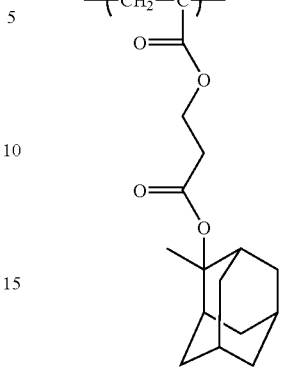
(a1-3-16) 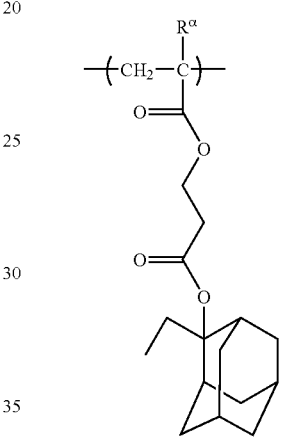
(a1-3-17) 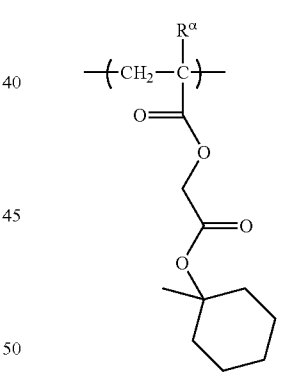
(a1-3-18) 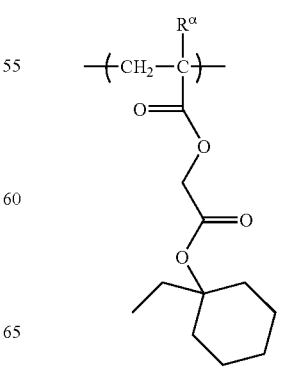

[Chemical Formula 17]
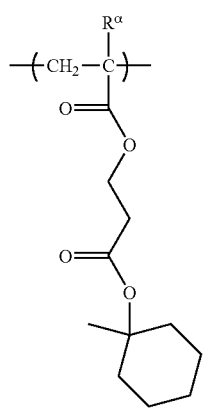 (a1-3-19)
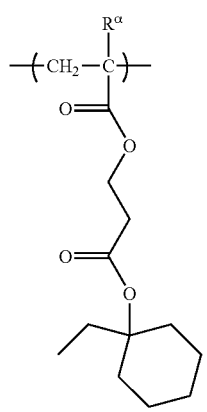 (a1-3-20)
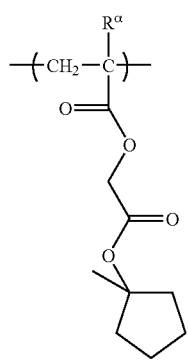 (a1-3-21)
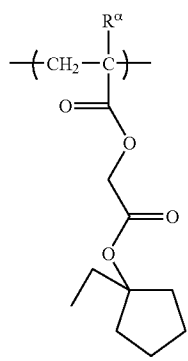 (a1-3-22)
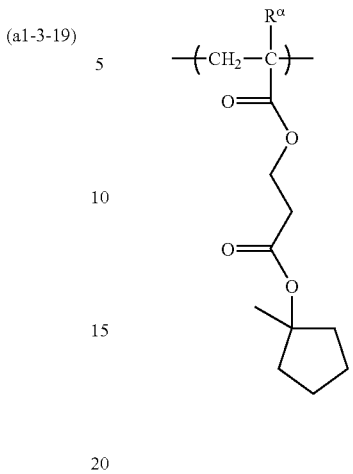 (a1-3-23)
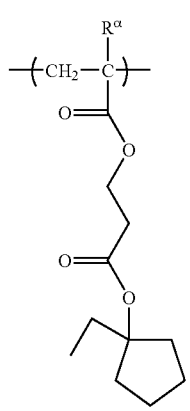 (a1-3-24)
[Chemical Formula 18]
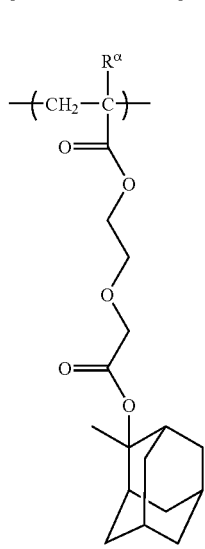 (a1-3-25)

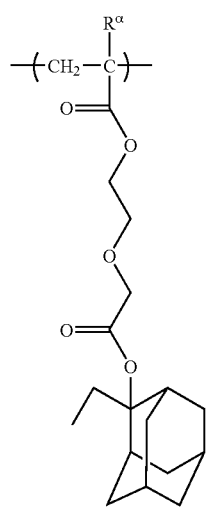
(a1-3-26)
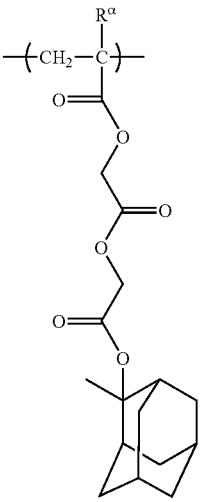
(a1-3-29)
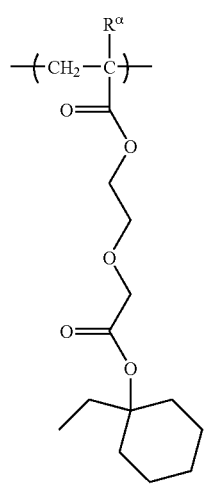
(a1-3-27)
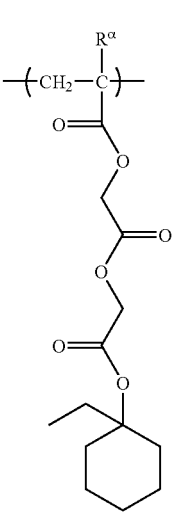
(a1-3-30)
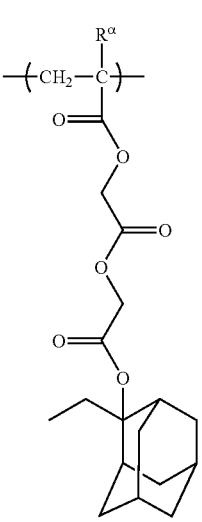
(a1-3-28)
(a1-3-31)

-continued
(a1-3-32)
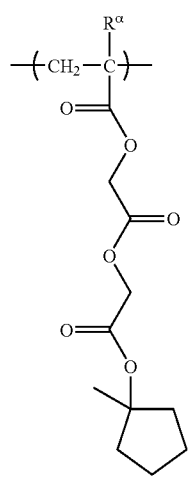
[Chemical Formula 19]
(a1-4-1)
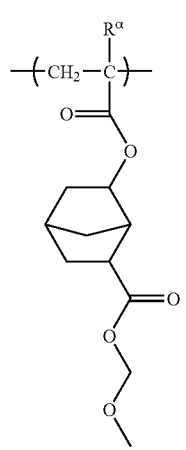
(a1-4-2)
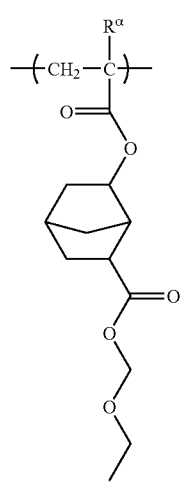
(a1-4-3)
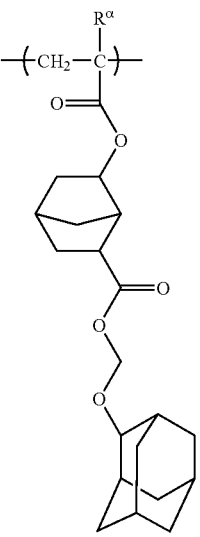
(a1-4-4)
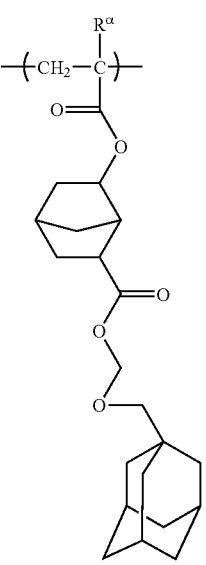
(a1-4-5)
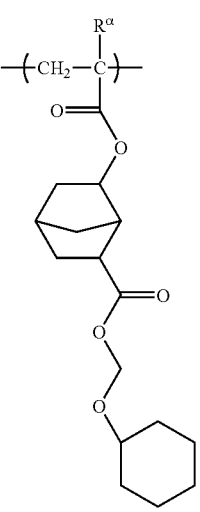

(a1-4-6)
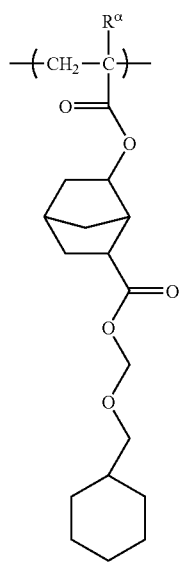
(a1-4-7)
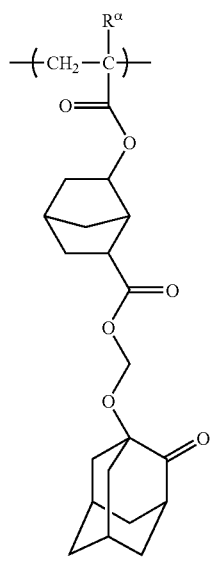
(a1-4-8)
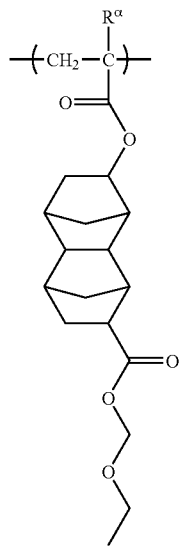
(a1-4-9)
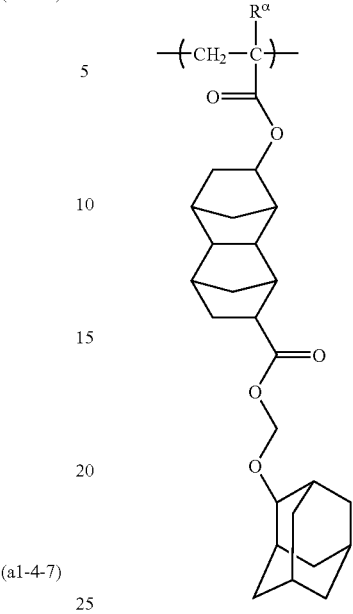
(a1-4-10)
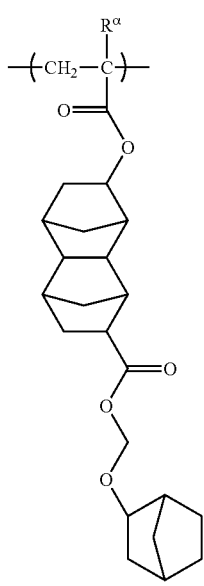

(a1-4-11)
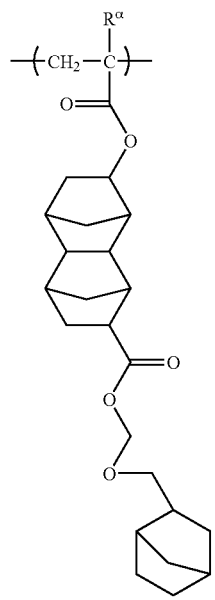
(a1-4-12)
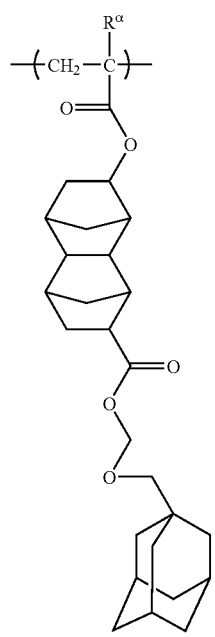
(a1-4-13)
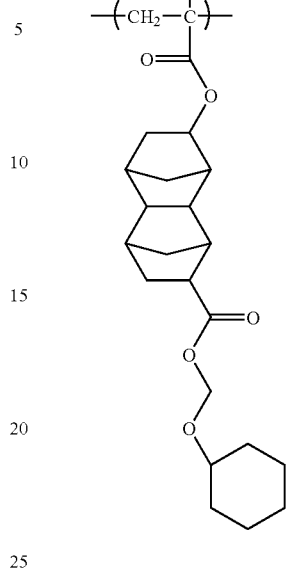
(a1-4-14)
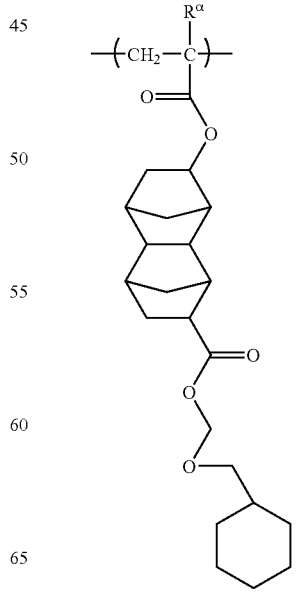

(a1-4-15)

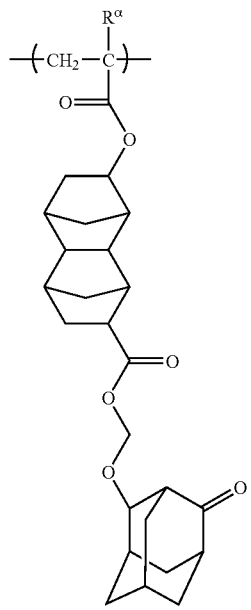

As the structural unit (a1), one type of structural unit may be used, or two or more types may be used in combination.

Among these, structural units represented by general formula (a1-1) or (a1-3) are preferable. More specifically, at least one structural unit selected from the group consisting of structural units represented by formulas (a1-1-1) to (a1-1-4), (a1-1-20) to (a1-1-23) and (a1-3-25) to (a1-3-28) is more preferable.

Further, as the structural unit (a1), structural units represented by general formula (a1-1-01) shown below which includes the structural units represented by formulas (a1-1-1) to (a1-1-3), structural units represented by general formula (a1-1-02) shown below which includes the structural units represented by formulas (a1-1-16), (a1-1-17) and (a1-1-20) to (a1-1-23), structural units represented by general formula (a1-3-01) shown below which include the structural units represented by formulas (a1-3-25) and (a1-3-26), and structural units represented by general formula (a1-3-02) shown below which include the structural units represented by formulas (a1-3-27) to (a1-3-28) are also preferable.

[Chemical Formula 20]

(a1-1-01)

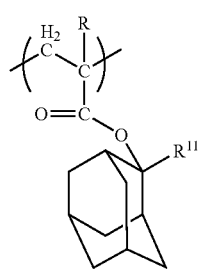

In the formula, R represents a hydrogen atom, a lower alkyl group or a halogenated lower alkyl group; and $R^{11}$ represents a lower alkyl group.

[Chemical Formula 21]

(a1-1-02)

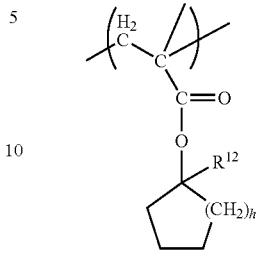

In the formula, R represents a hydrogen atom, a lower alkyl group or a halogenated lower alkyl group; $R^{12}$ represents a lower alkyl group; and h represents an integer of 1 to 6.

In general formula (a1-1-01), R is the same as defined above.

The lower alkyl group for $R^{11}$ is the same as the lower alkyl group for R, and is preferably a methyl group or an ethyl group.

In general formula (a1-1-02), R is the same as defined above.

The lower alkyl group for $R^{12}$ is the same as the lower alkyl group for R above, preferably a methyl group or an ethyl group, and most preferably an ethyl group. h is preferably 1 to 4, and most preferably 4.

[Chemical Formula 22]

(a1-3-01)

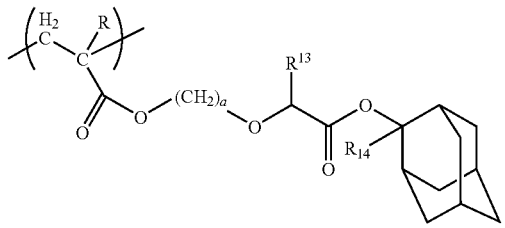

In the formula, R represents a hydrogen atom, a lower alkyl group or a halogenated lower alkyl group; $R^{14}$ represents a lower alkyl group; $R^{13}$ represents a hydrogen atom or a methyl group; and a represents an integer of 1 to 10.

[Chemical Formula 23]

(a1-3-02)

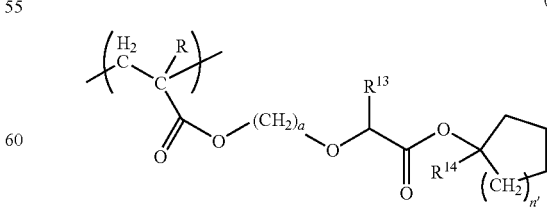

In the formula, R represents a hydrogen atom, a lower alkyl group or a halogenated lower alkyl group; $R^{14}$ represents a lower alkyl group; $R^{13}$ represents a hydrogen atom or a methyl group; a represents an integer of 1 to 10; and n' represents an integer of 1 to 6.

In general formulas (a1-3-01) and (a1-3-02), R is the same as defined above.

$R^{13}$ is preferably a hydrogen atom.

The lower alkyl group for $R^{14}$ is the same as the lower alkyl group for R, and is preferably a methyl group or an ethyl group.

a is preferably an integer of 1 to 8, more preferably an integer of 2 to 5, and most preferably 2.

In the component (A1), as the structural unit (a1), one type of structural unit may be used, or two or more types may be used in combination.

In the component (A1), the amount of the structural unit (a1) based on the combined total of all structural units constituting the component (A1) is preferably 10 to 80 mol %, more preferably 20 to 70 mol %, and still more preferably 25 to 50 mol %. When the amount of the structural unit (a1) is at least as large as the lower limit of the above-mentioned range, a pattern can be easily formed using a resist composition prepared from the component (A1). On the other hand, when the amount of the structural unit (a1) is no more than the upper limit of the above-mentioned range, a good balance can be achieved with the other structural units.

—Structural Unit (a2)

The structural unit (a2) is a structural unit derived from an acrylate ester containing a lactone-containing cyclic group.

The term "lactone-containing cyclic group" refers to a cyclic group including one ring containing a —O—C(O)— structure (lactone ring). The term "lactone ring" refers to a single ring containing a —O—C(O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings.

When the polymeric compound (A1) is used for forming a resist film, the lactone-containing cyclic group of the structural unit (a2) is effective in improving the adhesion between the resist film and the substrate, and increasing the compatibility with the developing solution containing water.

As the structural unit (a2), there is no particular limitation, and an arbitrary structural unit may be used.

Specific examples of lactone-containing monocyclic groups include a group in which one hydrogen atom has been removed from a 4- to 6-membered lactone ring, such as a group in which one hydrogen atom has been removed from β-propionolatone, a group in which one hydrogen atom has been removed from γ-butyrolactone, and a group in which one hydrogen atom has been removed from δ-valerolactone. Further, specific examples of lactone-containing polycyclic groups include groups in which one hydrogen atom has been removed from a lactone ring-containing bicycloalkane, tricycloalkane or tetracycloalkane.

More specifically, examples of the structural unit (a2) include structural units represented by general formulas (a2-1) to (a2-5) shown below.

[Chemical Formula 24]

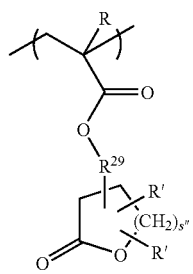
(a2-1)

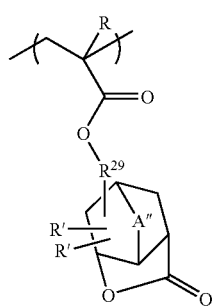
(a2-2)

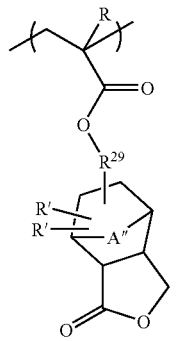
(a2-3)

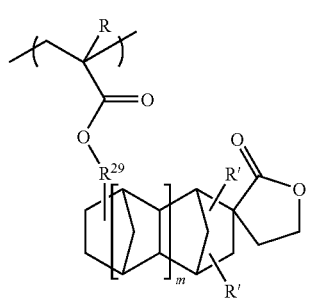
(a2-4)

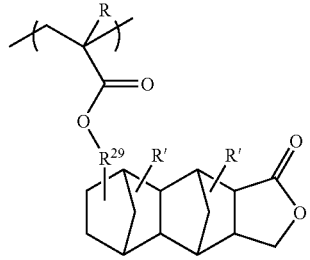
(a2-5)

In the formulas, R represents a hydrogen atom, a lower alkyl group or a halogenated lower alkyl group; each R' independently represents a hydrogen atom, an alkyl group of 1 to 5 carbon atoms, an alkoxy group of 1 to 5 carbon atoms or —COOR", wherein R" represents a hydrogen atom or an alkyl group; $R^{29}$ represents a single bond or a divalent linking group; s" represents an integer of 0 to 2; A" represents an oxygen atom, a sulfur atom or an alkylene group of 1 to 5 carbon atoms which may contain an oxygen atom or a sulfur atom; and m represents 0 or 1.

In general formulas (a2-1) to (a2-5), R is the same as defined for R in the structural unit (a1).

Examples of the alkyl group of 1 to 5 carbon atoms for R' include a methyl group, an ethyl group, a propyl group, an n-butyl group and a tert-butyl group.

Examples of the alkoxy group of 1 to 5 carbon atoms for R' include a methoxy group, an ethoxy group, an n-propoxy group, an iso-propoxy group, an n-butoxy group and a tert-butoxy group In terms of industrial availability, R' is preferably a hydrogen atom.

When R" is a linear or branched alkyl group, it preferably has 1 to 10 carbon atoms, more preferably 1 to 5 carbon atoms.

When R" is a cyclic alkyl group (cycloalkyl group), it preferably has 3 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Examples of such groups include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

As A", an alkylene group of 1 to 5 carbon atoms or —O— is preferable, more preferably an alkylene group of 1 to 5 carbon atoms, and most preferably a methylene group.

$R^{29}$ represents a single bond or a divalent linking group. Examples of divalent linking groups include the same divalent linking groups as those described above for $Y^2$ in general formula (a1-0-2). Among these, an alkylene group, an ester bond (—C(=O)—O—) or a combination thereof is preferable. The alkylene group as a divalent linking group for $R^{29}$ is preferably a linear or branched alkylene group. Specific examples include the same linear alkylene groups and branched alkylene groups as those described above for the aliphatic cyclic group A in $Y^2$.

s" is preferably 1 or 2.

Specific examples of structural units represented by general formulas (a2-1) to (a2-5) are shown below. In the formulas shown below, $R^\alpha$ represents a hydrogen atom, a methyl group or a trifluoromethyl group.

[Chemical Formula 25]

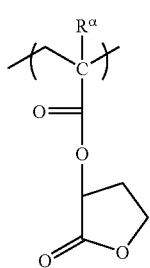
(a2-1-1)

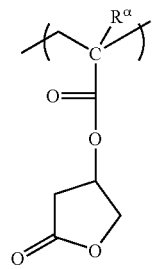
(a2-1-2)

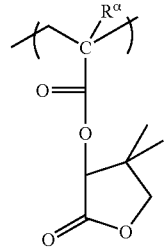
(a2-1-3)

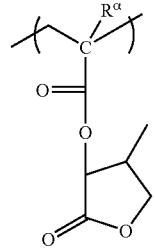
(a2-1-4)

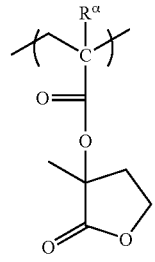
(a2-1-5)

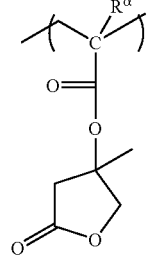
(a2-1-6)

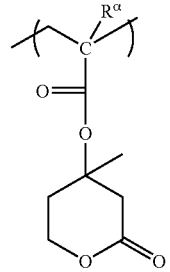
(a2-1-7)

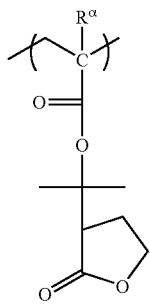
(a2-1-8)
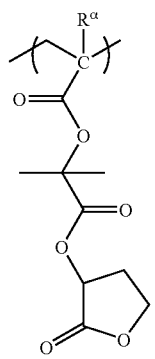
(a2-1-12)
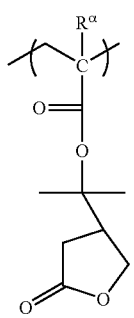
(a2-1-9)
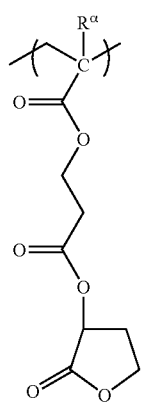
(a2-1-13)
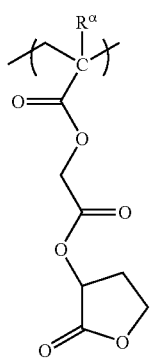
(a2-1-10)
[Chemical Formula 26]
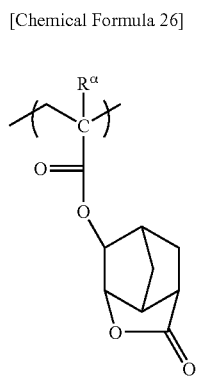
(a2-2-1)
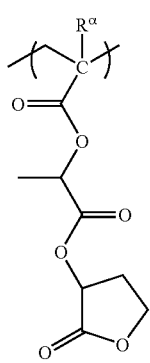
(a2-1-11)
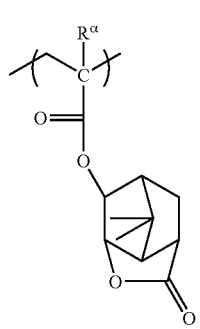
(a2-2-2)

(a2-2-3) 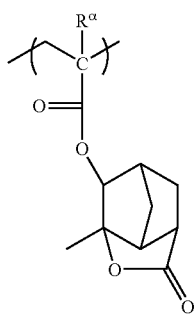
(a2-2-4) 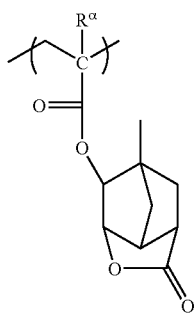
(a2-2-5) 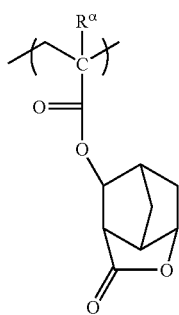
(a2-2-6) 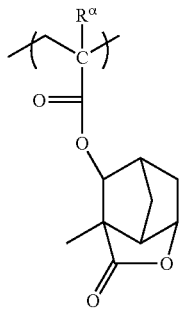
(a2-2-7) 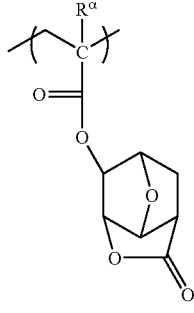
(a2-2-8) 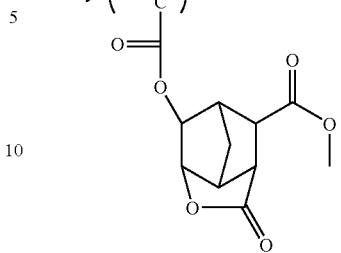
(a2-2-9) 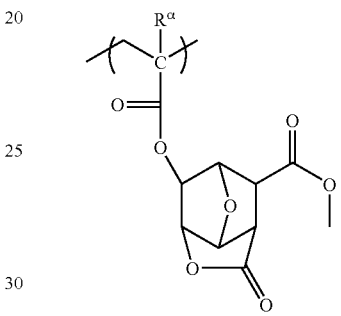
(a2-2-10) 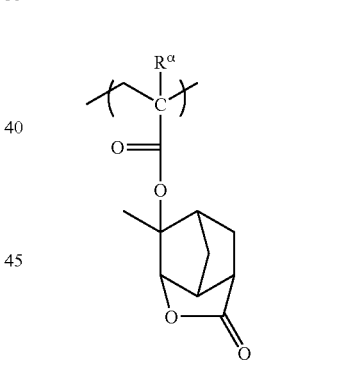
(a2-2-11) 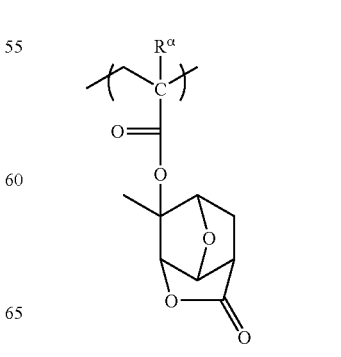

(a2-2-12)
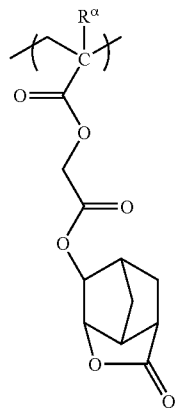
(a2-2-13)
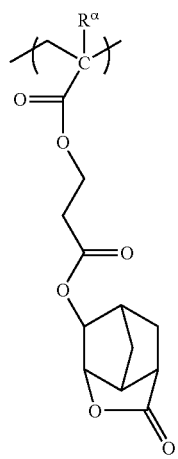
(a2-2-14)
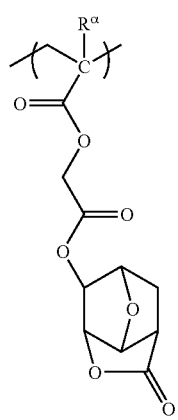
(a2-2-15)
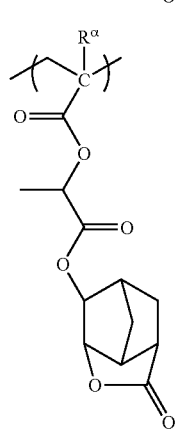
(a2-2-16)
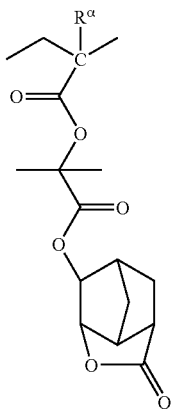
(a2-2-17)
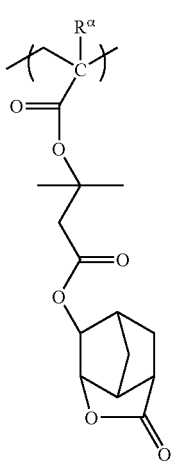
[Chemical Formula 27]
(a2-3-1)
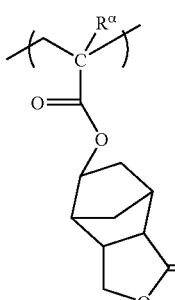
(a2-3-2)
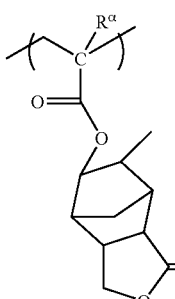

-continued
(a2-3-4)
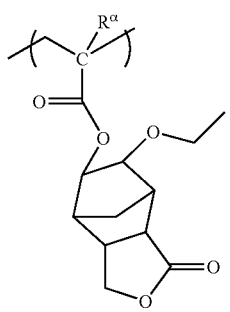
(a2-3-5)
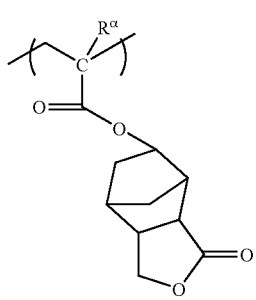
[Chemical Formula 28]
(a2-4-1)
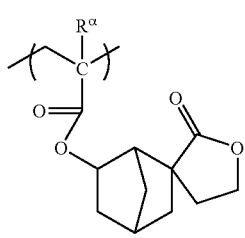
(a2-4-2)
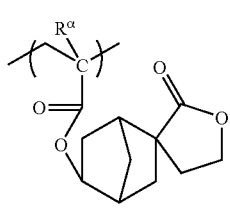
(a2-4-3)
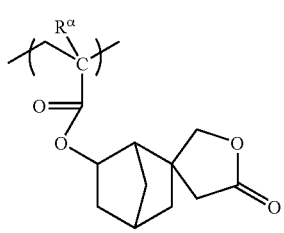
(a2-4-4)
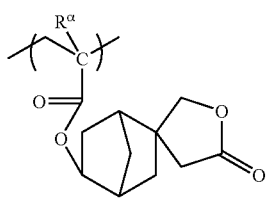
-continued
(a2-4-5)
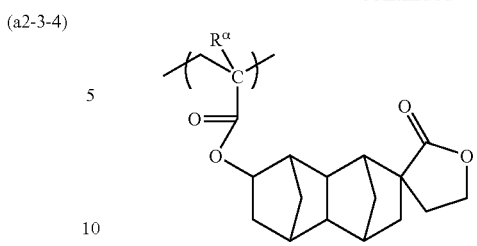
(a2-4-6)
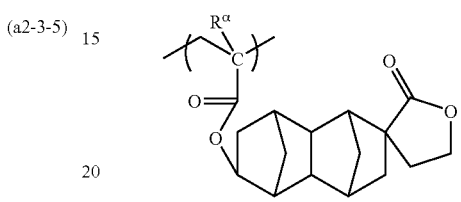
(a2-4-7)
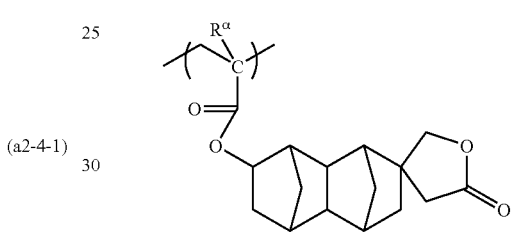
(a2-4-8)
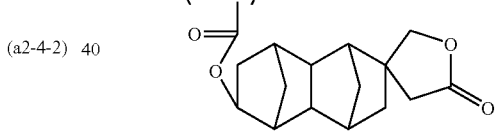
(a2-4-9)
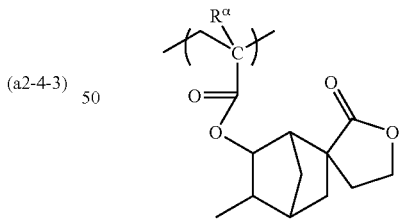
(a2-4-10)
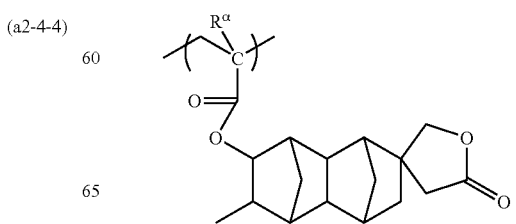

(a2-4-11)
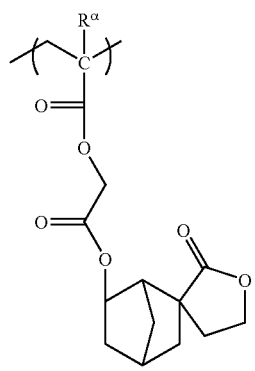
(a2-4-12)
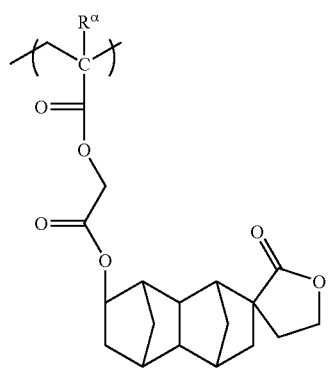
[Chemical Formula 29]
(a2-5-1)
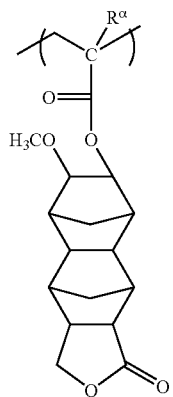
(a2-5-2)
(a2-5-3)
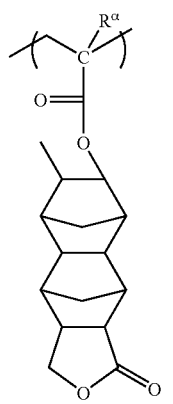
(a2-5-4)
(a2-5-5)
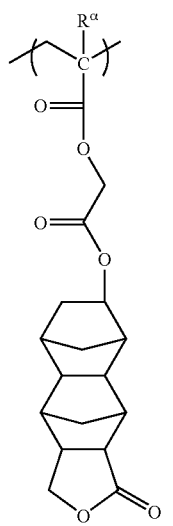

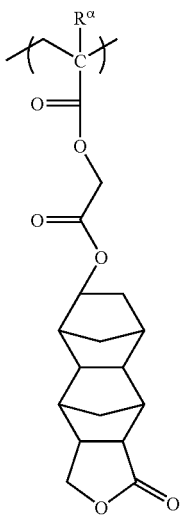

(a2-5-6)

As the structural unit (a2), at least one structural unit selected from the group consisting of formulas (a2-1) to (a2-5) is preferable, and at least one structural unit selected from the group consisting of formulas (a2-1) to (a2-3) is more preferable. Of these, it is preferable to use at least one structural unit selected from the group consisting of structural units represented by formulas (a1-1-1), (a2-2-1), (a2-2-7), (a2-3-1) and (a2-3-5).

In the component (A1), as the structural unit (a2), one type of structural unit may be used, or two or more types may be used in combination.

In the component (A1), the amount of the structural unit (a2) based on the combined total of all structural units constituting the component (A1) is preferably 5 to 60 mol %, more preferably 10 to 50 mol %, and still more preferably 20 to 50 mol %. When the amount of the structural unit (a2) is at least as large as the lower limit of the above-mentioned range, the effect of using the structural unit (a2) can be satisfactorily achieved. On the other hand, when the amount of the structural unit (a2) is no more than the upper limit of the above-mentioned range, a good balance can be achieved with the other structural units.

—Structural Unit (a3)

The structural unit (a3) is a structural unit derived from an acrylate ester containing a polar group-containing aliphatic hydrocarbon group.

When the component (A1) includes the structural unit (a3), the hydrophilicity of the component (A1) is improved, and hence, the compatibility of the component (A1) with the developing solution is improved. As a result, the alkali solubility of the exposed portions improves, which contributes to favorable improvements in the resolution.

Examples of the polar group include a hydroxyl group, cyano group, carboxyl group, or hydroxyalkyl group in which some of the hydrogen atoms of the alkyl group have been substituted with fluorine atoms, although a hydroxyl group is particularly desirable.

Examples of the aliphatic hydrocarbon group include linear or branched hydrocarbon groups (and preferably alkylene groups) of 1 to 10 carbon atoms, and polycyclic aliphatic hydrocarbon groups (polycyclic groups). These polycyclic groups can be selected appropriately from the multitude of groups that have been proposed for the resins of resist compositions designed for use with ArF excimer lasers. The polycyclic group preferably has 7 to 30 carbon atoms.

Of the various possibilities, structural units derived from an acrylate ester that include an aliphatic polycyclic group that contains a hydroxyl group, cyano group, carboxyl group or a hydroxyalkyl group in which part of the hydrogen atoms of the alkyl group have been substituted with fluorine atoms are particularly desirable. Examples of polycyclic groups include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

When the aliphatic hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid. On the other hand, when the hydrocarbon group is a polycyclic group, structural units represented by formulas (a3-1), (a3-2) and (a3-3) shown below are preferable.

[Chemical Formula 30]

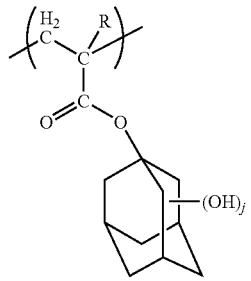

(a3-1)

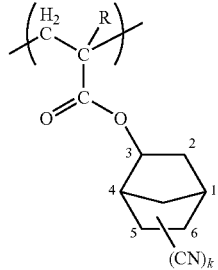

(a3-2)

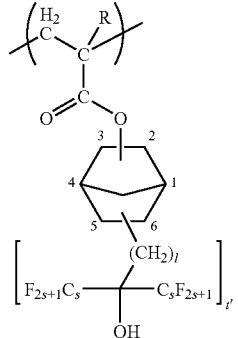

(a3-3)

In the formulas, R is the same as defined above; j is an integer of 1 to 3; k is an integer of 1 to 3; t' is an integer of 1 to 3; l is an integer of 1 to 5; and s is an integer of 1 to 3.

In formula (a3-1), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group.

j is preferably 1, and it is particularly desirable that the hydroxyl group be bonded to the 3rd position of the adamantyl group.

In formula (a3-2), k is preferably 1. The cyano group is preferably bonded to the 5th or 6th position of the norbornyl group.

In formula (a3-3), t' is preferably 1. l is preferably 1. s is preferably 1. Further, in formula (a3-3), it is preferable that a 2-norbornyl group or 3-norbornyl group be bonded to the terminal of the carboxy group of the acrylic acid. The fluorinated alkyl alcohol is preferably bonded to the 5th or 6th position of the norbornyl group.

In the component (A1), as the structural unit (a3), one type of structural unit may be used, or two or more types may be used in combination.

When the component (A1) contains the structural unit (a3), the amount of structural unit (a3) based on the combined total of all structural units constituting the component (A1) is preferably 5 to 50 mol %, more preferably 5 to 40 mol %, and still more preferably 5 to 25 mol %. When the amount of the structural unit (a3) is at least as large as the lower limit of the above-mentioned range, the effect of using the structural unit (a3) can be satisfactorily achieved. On the other hand, when the amount of the structural unit (a3) is no more than the upper limit of the above-mentioned range, a good balance can be achieved with the other structural units.

—Structural Unit (a4)

The component (A1) may also have a structural unit (a4) which is other than the above-mentioned structural units (a1) to (a3), as long as the effects of the present invention are not impaired.

As the structural unit (a4), any other structural unit which cannot be classified as one of the above structural units (a1) to (a3) can be used without any particular limitation, and any of the multitude of conventional structural units used within resist resins for ArF excimer lasers or KrF excimer lasers (and particularly for ArF excimer lasers) can be used.

As the structural unit (a4), a structural unit which contains a non-acid-dissociable aliphatic polycyclic group, and is also derived from an acrylate ester is preferable. Examples of this polycyclic group include the same groups as those described above in connection with the aforementioned structural unit (a1), and any of the multitude of conventional polycyclic groups used within the resin component of resist compositions for ArF excimer lasers or KrF excimer lasers (and particularly for ArF excimer lasers) can be used.

In consideration of industrial availability and the like, at least one polycyclic group selected from amongst a tricyclodecanyl group, adamantyl group, tetracyclododecanyl group, isobornyl group, and norbornyl group is particularly desirable. These polycyclic groups may be substituted with a linear or branched alkyl group of 1 to 5 carbon atoms.

Specific examples of the structural unit (a4) include units with structures represented by general formulas (a4-1) to (a4-5) shown below.

[Chemical Formula 31]

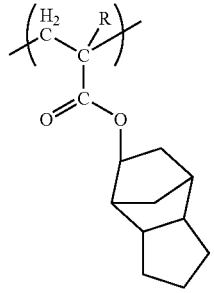

(a4-1)

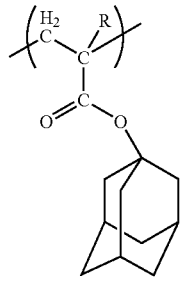

(a4-2)

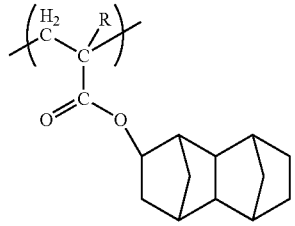

(a4-3)

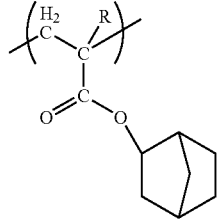

(a4-4)

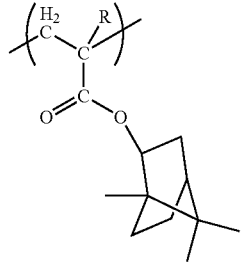

(a4-5)

In the formulas, R is the same as defined above.

When the structural unit (a4) is included in the component (A1), the amount of the structural unit (a4) based on the combined total of all the structural units that constitute the component (A1) is preferably within the range from 1 to 30 mol %, and more preferably from 10 to 20 mol %.

When the structural unit (a4) is included In the component (A1), as the structural unit (a4), one type of structural unit may be used, or two or more types may be used in combination.

In the present invention, the component (A1) preferably contains a copolymer having the structural units (a1), (a2) and (a3). Examples of such copolymers include a copolymer consisting of the structural units (a1) and (a2) and (a3), and a copolymer consisting of the structural units (a1), (a2), (a3) and (a4). As such a copolymer, one type may be used, or two or more types may be used in combination.

The component (A1) can be obtained, for example, by a conventional radical polymerization or the like of the monomers corresponding with each of the structural units, using a radical polymerization initiator such as azobisisobutyronitrile (AIBN).

Furthermore, in the component (A1), by using a chain transfer agent such as HS—CH$_2$—CH$_2$—CH$_2$—C(CF$_3$)$_2$—OH, a —C(CF$_3$)$_2$—OH group can be introduced at the terminals of the component (A1). Such a copolymer having introduced a hydroxyalkyl group in which some of the hydrogen atoms of the alkyl group are substituted with fluorine atoms is effective in reducing developing defects and LER (line edge roughness: unevenness of the side walls of a line pattern).

The weight average molecular weight (Mw) (the polystyrene equivalent value determined by gel permeation chromatography) of the component (A1) is not particularly limited, but is preferably 2,000 to 50,000, more preferably 3,000 to 30,000, and most preferably 5,000 to 20,000. By ensuring that the weight average molecular weight is no more than the upper limit of the above-mentioned range, the polymeric compound (A1) exhibits satisfactory solubility in a resist solvent when used as a resist. On the other hand, by ensuring that the weight average molecular weight is at least as large as the lower limit of the above-mentioned range, dry etching resistance and cross-sectional shape of the resist pattern becomes satisfactory.

Further, the dispersity (Mw/Mn) is preferably 1.0 to 5.0, more preferably 1.0 to 3.0, and most preferably 1.2 to 2.5. Here, Mn is the number average molecular weight.

[Component (A2)]

As the component (A2), it is preferable to use a compound that has a molecular weight of at least 500 and less than 2,000, contains a hydrophilic group, and also contains an acid dissociable, dissolution inhibiting group described above in connection with the component (A1). Specific examples include compounds containing a plurality of phenol skeletons in which a part of the hydrogen atoms within hydroxyl groups have been substituted with the aforementioned acid dissociable, dissolution inhibiting groups.

Examples of the component (A2) include low molecular weight phenolic compounds in which a portion of the hydroxyl group hydrogen atoms have been substituted with an aforementioned acid dissociable, dissolution inhibiting group, and these types of compounds are known, for example, as sensitizers or heat resistance improvers for use in non-chemically amplified g-line or i-line resists.

Examples of these low molecular weight phenol compounds include bis(4-hydroxyphenyl)methane, bis(2,3,4-trihydroxyphenyl)methane, 2-(4-hydroxyphenyl)-2-(4'-hydroxyphenyl)propane, 2-(2,3,4-trihydroxyphenyl)-2-(2',3', 4'-trihydroxyphenyl)propane, tris(4-hydroxyphenyl)methane, bis(4-hydroxy-3,5-dimethylphenyl)-2-hydroxyphenylmethane, bis(4-hydroxy-2,5-dimethylphenyl)-2-hydroxyphenylmethane, bis(4-hydroxy-3,5-dimethylphenyl)-3,4-dihydroxyphenylmethane, bis(4-hydroxy-2,5-dimethylphenyl)-3,4-dihydroxyphenylmethane, bis(4-hydroxy-3-methylphenyl)-3,4-dihydroxyphenylmethane, bis(3-cyclohexyl-4-hydroxy-6-methylphenyl)-4-hydroxyphenylmethane, bis(3-cyclohexyl-4-hydroxy-6-methylphenyl)-3,4-dihydroxyphenylmethane, 1-[1-(4-hydroxyphenyl)isopropyl]-4-[1,1-bis(4-hydroxyphenyl)ethyl]benzene, and dimers, trimers and tetramers of formalin condensation products of phenols such as phenol, m-cresol, p-cresol and xylenol. Needless to say, the low molecular weight phenol compound is not limited to these examples.

Also, there are no particular limitations on the acid dissociable, dissolution inhibiting group, and suitable examples include the groups described above.

As the component (A), one type may be used, or two or more types of compounds may be used in combination.

In the resist composition of the present invention, the amount of the component (A) can be appropriately adjusted depending on the thickness of the resist film to be formed, and the like.

<Component (B)>

In the present invention, the component (B) includes at least one member selected from the group consisting of an acid generator (B1) (hereafter, referred to as "component (B1)") including a compound represented by general formula (b1-1) shown below, an acid generator (B1') (hereafter, referred to as component (B1')) including a compound represented by general formula (b1-1') shown below and a compound (B1") (hereafter, referred to as component (B1")) including a compound represented by general formula (b1-1") shown below (hereafter, this group of compounds is generally referred to as "component (B1-0)").

[Chemical Formula 32]

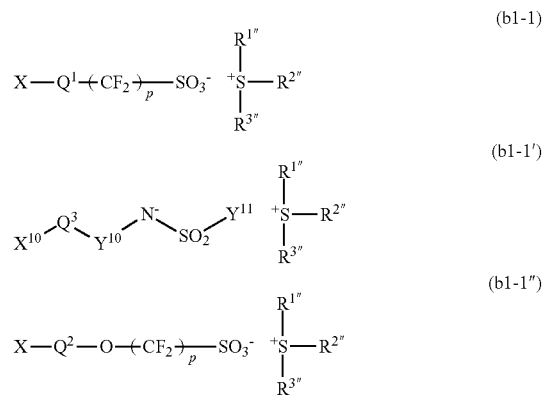

In the formulas, each of $R^{1''}$ to $R^{3''}$ independently represents an aryl group which may have a substituent or an alkyl group which may have a substituent, with the provision that at least one of $R^{1''}$ to $R^{3''}$ represents a substituted aryl group having part of the hydrogen atoms substituted with a group represented by general formula (b1-1-0) shown below, and two of $R^{1''}$ to $R^{3''}$ may be bonded to each other to form a ring with the sulfur atom; X represents a hydrocarbon group of 3 to 30 carbon atoms which may have a substituent; $Q^1$ represents a divalent linking group containing a carbonyl group; p represents an integer of 1 to 3; $X^{10}$ represents a hydrocarbon group of 1 to 30 carbon atoms which may have a substituent; $Q^3$ represents a single bond or a divalent linking group; $Y^{10}$ represents —C(=O)— or —SO$_2$—; $Y^{11}$ represents an alkyl group of 1 to 10 carbon atoms which may have a substituent or a fluorinated alkyl group which may have a substituent: and $Q^2$ represents a single bond or an alkylene group.

[Chemical Formula 33]

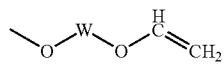

(b1-1-0)

In formula (b1-1-0), W represents a linear or branched alkylene group of 2 to 10 carbon atoms.

—Cation Moiety of Component (B1-0)

In formula (b1-1), formula (b1-1') and formula (b1-1"), each of $R^{1\prime\prime}$ to $R^{3\prime\prime}$ independently represents an aryl group which may have a substituent or an alkyl group which may have a substituent, with the provision that at least one of $R^{1\prime\prime}$ to $R^{3\prime\prime}$ represents a substituted aryl group having part of the hydrogen atoms substituted with a group represented by general formula (b1-1-0).

That is, at least one of $R^{1\prime\prime}$ to $R^{3\prime\prime}$ represents an aryl group. In the present invention, it is preferable that two or more of $R^{1\prime\prime}$ to $R^{3\prime\prime}$ represents an aryl group, and it is particularly desirable that all of $R^{1\prime\prime}$ to $R^{3\prime\prime}$ are aryl groups.

Here, the aryl group or the alkyl group "has a substituent" means that part or all of the hydrogen atoms within the hydrocarbon group has been substituted with groups or atoms other than hydrogen atom.

The aryl group for $R^{1\prime\prime}$ to $R^{3\prime\prime}$ is not particularly limited. For example, an aryl group of 6 to 20 carbon atoms is preferable, and an aryl group of 6 to 10 carbon atoms is more preferable because it can be synthesized at a low cost. Specific examples thereof include a phenyl group and a naphthyl group.

The alkyl group for $R^{1\prime\prime}$ to $R^{3\prime\prime}$ is not particularly limited and includes, for example, a linear, branched or cyclic alkyl group having 1 to 10 carbon atoms. In terms of achieving excellent resolution, the alkyl group preferably has 1 to 5 carbon atoms. Specific examples thereof include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decanyl group, and a methyl group is most preferable because it is excellent in resolution and can be synthesized at a low cost.

Among these, each of $R^{1\prime\prime}$ to $R^{3\prime\prime}$ preferably represents an aryl group which may have a substituent, and a phenyl group or a naphthyl group which may have a substituent is more preferable. It is still more preferable that all of $R^{1\prime\prime}$ to $R^{3\prime\prime}$ represent an aryl group which may have a substituent, and it is particularly desirable that all of $R^{1\prime\prime}$ to $R^{3\prime\prime}$ represents a phenyl group or a naphthyl group which may have a substituent.

In formula (b1-1), formula (b1-1') and formula (b1-1"), at least one of $R^{1\prime\prime}$ to $R^{3\prime\prime}$ represents a substituted aryl group having part of the hydrogen atoms substituted with a group represented by general formula (b1-1-0).

The aforementioned "part of hydrogen atoms" is preferably 1 to 4 hydrogen atoms, more preferably 1 to 3 hydrogen atoms, and most preferably 1 hydrogen atom.

In formula (b1-1-0), W represents a linear alkylene group of 2 to 10 carbon atoms or a branched alkylene group of 2 to 10 carbon atoms.

W has 2 to 10 carbon atoms, preferably 2 to 9 carbon atoms, and more preferably 2 to 5 carbon atoms. Specific examples thereof include an ethylene group [—$CH_2CH_2$—]; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$CH(CH_2CH_3)CH_2$—; a trimethylene group (n-propylene group) [—$CH_2CH_2CH_2$—]; alkyltrimethylene groups such as —$CH(CH_3)CH_2CH_2$—, and —$CH_2CH(CH_3)CH_2$—; a tetramethylene group [—$CH_2CH_2CH_2CH_2$—]; alkyltetramethylene groups such as —$CH(CH_3)CH_2CH_2CH_2$—, and —$CH_2CH(CH_3)CH_2CH_2$—; a pentamethylene group [—$CH_2CH_2CH_2CH_2CH_2$—]; a hexamethylene group [—$CH_2CH_2CH_2CH_2CH_2CH_2$—]; a heptamethylene group [—$CH_2CH_2CH_2CH_2CH_2CH_2CH_2$—]; an octamethylene group [—$CH_2CH_2CH_2CH_2CH_2CH_2CH_2CH_2$—]; a nonamethylene group [—$CH_2CH_2CH_2CH_2CH_2CH_2CH_2CH_2CH_2$—]; and a decamethylene group [—$CH_2CH_2CH_2CH_2CH_2CH_2CH_2CH_2CH_2CH_2$—].

Among these, in terms of lithography properties, resist pattern shape and ease in synthesis, an ethylene group, a butylene group or a nonamethylene group is preferable, and an ethylene group is particularly desirable.

The aryl group or the alkyl group for $R^{1\prime\prime}$ to $R^{3\prime\prime}$ may have a substituent other than the group represented by general formula (b1-1-0).

Examples of such a substituent which the aryl group or the alkyl group may have include an alkyl group, an alkoxy group, an alkoxyalkyloxy group, an alkoxycarbonylalkyloxy group, a halogen atom, a hydroxy group, and —($R^{4\prime\prime}$)—C(=O)—$R^{5\prime}$. $R^{4\prime\prime}$ represents an alkylene group of 1 to 5 carbon atoms. $R^{5\prime}$ represents an aryl group. As the aryl group for $R^{5\prime}$, the same aryl groups as those described above for $R^{1\prime\prime}$ to $R^{3\prime\prime}$ can be mentioned.

The alkyl group as the substituent for $R^{1\prime\prime}$ to $R^{3\prime\prime}$ is preferably an alkyl group of 1 to 5 carbon atoms, more preferably a methyl group, an ethyl group, a propyl group, an n-butyl group or a tert-butyl group, and a methyl group is particularly desirable.

The alkoxy group as the substituent for $R^{1\prime\prime}$ to $R^{3\prime\prime}$ is preferably an alkoxy group having 1 to 5 carbon atoms, and a methoxy group, an ethoxy group, an n-propoxy group, an iso-propoxy group, an n-butoxy group or a tert-butoxy group is particularly desirable.

The halogen atom as the substituent for $R^{1\prime\prime}$ to $R^{3\prime\prime}$ is preferably a fluorine atom.

Examples of alkoxyalkyloxy groups as the substituent for $R^{1\prime\prime}$ to $R^{3\prime\prime}$ include groups represented by a general formula shown below:

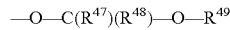

—O—C($R^{47}$)($R^{48}$)—O—$R^{49}$

In the formula, $R^{47}$ and $R^{48}$ each independently represents a hydrogen atom or a linear or branched alkyl group; and $R^{49}$ represents an alkyl group.

The alkyl group for $R^{47}$ and $R^{48}$ preferably has 1 to 5 carbon atoms, and may be either linear or branched. As the alkyl group, an ethyl group or a methyl group is more preferable, and a methyl group is most preferable.

It is preferable that at least one of $R^{47}$ and $R^{48}$ be a hydrogen atom. It is particularly desirable that at least one of $R^{47}$ and $R^{48}$ be a hydrogen atom, and the other be a hydrogen atom or a methyl group.

The alkyl group for $R^{49}$ preferably has 1 to 15 carbon atoms, and may be linear, branched or cyclic.

The linear or branched alkyl group for $R^{49}$ preferably has 1 to 5 carbon atoms. Examples thereof include a methyl group, an ethyl group, a propyl group, an n-butyl group and a tert-butyl group.

The cyclic alkyl group for $R^{49}$ preferably has 4 to 15 carbon atoms, more preferably 4 to 12, and most preferably 5 to 10.

Specific examples thereof include groups in which one or more hydrogen atoms have been removed from a monocycloalkane or a polycycloalkane such as a bicycloalkane, tricycloalkane or tetracycloalkane, and which may or may not be substituted with an alkyl group of 1 to 5 carbon atoms, a fluorine atom or a fluorinated alkyl group. Examples of the monocycloalkane include cyclopentane and cyclohexane. Examples of polycycloalkanes include adamantane, norbornane, isobornane, tricyclodecane and tetracyclododecane. Among these, a group in which one or more hydrogen atoms have been removed from adamantane is preferable.

Examples of alkoxycarbonylalkyloxy groups as the substituent for $R^{1\prime\prime}$ to $R^{3\prime\prime}$ include groups represented by a general formula shown below:

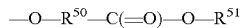

—O—R$^{50}$—C(=O)—O—R$^{51}$

In the formula, $R^{50}$ represents a linear or branched alkylene group, and $R^{51}$ represents a tertiary alkyl group.

The linear or branched alkylene group for $R^{50}$ preferably has 1 to 5 carbon atoms, and examples thereof include a methylene group, an ethylene group, a trimethylene group, a tetramethylene group and a 1,1-dimethylethylene group.

Examples of the tertiary alkyl group for $R^{51}$ include a 2-methyl-2-adamantyl group, a 2-ethyl-2-adamantyl group, a 1-methyl-1-cyclopentyl group, a 1-ethyl-1-cyclopentyl group, a 1-methyl-1-cyclohexyl group, a 1-ethyl-1-cyclohexyl group, a 1-(1-adamantyl)-1-methylethyl group, a 1-(1-adamantyl)-1-methylpropyl group, a 1-(1-adamantyl)-1-methylbutyl group, a 1-(1-adamantyl)-1-methylpentyl group, a 1-(1-cyclopentyl)-1-methylethyl group, a 1-(1-cyclopentyl)-1-methylpropyl group, a 1-(1-cyclopentyl)-1-methylbutyl group, a 1-(1-cyclopentyl)-1-methylpentyl group, a 1-(1-cyclohexyl)-1-methylethyl group, a 1-(1-cyclohexyl)-1-methylpropyl group, a 1-(1-cyclohexyl)-1-methylbutyl group, a 1-(1-cyclohexyl)-1-methylpentyl group, a tert-butyl group, a tert-pentyl group and a tert-hexyl group.

In formula (b1-1), formula (b1-1') and formula (b1-1"), two of $R^{1\prime\prime}$ to $R^{3\prime\prime}$ may be bonded to each other to form a ring with the sulfur atom.

In such a case, the ring including the sulfur atom is preferably a 3- to 10-membered ring, and more preferably a 5- to 7-membered ring.

When two of $R^{1\prime\prime}$ to $R^{3\prime\prime}$ in formula (b1-1), formula (b1-1') and formula (b1-1") are bonded to each other to form a ring with the sulfur atom, the remaining one of $R^{1\prime\prime}$ to $R^{3\prime\prime}$ is preferably an aryl group.

As examples of the aryl group, the same aryl groups as those described above for $R^{1\prime\prime}$ to $R^{3\prime\prime}$ can be mentioned.

Specific examples of preferable cation moieties for the component (B1-0) are shown below.

[Chemical Formula 34]

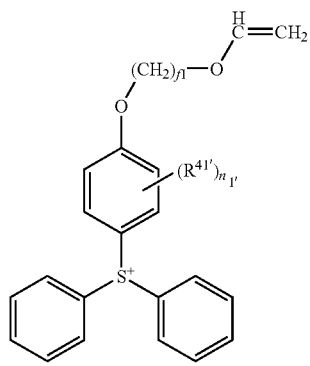

(b1-2-1)

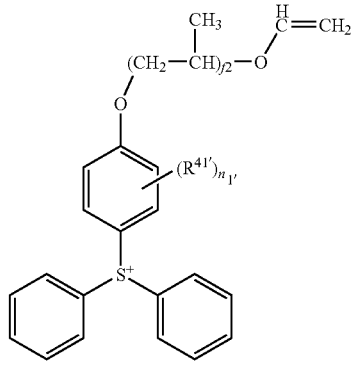

(b1-2-2)

In the formulas, f1 represents an integer of 2 to 10; f2 represents an integer of 1 to 3; $R^{41\prime}$ represents an alkyl group of 1 to 5 carbon atoms; and $n_1{}'$ represents an integer of 0 to 3.

In formula (a1-0-1), f1 represents an integer of 2 to 10, preferably an integer of 2 to 9, more preferably an integer of 2 to 5, and most preferably 2.

$R^{41\prime}$ represents an alkyl group of 1 to 5 carbon atoms, preferably a linear or branched alkyl group, more preferably a methyl group, an ethyl group, a propyl group, an n-butyl group or a tert-butyl group, and most preferably a methyl group.

$n_1{}'$ represents an integer of 0 to 3, preferably 1 or 2, and most preferably 2.

When $n_1{}'$ does not represent 0, the $R^{41\prime}$ group is preferably bonded to a carbon atom adjacent to the carbon atom within the benzene ring to which the oxygen atom on the terminal of the group represented by the formula "—O—(CH$_2$)$_{f1}$—O—CH=CH$_2$" is bonded.

In formula (b1-2-2), f2 represents an integer of 1 to 3, preferably 1 or 2, and most preferably 1.

$R^{41\prime}$ and $n_1{}'$ are the same as defined above.

When $n_1{}'$ does not represent 0, the $R^{41\prime}$ group is preferably bonded to a carbon atom adjacent to the carbon atom within the benzene ring to which the oxygen atom on the terminal of the group represented by the formula "—O—(CH$_2$—CH(CH$_3$))$_{f2}$—O—CH=CH$_2$" is bonded.

—Anion Moiety of Component (B1)

In general formula (b1-1), X represents a hydrocarbon group of 3 to 30 carbon atoms which may have a substituent.

The hydrocarbon group for X may be either an aromatic hydrocarbon group or an aliphatic hydrocarbon group.

The aromatic hydrocarbon group is a hydrocarbon group having an aromatic ring. The aromatic hydrocarbon group preferably has 3 to 30 carbon atoms, more preferably 5 to 30, still more preferably 5 to 20, still more preferably 6 to 15, and most preferably 6 to 12. Here, the number of carbon atoms within a substituent(s) is not included in the number of carbon atoms of the aromatic hydrocarbon group.

Specific examples of aromatic hydrocarbon groups include an aryl group which is an aromatic hydrocarbon ring having one hydrogen atom removed therefrom, such as a phenyl group, a biphenyl group, a fluorenyl group, a naphthyl group, an anthryl group or a phenanthryl group; and an alkylaryl group such as a benzyl group, a phenethyl group, a 1-naphthylmethyl group, a 2-naphthylmethyl group, a 1-naphthylethyl group, or a 2-naphthylethyl group. The alkyl chain within the arylalkyl group preferably has 1 to 4 carbon atom, more preferably 1 or 2, and most preferably 1.

The aromatic hydrocarbon group may have a substituent. For example, part of the carbon atoms constituting the aromatic ring within the aromatic hydrocarbon group may be substituted with a hetero atom, or a hydrogen atom bonded to the aromatic ring within the aromatic hydrocarbon group may be substituted with a substituent.

In the former example, a heteroaryl group in which part of the carbon atoms constituting the ring within the aforementioned aryl group has been substituted with a hetero atom such as an oxygen atom, a sulfur atom or a nitrogen atom, and a heteroarylalkyl group in which part of the carbon atoms constituting the aromatic hydrocarbon ring within the aforementioned arylalkyl group has been substituted with the aforementioned heteroatom can be used. In such a case, with respect to the partial structure "X-$Q^1$-" of the anion moiety in general formula (b1-1), the atom within $Q^1$ to which X is bonded is preferably a carbon atom.

In the latter example, as the substituent for the aromatic hydrocarbon group, an alkyl group, an alkoxy group, a halogen atom, a halogenated alkyl group, a hydroxyl group, an oxygen atom (=O), a substituent containing a nitrogen atom (nitrogen atom-containing substituent described later) or the like can be used.

The alkyl group as the substituent for the aromatic hydrocarbon group is preferably an alkyl group of 1 to 5 carbon atoms, and a methyl group, an ethyl group, a propyl group, an n-butyl group or a tert-butyl group is particularly desirable.

The alkoxy group as the substituent for the aromatic hydrocarbon group is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the halogen atom as the substituent for the aromatic hydrocarbon group include a fluorine atom, a chlorine atom, a bromine atom and an iodine atom, and a fluorine atom is preferable.

Example of the halogenated alkyl group as the substituent for the aromatic hydrocarbon group includes a group in which part or all of the hydrogen atoms within the aforementioned alkyl group have been substituted with the aforementioned halogen atoms.

The aliphatic hydrocarbon group for X may be either a saturated aliphatic hydrocarbon group, or an unsaturated aliphatic hydrocarbon group. Further, the aliphatic hydrocarbon group may be linear, branched or cyclic, or a combination thereof.

In the aliphatic hydrocarbon group for X, a part of the carbon atoms constituting the aliphatic hydrocarbon group may be substituted with a substituent group containing a hetero atom, or a part or all of the hydrogen atoms constituting the aliphatic hydrocarbon group may be substituted with a substituent group containing a hetero atom.

As the "hetero atom" for X, there is no particular limitation as long as it is an atom other than a carbon atom and a hydrogen atom. Examples of hetero atoms include a halogen atom, an oxygen atom, a sulfur atom and a nitrogen atom. Examples of halogen atoms include a fluorine atom, a chlorine atom, an iodine atom and a bromine atom.

The substituent group containing a hetero atom may consist of a hetero atom, or may be a group containing a group or atom other than a hetero atom.

Specific examples of the substituent group for substituting part of the carbon atoms include —O—, —C(=O)—O—, —C(=O)—, —O—C(=O)—, —C(=O)—NH—, —NH— (the H may be replaced with a substituent such as an alkyl group or an acyl group), —S—, —S(=O)$_2$— and —S(=O)$_2$—O—. When the aliphatic hydrocarbon group is cyclic, the aliphatic hydrocarbon group may contain any of these substituent groups in the ring structure.

Examples of the substituent group for substituting part or all of the hydrogen atoms include an alkoxy group, a halogen atom, a halogenated alkyl group, a hydroxyl group, an oxygen atom (=O) and a substituent containing a nitrogen atom described later (e.g., a cyano group).

The aforementioned alkoxy group is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the aforementioned halogen atom include a fluorine atom, a chlorine atom, a bromine atom and an iodine atom, and a fluorine atom is preferable.

Example of the aforementioned halogenated alkyl group includes a group in which part or all of the hydrogen atoms within an alkyl group of 1 to 5 carbon atoms (e.g., a methyl group, an ethyl group, a propyl group, an n-butyl group or a tert-butyl group) have been substituted with the aforementioned halogen atoms.

As the aliphatic hydrocarbon group, a linear or branched saturated hydrocarbon group, a linear or branched monovalent unsaturated hydrocarbon group, or a cyclic aliphatic hydrocarbon group (aliphatic cyclic group) is preferable. Further, a group in which a linear or branched, saturated or unsaturated hydrocarbon group is bonded to an aliphatic cyclic group is also preferable.

The linear saturated hydrocarbon group (alkyl group) preferably has 3 to 20 carbon atoms, more preferably 3 to 15, and most preferably 3 to 10. Specific examples include a propyl group, a butyl group, a pentyl group, a hexyl group, a heptyl group, an octyl group, a nonyl group, a decanyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched saturated hydrocarbon group (alkyl group) preferably has 3 to 20 carbon atoms, more preferably 3 to 15, and most preferably 3 to 10. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

The unsaturated hydrocarbon group preferably has 3 to 10 carbon atoms, more preferably 3 to 5, still more preferably 3 or 4, and most preferably 3. Examples of linear monovalent unsaturated hydrocarbon groups include a propenyl group (an allyl group) and a butynyl group. Examples of branched monovalent unsaturated hydrocarbon groups include a 1-methylpropenyl group and a 2-methylpropenyl group.

Among the above-mentioned examples, as the unsaturated hydrocarbon group, a propenyl group is particularly desirable.

The aliphatic cyclic group may be either a monocyclic group or a polycyclic group. The aliphatic cyclic group preferably has 3 to 30 carbon atoms, more preferably 5 to 30, still more preferably 5 to 20, still more preferably 6 to 15, and most preferably 6 to 12.

As the aliphatic cyclic group, a group in which one or more hydrogen atoms have been removed from a monocycloalkane or a polycycloalkane such as a bicycloalkane, tricycloalkane or tetracycloalkane can be used. Specific examples include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

When the aliphatic cyclic group does not contain a hetero atom-containing substituent group in the ring structure thereof, the aliphatic cyclic group is preferably a polycyclic group, more preferably a group in which one or more hydrogen atoms have been removed from a polycycloalkane, and a group in which one or more hydrogen atoms have been removed from adamantane is particularly desirable.

When the aliphatic cyclic group contains a hetero atom-containing substituent group in the ring structure thereof, the hetero atom-containing substituent group is preferably —O—, —C(=O)—O—, —S—, —S(=O)$_2$— or —S(=O)$_2$—O—. Specific examples of such aliphatic cyclic groups include groups represented by formulas (L1) to (L5) and (S1) to (S4) shown below.

[Chemical Formula 35]

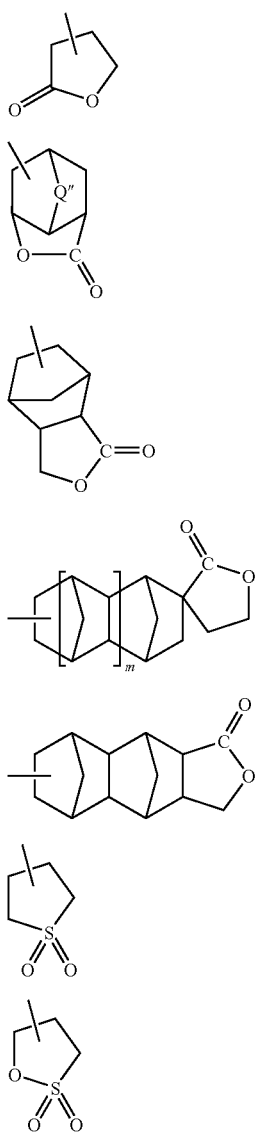

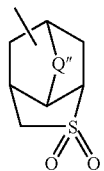

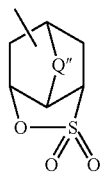

In the formulas, Q" represents an alkylene group of 1 to 5 carbon atoms, —O—, —S—, —O—R$^{98}$— or —S—R$^{99}$— (wherein each of R$^{98}$ and R$^{99}$ independently represents an alkylene group of 1 to 5 carbon atoms); and m represents 0 or 1.

Specific examples of the alkylene group for Q", R$^{98}$ and R$^{99}$ include a methylene group [—CH$_2$—]; alkylmethylene groups such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)—, and —C(CH$_2$CH$_3$)$_2$—; an ethylene group [—CH$_2$CH$_2$—]; alkylethylene groups such as —CH(CH$_3$)CH$_2$—, —CH(CH$_3$)CH(CH$_3$)—, —C(CH$_3$)$_2$CH$_2$—, —CH(CH$_2$CH$_3$)CH$_2$—, and —CH(CH$_2$CH$_3$)CH$_2$—; a trimethylene group (n-propylene group) [—CH$_2$CH$_2$CH$_2$—]; alkyltrimethylene groups such as —CH(CH$_3$)CH$_2$CH$_2$—, and —CH$_2$CH(CH$_3$)CH$_2$—; a tetramethylene group [—CH$_2$CH$_2$CH$_2$CH$_2$—]; alkyltetramethylene groups such as —CH(CH$_3$)CH$_2$CH$_2$CH$_2$—, and —CH$_2$CH(CH$_3$)CH$_2$CH$_2$—; and a pentamethylene group [—CH$_2$CH$_2$CH$_2$CH$_2$CH$_2$—].

In these aliphatic cyclic groups, part of the hydrogen atoms bonded to the carbon atoms constituting the ring structure may be substituted with a substituent. Examples of substituents include an alkyl group, an alkoxy group, a halogen atom, a halogenated alkyl group, a hydroxyl group and an oxygen atom (=O).

As the alkyl group, an alkyl group of 1 to 5 carbon atoms is preferable, and a methyl group, an ethyl group, a propyl group, an n-butyl group or a tert-butyl group is particularly desirable.

As the alkoxy group and the halogen atom, the same groups as the aforementioned substituent groups for substituting a part or all of the hydrogen atoms can be used.

As a group in which a linear or branched, saturated or unsaturated hydrocarbon group is bonded to an aliphatic cyclic group, for example, a group in which a linear or branched, saturated hydrocarbon group is bonded to a carbon atom constituting the ring structure of an aliphatic cyclic group is preferable, a group in which a linear, saturated hydrocarbon group is bonded to the carbon atom is more preferable, and a group in which a linear alkylene group is bonded to the carbon atom is particularly desirable.

Further, especially when X represents a group containing a nitrogen atom, examples of X include a hydrocarbon group having a substituent containing a nitrogen atom (hereafter, this group is referred to as "nitrogen-containing substituent") and a heterocyclic group containing a nitrogen atom as the hetero atom (hereafter, this group is referred to as "nitrogen-containing heterocyclic group"). These organic groups may have, apart from the nitrogen-containing substituent, a substituent other than a nitrogen-containing substituent (hereafter, referred to as "non-nitrogen-containing substituent").

As the nitrogen-containing heterocyclic group for X, a monovalent group in which one hydrogen atom has been removed from a heterocyclic group containing a nitrogen atom as the hetero atom (i.e., a nitrogen-containing heterocyclic group) can be mentioned. Examples of the nitrogen-containing heterocyclic group include unsaturated, monocyclic nitrogen-containing hetero rings, such as pyridine, pyrrole, pyrrazole, imidazole, 1,2,3-triazole, 1,2,4-triazole, tetrazole, pyrimidine, pyrazine and 1,3,5-triazine; saturated, monocyclic nitrogen-containing hetero rings, such as piperidine, piperazine and pyrrolidine; and polycyclic nitrogen-containing hetero rings, such as quinoline, isoquinoline, indole, pyrrolo[2,3-b]pyridine, indazole, benzimidazole, benzotriazole, carbazole, acridine, 1,5-diazabicyclo[4.3.0]-5-nonene, 1,8-diazabicyclo[5.4.0]-7-undecene, hexamethylenetetramine and 1,4-diazabicyclo[2.2.2]octane.

The nitrogen-containing heterocyclic group may be either a monocyclic group or a polycyclic group. The nitrogen-containing heterocyclic group has 3 to 30 carbon atoms, more preferably 5 to 30 carbon atoms, and still more preferably 5 to 20 carbon atoms.

Examples of the nitrogen-containing substituent for X include the aforementioned nitrogen-containing heterocyclic group, as well as an amino group ($H_2N-$), an imino group ($HN=$), a cyano group ($N\equiv C-$) and an ammonio group ($^+NH_3-$). These nitrogen-containing substituents may have part or all of the hydrogen atoms substituted with a non-nitrogen-containing substituent.

Specific examples of the nitrogen-containing substituent for X include nitrogen-containing heterocyclic groups, such as a 2-pyridyl group, a 3-pyridyl group, a 4-pyridyl group and a piperidino group; an amino group; an alkylamino group; a dialkylamino group; an imino group; an alkylimino group; a cyano group; and a trialkylammonio group. Among these, a nitrogen-containing heterocyclic group such as a 4-pyridyl group is preferable.

Examples of the non-nitrogen-containing substituent for X include an alkyl group, an aryl group, an alkoxy group, a halogen atom, a halogenated alkyl group, a hydroxyl group and an oxygen atom ($=O$).

As the alkyl group, an alkyl group of 1 to 5 carbon atoms is preferable, and a methyl group, an ethyl group, a propyl group, an n-butyl group or a tert-butyl group is particularly desirable.

Examples of aryl groups include a phenyl group, a tolyl group and a naphthyl group.

Examples of halogen atoms include a fluorine atom, a chlorine atom, an iodine atom and a bromine atom.

The aforementioned alkoxy group is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the aforementioned halogen atom include a fluorine atom, a chlorine atom, a bromine atom and an iodine atom, and a fluorine atom is preferable.

Example of the aforementioned halogenated alkyl group includes a group in which part or all of the hydrogen atoms within an alkyl group of 1 to 5 carbon atoms (e.g., a methyl group, an ethyl group, a propyl group, an n-butyl group or a tert-butyl group) have been substituted with the aforementioned halogen atoms.

When X represents a hydrocarbon group which has a nitrogen-containing substituent, the hydrocarbon group may be either an aliphatic hydrocarbon group or an aromatic hydrocarbon group, and examples thereof include the same aliphatic hydrocarbon groups and aromatic hydrocarbon groups as those described above for the "hydrocarbon group for X".

Specific examples of the group represented by X that contains a nitrogen atom include nitrogen-containing heterocyclic groups, such as a 2-pyridyl group, a 3-pyridyl group and a 4-pyridyl group; aminoalkyl groups, such as an aminomethyl group, a 1-aminoethyl group and a 2-aminoethyl group; alkylaminoalkyl groups, such as a methylaminomethyl group; dialkylaminoalkyl groups, such as a dimethylaminomethyl group; aminoaryl groups, such as a 2-aminophenyl group and a 4-aminophenyl group; alkylaminoaryl groups, such as a (methylamino)phenyl group; and dialkylaminoaryl groups, such as a (dimethylamino)phenyl group and a (diethylamino)phenyl group. Among these, a nitrogen-containing heterocyclic group such as a 4-pyridyl group is preferable.

In the present invention, as X, a cyclic group which may have a substituent is preferable. The cyclic group may be either an aromatic hydrocarbon group which may have a substituent, or an aliphatic cyclic group which may have a substituent.

As the aromatic hydrocarbon group, a naphthyl group which may have a substituent, or a phenyl group which may have a substituent is preferable.

As the aliphatic cyclic group which may have a substituent, an aliphatic polycyclic group which may have a substituent is preferable. As the aliphatic polycyclic group, the aforementioned group in which one or more hydrogen atoms have been removed from a polycycloalkane, and groups represented by formulas (L2) to (L5), (S3) and (S4) are preferable.

In formula (b1-1), $Q^1$ represents a divalent linking group containing a carbonyl group.

$Q^1$ may contain an atom other than carbon and oxygen. Examples of atoms other than carbon and oxygen include a hydrogen atom, a sulfur atom and a nitrogen atom.

Examples of divalent linking groups that contain a carbonyl group include non-hydrocarbon, carbonyl group-containing linking groups, such as an ester bond ($-C(=O)-O-$), an amide bond ($-C(=O)-NH-$), a carbonyl group ($-C(=O)-$), a carbonate bond ($-O-C(=O)-O-$); and groups that contain a non-hydrocarbon, carbonyl group-containing linking group.

Examples of the group that contains a non-hydrocarbon, carbonyl group-containing linking group include combinations of any of such non-hydrocarbon, carbonyl group-containing linking groups with a groups selected from an alkylene group and an oxygen atom (an ether bond: $-O-$).

Specific examples of such combinations include $-O-R^{91}-O-C(=O)-$, $-C(=O)-O-R^{92}-$, $-C(=O)-O-R^{93}-O-C(=O)-$, $-R^{94}-C(=O)-O-R^{95}-O-C(=O)-$ (in the formulas, each of $R^{91}$ to $R^{95}$ independently represents an alkylene group).

The alkylene group for $R^{91}$ to $R^{95}$ is preferably a linear or branched alkylene group, and preferably has 1 to 12 carbon atoms, more preferably 1 to 5, and most preferably 1 to 3.

Specific examples of alkylene groups include a methylene group [$-CH_2-$]; alkylmethylene groups such as $-CH(CH_3)-$, $-CH(CH_2CH_3)-$, $-C(CH_3)_2-$, $-C(CH_3)(CH_2CH_3)-$, $-C(CH_3)(CH_2CH_2CH_3)-$ and $-C(CH_2CH_3)_2-$; an ethylene group [$-CH_2CH_2-$]; alkylethylene groups such as $-CH(CH_3)CH_2-$, $-CH(CH_3)CH(CH_3)-$, $-C(CH_3)_2CH_2-$ and $-CH(CH_2CH_3)CH_2-$, and $-CH(CH_2CH_3)CH_2-$; a trimethylene group (n-propylene group) [$-CH_2CH_2CH_2-$]; alkyltrimethylene groups such as $-CH(CH_3)CH_2CH_2-$ and $-CH_2CH(CH_3)CH_2-$; a tetramethylene group [$-CH_2CH_2CH_2CH_2-$]; alkyltetramethylene groups such as —CH(CH$_3$)CH$_2$CH$_2$CH$_2$— and —CH$_2$CH(CH$_3$)CH$_2$CH$_2$—; and a pentamethylene group [—CH$_2$CH$_2$CH$_2$CH$_2$CH$_2$—].

In formula (b1-1), p represents an integer of 1 to 3, preferably 1 or 2, and most preferably 1.

Specific examples of preferable anion moieties for the component (B1) are shown below.

[Chemical Formula 36]

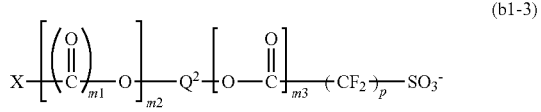

(b1-3)

In formula (b1-3), X represents a hydrocarbon group of 3 to 30 carbon atoms which may have a substituent; Q$^2$ represents a single bond or an alkylene group; p represents an integer of 1 to 3; each of m1 to m3 represents 0 or 1, with the provision that both of m2+m3 and m1+m3 are not equal to 0.

In formula (b1-3), X and p are respectfully the same as defined for X and p in formula (b1-1).

As the alkylene group for Q$^2$, the same alkylene groups as those described above for R$^{91}$ to R$^{95}$ in the explanation of Q$^1$ can be mentioned.

Each of m1 to m3 represents 0 or 1, provided that both of m2+m3 and m1+m3 are not equal to 0.

When m3=0, m2 represents 1, and m1 represents 1.

More specific examples of preferable anion moieties for the component (B1) include:

an anion represented by general formula (b1-3-10) shown below, an anion represented by general formula (b1-3-20) shown below, an anion represented by general formula (b1-3-31) shown below, and an anion represented by general formula (b1-3-41) shown below.

—Anion Represented by General Formula (b1-3-10)

[Chemical Formula 37]

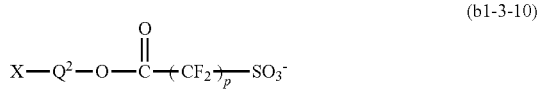

(b1-3-10)

In formula (b1-3-10), X, Q$^2$ and p are the same as defined above.

In general formula (b1-3-10), as X, an aliphatic cyclic group which may have a substituent, a linear aliphatic hydrocarbon group which may have a substituent, or an aromatic hydrocarbon group which may have a substituent is preferable. Of these, an aliphatic cyclic group which contains a hetero atom-containing substituent in the ring structure thereof is more preferable As the alkylene group for Q$^2$, the same alkylene groups as those described above for Q$^1$ can be mentioned.

As Q$^2$, a single bond or a methylene group is particularly desirable. Especially, when X is an aliphatic cyclic group which may have a substituent, Q$^2$ is preferably a single bond. On the other hand, when X is an aromatic hydrocarbon group, Q$^2$ is preferably a methylene group.

p is preferably 1 or 2, and most preferably 1.

Specific examples of preferable anions represented by general formula (b1-3-10) are shown below.

[Chemical Formula 38]

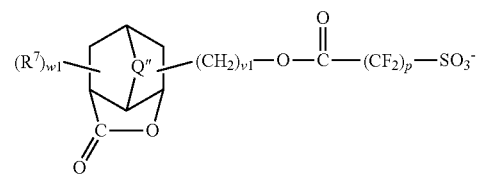

(b1-3-11)

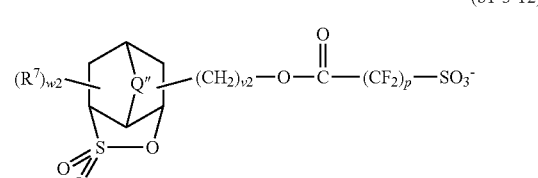

(b1-3-12)

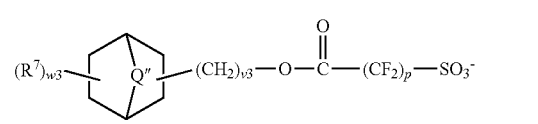

(b1-3-13)

In the formulas, Q" is the same as defined above; R$^7$ represents a substituent; each of w1 to w3 independently represents an integer of 0 to 3; each of v1 to v3 independently represents an integer of 0 to 5; and p represents an integer of 1 to 3.

In the formulas, as the substituent for R$^7$, the same groups as those which the aforementioned aliphatic hydrocarbon group or aromatic hydrocarbon group for X may have as a substituent can be mentioned.

If there are two or more of the R$^7$ group, as indicated by the values w1 to w3, then the two or more of the R$^7$ groups may be the same or different from each other.

It is preferable that each of v1 to v3 independently represents an integer of 0 to 3, most preferably 0.

It is preferable that each of w1 to w3 independently represents an integer of 0 to 2, and most preferably 0.

p is preferably 1 or 2, and most preferably 1.

—Anion Represented by General Formula (b1-3-20)

[Chemical Formula 39]

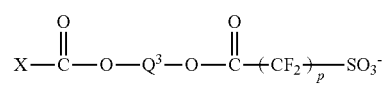

(b1-3-20)

In formula (b1-3-20), X and p are the same as defined above; and Q$^3$ represents an alkylene group.

In general formula (b1-3-20), as X, an aliphatic cyclic group which may have a substituent, a linear aliphatic hydrocarbon group which may have a substituent, or an aromatic hydrocarbon group which may have a substituent is preferable.

p is preferably 1 or 2, and most preferably 1.

As the alkylene group for Q$^3$, the same alkylene groups as those described above for Q$^1$ can be mentioned.

Specific examples of preferable anions represented by general formula (b1-3-20) are shown below.

[Chemical Formula 40]

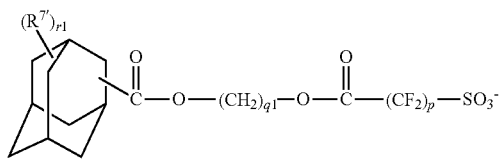
(b1-3-21)

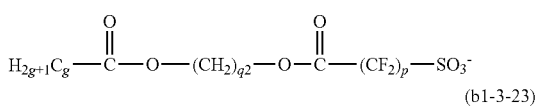
(b1-3-22)

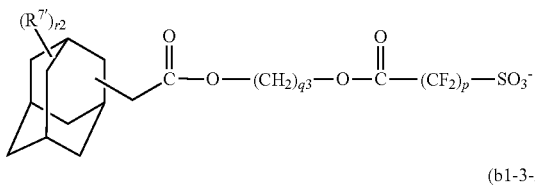
(b1-3-23)

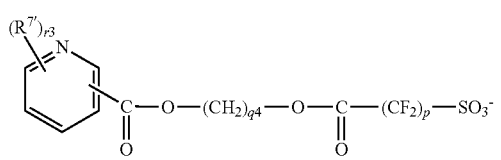
(b1-3-24)

In the formulas, p is the same as defined above; $R^{7\prime}$ represents a substituent; each of r1 to r3 independently represents an integer of 0 to 3; each of q1 to q4 independently represents an integer of 1 to 12; and g represents an integer of 1 to 20.

In the formulas, as the substituent for $R^{7\prime}$, the same groups as those described above for $R^7$ can be mentioned.

If there are two or more of the $R^{7\prime}$ group, as indicated by the values r1 to r3, then the two or more of the $R^{7\prime}$ groups may be the same or different from each other.

It is preferable that each of r1 to r3 independently represent an integer of 0 to 2, more preferably 0 or 1, and still more preferably 0.

It is preferable that each of q1 to q4 independently represent 1 to 8, more preferably 1 to 5, and still more preferably 1 to 3.

g is preferably 1 to 15, and more preferably 1 to 10.
p is preferably 1 or 2, and most preferably 1.
—Anion Represented by General Formula (b1-3-31)

[Chemical Formula 41]

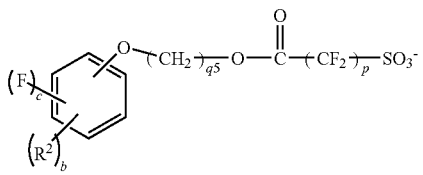
(b1-3-31)

In the formula, p is the same as defined above; q5 represents an integer of 0 to 5; $R^2$ represents an alkyl group, an alkoxy group, a halogen atom (exclusive of fluorine), a halogenated alkyl group, a hydroxy group, an oxygen atom ($=$O), —COOR'', —OC($=$O)R'', a hydroxyalkyl group or a cyano group; b represents an integer of 0 to 2, and c represents an integer of 1 to 5, with the provision that 1≤b+c≤5.

p is preferably 1 or 2, and most preferably 1.
q5 is preferably 1 to 4, more preferably 1 or 2, and most preferably 2.

Examples of the alkyl group, alkoxy group, halogen atom (excluding fluorine) and halogenated alkyl group for $R^2$ include the same groups as those described above for the substituent which a cyclic group represented by X may have.

With respect to —COOR'' and —OC($=$O)R'' for $R^2$, R'' is the same as defined for R'' in the aforementioned structural unit (a2).

As the hydroxyalkyl group for $R^2$, groups in which at least one hydrogen atom of the aforementioned alkyl groups for $R^2$ has been substituted with a hydroxy group can be mentioned.

b is most preferably 0.
c is preferably 2 to 5, and most preferably 5.
However, 1≤b+c≤5.
—Anion Represented by General Formula (b1-3-41)

[Chemical Formula 42]

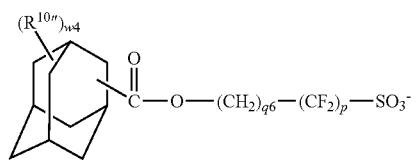
(b1-3-41)

In the formula, p is the same as defined above; q6 represents an integer of 1 to 12; w4 represents an integer of 0 to 3; and $R^{10\prime\prime}$ represents a substituent.

Examples of the substituent for $R^{10\prime\prime}$ include an alkyl group, an alkoxy group, a halogen atom, a halogenated alkyl group, a hydroxyl group, an oxygen atom ($=$O) and a cyano group.

As the alkyl group, an alkyl group of 1 to 5 carbon atoms is preferable, and a methyl group, an ethyl group, a propyl group, an n-butyl group or a tert-butyl group is particularly desirable.

The aforementioned alkoxy group is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the aforementioned halogen atom include a fluorine atom, a chlorine atom, a bromine atom and an iodine atom, and a fluorine atom is preferable.

Example of the aforementioned halogenated alkyl group includes a group in which part or all of the hydrogen atoms within an alkyl group of 1 to 5 carbon atoms (e.g., a methyl group, an ethyl group, a propyl group, an n-butyl group or a tert-butyl group) have been substituted with the aforementioned halogen atoms.

If there are two or more of the $R^{10\prime\prime}$ group, as indicated by the value w4, then the two or more of the $R^{10\prime\prime}$ groups may be the same or different from each other.

p is preferably 1 or 2, and most preferably 1.
q6 is preferably 1 to 5, more preferably 1 to 3, and most preferably 1.
w4 is preferably an integer of 0 to 2, more preferably 0 or 1, and still more preferably 0.

—Anion Moiety of Component (B1')

In formula (b1-1'), $X^{10}$ represents a hydrocarbon group of 1 to 30 carbon atoms which may have a substituent.

The hydrocarbon group for $X^{10}$ may be either an aromatic hydrocarbon group or an aliphatic hydrocarbon group.

The aromatic hydrocarbon group for $X^{10}$ is a hydrocarbon group having an aromatic ring, and the same aromatic hydrocarbon groups as those described above for X in formula (b1-1) can be mentioned.

As the aliphatic hydrocarbon group, a linear or branched saturated hydrocarbon group, a linear or branched monovalent unsaturated hydrocarbon group, or a cyclic aliphatic hydrocarbon group (aliphatic cyclic group) is preferable. Further, a group in which a linear or branched, saturated or unsaturated hydrocarbon group is bonded to an aliphatic cyclic group is also preferable.

The linear saturated hydrocarbon group (alkyl group) preferably has 1 to 20 carbon atoms, more preferably 1 to 15, and most preferably 3 to 12. Specific examples include a methyl group, an ethyl group, a propyl group, a butyl group, a pentyl group, a hexyl group, a heptyl group, an octyl group, a nonyl group, a decanyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched saturated hydrocarbon group (alkyl group) preferably has 3 to 20 carbon atoms, more preferably 3 to 15, and most preferably 3 to 10. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

The unsaturated hydrocarbon group preferably has 2 to 10 carbon atoms, more preferably 2 to 5, still more preferably 2 to 4, and most preferably 3. Examples of linear monovalent unsaturated hydrocarbon groups include a vinyl group, a propenyl group (an allyl group) and a butynyl group. Examples of branched monovalent unsaturated hydrocarbon groups include a 1-methylpropenyl group and a 2-methylpropenyl group.

Among the above-mentioned examples, as the unsaturated hydrocarbon group, a propenyl group is particularly desirable.

As the aliphatic cyclic group, the same aliphatic cyclic groups as those described above for X in formula (b1-1) can be mentioned.

In the present invention, as $X^{10}$, a cyclic group which may have a substituent is preferable.

The cyclic group may be either an aromatic hydrocarbon group which may have a substituent, or an aliphatic cyclic group which may have a substituent, and an aliphatic cyclic group which may have a substituent is preferable.

As the aromatic hydrocarbon group, a naphthyl group which may have a substituent, or a phenyl group which may have a substituent is preferable.

As the aliphatic cyclic group which may have a substituent, the aforementioned groups in which one or more hydrogen atoms have been removed from a monocycloalkane, the aforementioned group in which one or more hydrogen atoms have been removed from a polycycloalkane, and groups represented by formulas (L2) to (L5), (S3) and (S4) are preferable.

In formula (b1-1'), $Q^3$ represents a single bond or a divalent linking group.

Examples of the divalent linking group for $Q^3$ include the following:

an alkylene group or a fluorinated alkylene group;

non-hydrocarbon, oxygen-containing linking groups, such as an oxygen atom (ether bond: —O—), an ester bond (—C(=O)—O—), an amide bond (—C(=O)—NH—), a carbonyl group (—C(=O)—) and a carbonate bond (—O—C(=O)—O—); and combinations of the aforementioned non-hydrocarbon, oxygen-containing linking groups with an alkylene group or a fluorinated alkylene group.

The alkylene group or fluorinated alkylene group for $Q^3$ is preferably a linear or branched group. Further, the alkylene group or fluorinated alkylene group preferably has 1 to 12 carbon atoms, more preferably 1 to 5 carbon atoms, still more preferably 1 to 4 carbon atoms, and most preferably 1 to 3 carbon atoms.

Specific examples of alkylene groups for $Q^3$ include a methylene group [—$CH_2$—]; alkylmethylene groups such as —$CH(CH_3)$—, —$CH(CH_2CH_3)$—, —$C(CH_3)_2$—, —$C(CH_3)(CH_2CH_3)$—, —$CH(CH_2CH_2CH_3)$—, —$C(CH_3)(CH_2CH_2CH_3)$—, and —$C(CH_2CH_3)_2$—; an ethylene group [—$CH_2CH_2$—]; alkylethylene groups, such as —$CH(CH_3)CH_2$—, —$CH(CH_3)CH(CH_3)$—, —$C(CH_3)_2CH_2$—, —$CH(CH_2CH_3)CH_2$—, and —$CH(CH_2CH_3)CH_2$—; a trimethylene group (an n-propylene group) [—$CH_2CH_2CH_2$—]; alkyltrimethylene groups, such as —$CH(CH_3)CH_2CH_2$—, and —$CH_2CH(CH_3)CH_2$—; a tetramethylene group [—$CH_2CH_2CH_2CH_2$—]; alkyltetramethylene groups, such as —$CH(CH_3)CH_2CH_2CH_2$—, and —$CH_2CH(CH_3)CH_2CH_2$—; and a pentamethylene group [—$CH_2CH_2CH_2CH_2CH_2$—].

As the fluorinated alkylene group for $Q^3$, groups in which part or all of the hydrogen atoms of the aforementioned alkylene groups for $Q^3$ have been substituted with a fluorine atom can be mentioned, and specific examples include —$CF_2$—, —$CF_2CF_2$—, —$CF_2CF_2CF_2$—, —$CF(CF_3)CF_2$—, —$CF(CF_2CF_3)$—, —$C(CF_3)_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—, —$CF(CF_2CF_2CF_3)$—, —$C(CF_3)(CF_2CF_3)$—; —CHF—, —$CH_2CF_2$—, —$CH_2CH_2CF_2$—, —$CH_2CF_2CF_2$—, —$CH(CF_3)CH_2$—, —$CH(CF_2CF_3)$—, —$C(CH_3)(CF_3)$—, —$CH_2CH_2CH_2CF_2$—, —$CH_2CH_2CF_2CF_2$—, —$CH(CF_3)CH_2CH_2$—, —$CH_2CH(CF_3)CH_2$—, —$CH(CF_3)CH(CF_3)$—, and —$C(CF_3)_2CH_2$—.

Examples of combinations of the aforementioned non-hydrocarbon, oxygen-containing linking groups with an alkylene group or a fluorinated alkylene group include —$R^{91}$—O—, —C(=O)—O—$R^{92}$—, —C(=O)—O—$R^{93}$—O—, and —$R^{94}$—C(=O)—O—$R^{95}$—O—. In the formulas, each of $R^{91}$ to $R^{95}$ independently represents an alkylene group or a fluorinated alkylene group, and specific examples thereof include the same alkylene groups or fluorinated alkylene groups as those described above for $Q^3$.

When $Y^{10}$ (described later) in formula (b1-1') represents —$SO_2$—, it is particularly desirable that a carbon atom of $Q^3$ bonded to the sulfur atom within $Y^{10}$ be fluorinated. In such a case, an acid having a strong acid strength is generated from the component (B1') upon exposure. As a result, a resist pattern with an excellent shape can be formed, and various lithography properties such as EL margin and the like can be improved.

In formula (b1-1'), when $Y^{10}$ (described later) represents —$SO_2$—, the acid strength of the acid generated upon exposure can be controlled by adjusting the number of fluorine atoms within $Q^3$. When the carbon atom is not fluorinated, although the acid strength becomes weak, improvement in roughness and the like can be expected.

The alkylene group or the fluorinated alkylene group for $Q^3$ may have a substituent. The alkylene group or fluorinated alkylene group "has a substituent" means that part or all of the hydrogen atoms or fluorine atoms in the alkylene group or fluorinated alkylene group has been substituted with groups other than hydrogen atoms and fluorine atoms.

Examples of substituents which the alkylene group or fluorinated alkylene group may have include an alkoxy group of 1 to 4 carbon atoms, and a hydroxyl group.

As $Q^3$, a single bond, an alkylene group, a fluorinated alkylene group or a divalent linking group containing an ether bond is preferable, and a single bond, an alkylene group or —$R^{91}$—O— is particularly desirable.

In formula (b1-1'), $Y^{10}$ represents —C(=O)— or —$SO_2$—.

In formula (b1-1'), $Y^{11}$ represents an alkyl group of 1 to 10 carbon atoms which may have a substituent or a fluorinated alkyl group of 1 to 10 carbon atoms which may have a substituent.

$Y^{11}$ has 1 to 10 carbon atoms, preferably 1 to 8 carbon atoms, and more preferably 1 to 4 carbon atoms.

$Y^{11}$ is preferably a fluorinated alkyl group which may have a substituent because the acid strength of the generated acid becomes stronger. The fluorination ratio (percentage (%) of the number of fluorine atoms, base on the total number of fluorine atoms and hydrogen atoms) is preferably 50 to 100%, more preferably 80 to 100%, and still more preferably 85 to 100%.

Further, when $Y^{11}$ is a fluorinated alkyl group, the skeleton "$Y^{11}$—$SO_2$—" exhibits excellent decomposability as compared to a perfluoroalkyl chain of 6 to 10 carbon atoms which is hardly decomposable, and bioaccumulation can be minimized to improve ease in handling. Furthermore, the fluorinated alkyl group is preferable in that the acid generator-component (B) can be uniformly distributed within a resist film.

The alkyl group or fluorinated alkyl group for $Y^{11}$ may have a substituent. Examples of substituents include an alkoxy group, a halogen atom other than fluorine, a halogenated alkyl group, a hydroxyl group and an oxygen atom (=O).

The alkoxy group as the substituent is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the halogen atom (other than fluorine) as the substituent include a chlorine atom, a bromine atom and an iodine atom.

Examples of the halogenated alkyl group as the substituent include groups in which part or all of the hydrogen atoms within the aforementioned alkyl groups has been substituted with the aforementioned halogen atoms.

Specific examples of preferable anion moieties for the component (B1') are shown below.

[Chemical Formula 43]

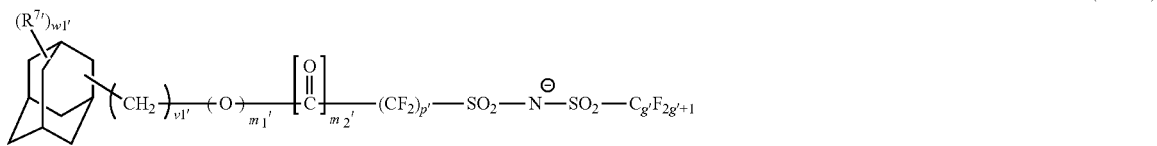

(b1-3-1')

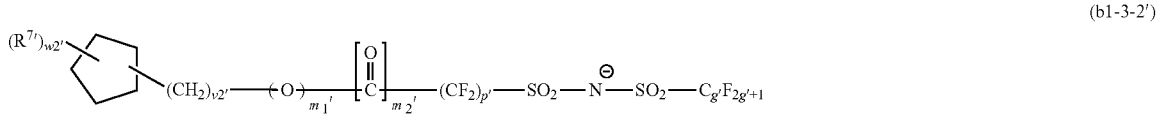

(b1-3-2')

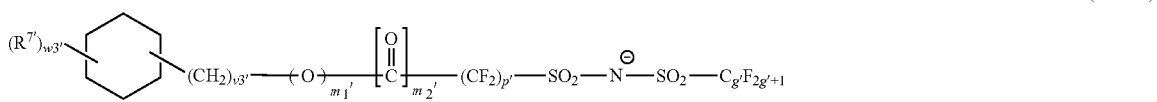

(b1-3-3')

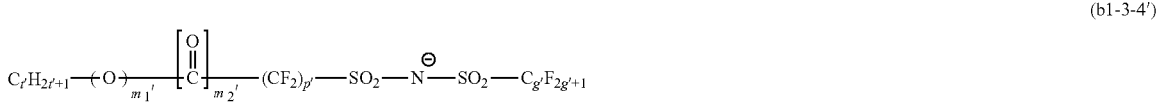

(b1-3-4')

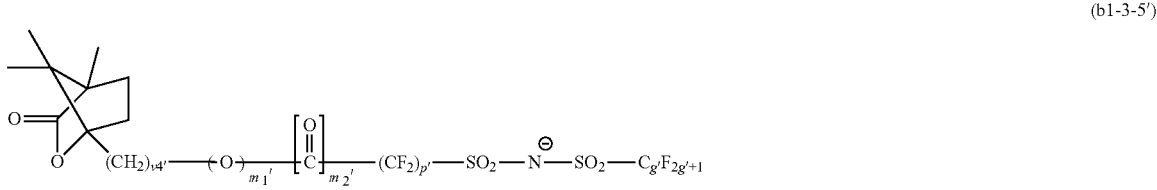

(b1-3-5')

-continued

[Chemical Formula 44]

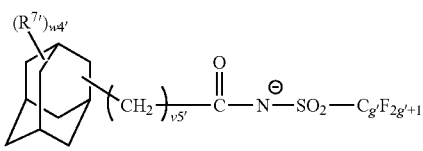
(b1-3-6')

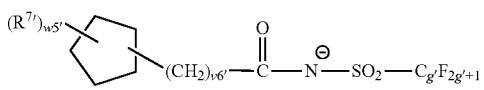
(b1-3-7')

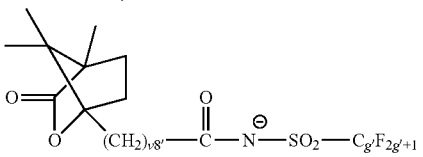
(b1-3-8')

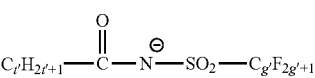
(b1-3-9')

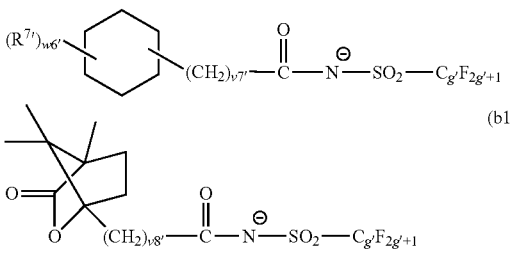
(b1-3-10')

In the formulas, $R^{7\prime}$ represents a substituent; each of w1' to w6' independently represents an integer of 0 to 3; each of v1' to v8' independently represents an integer of 0 to 3; p' represents an integer of 0 to 4; m1' to m2' represents 0 or 1; g' represents an integer of 1 to 4; and t' represents an integer of 3 to 20.

In the formulas above, the substituent for $R^{7\prime}$ is the same as defined above.

If there are two or more of the $R^{7\prime}$ group, as indicated by the values w1' to w3', then the two or more of the $R^{7\prime}$ groups may be the same or different from each other.

Each of w1' to w6' independently represents an integer of 0 to 3, preferably 0 or 1, and most preferably 0.

Each of v1' to v8' independently represents an integer of 0 to 3, and more preferably 0 or 1.

Each p' independently represents an integer of 0 to 4, and preferably 0 to 2.

Each g' independently represents an integer of 1 to 4, preferably 1 or 2, and most preferably 1.

t' represents an integer of 3 to 20, preferably 3 to 15, and more preferably 3 to 12.

—Anion Moiety of Component (B1")

In formula (b1-1"), X represents a hydrocarbon group of 3 to 30 carbon atoms which may have a substituent, and is the same as defined for X in formula (b1-1).

In formula (b1-1), $Q^2$ represents a single bond or an alkylene group.

The alkylene group for $Q^2$ is preferably a linear or branched alkylene group, and preferably has 1 to 12 carbon atoms, more preferably 1 to 5, and most preferably 1 to 3.

Specific examples of alkylene groups include a methylene group [—$CH_2$—]; alkylmethylene groups such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)— and —C($CH_2CH_3$)$_2$—; an ethylene group [—$CH_2CH_2$—]; alkylethylene groups such as —CH($CH_3$)$CH_2$—, —CH($CH_3$)CH($CH_3$)—, —C($CH_3$)$_2CH_2$— and —CH($CH_2CH_3$)$CH_2$—, and —CH($CH_2CH_3$)$CH_2$—; a trimethylene group (n-propylene group) [—$CH_2CH_2CH_2$—]; alkyltrimethylene groups such as —CH($CH_3$)$CH_2CH_2$— and —$CH_2CH(CH_3)CH_2$—; a tetramethylene group [—$CH_2CH_2CH_2CH_2$—]; alkyltetramethylene groups such as —CH($CH_3$)$CH_2CH_2CH_2$— and —$CH_2CH(CH_3)CH_2CH_2$—; and a pentamethylene group [—$CH_2CH_2CH_2CH_2CH_2$—].

In formula (b1-1"), p represents an integer of 1 to 3, preferably 1 or 2, and most preferably 2.

Specific examples of preferable anion moieties for the component (B1") are shown below.

[Chemical Formula 45]

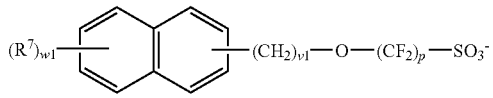
(b1-3-1)

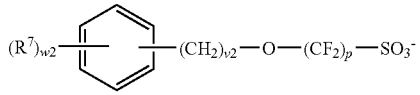
(b1-3-2)

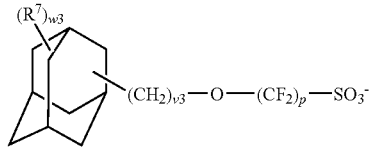
(b1-3-3)

In the formulas, $R^7$ represents a substituent; each of w1 to w3 independently represents an integer of 0 to 3; each of v1 to v3 independently represents an integer of 0 to 5; and p represents an integer of 1 to 3.

In the formulas above, the substituent for $R^7$ is the same as defined above.

If there are two or more of the $R^7$ group, as indicated by the values w1 to w3, then the two or more of the $R^7$ groups may be the same or different from each other.

It is preferable that each of v1 to v3 independently represents an integer of 0 to 3, and preferably 0 or 1.

It is preferable that each of w1 to w3 independently represents an integer of 0 to 2, and most preferably 0.

p is preferably 1 or 2, and most preferably 2.

As the component (B1-0), one type of acid generator may be used alone, or two or more types may be used in combination.

The amount of the component (B1-0), relative to 100 parts by weight of the component (A) is preferably within the range of 0.5 to 60 parts by weight, more preferably within the range of 1 to 40 parts by weight, and most preferably within the range of 3 to 30 parts by weight. When the amount of the component (B1-0) is at least as large as the lower limit of the above-mentioned range, various lithography properties of the resist composition are improved. Further, a resist pattern having an excellent shape can be obtained. On the other hand, when the amount is no more than the upper limit of the above-mentioned range, a uniform solution can be obtained and the storage stability becomes satisfactory.

Moreover, in the resist composition of the present invention, the amount of the component (B1-0) within the component (B) may be 100% by weight. When the component (B1-0) includes the component (B1) and/or the component (B1"), the amount of the component (B1-0) is preferably 40% by weight or more, more preferably 70% by weight or more, and most preferably 100% by weight. When the amount of the component (B1-0) is at least as large as the lower limit of the above-mentioned range, various lithography properties of the resist composition are improved. Further, a resist pattern having an excellent shape can be obtained.

Alternatively, when the component (B1-0) includes the component (B1'), and is used in combination with the component (B2) described later, the amount of the component (B1-0) within the component (B) is preferably 1 to 80% by weight, more preferably 5 to 70% by weight, and most preferably 10 to 60% by weight. When the amount of the component (B1-0) is at least as large as the lower limit of the above-mentioned range, various lithography properties of the resist composition are improved. Further, a resist pattern having an excellent shape can be obtained. On the other hand, when the amount is no more than the upper limit of the above-mentioned range, a good balance can be achieved with the component (B2).

[Component (B2)]

In the resist composition of the present invention, if desired, the component (B) may further include an acid generator other than the component (B1-0) (hereafter, referred to as "component (B2)").

The component (B2) is not particularly limited as long it does not fall under the category of the component (B1-0), and any of the known acid generators used in conventional chemically amplified resist compositions can be used. Examples of these acid generators are numerous, and include onium salt acid generators such as iodonium salts and sulfonium salts; oxime sulfonate acid generators; diazomethane acid generators such as bisalkyl or bisaryl sulfonyl diazomethanes and poly(bis-sulfonyl)diazomethanes; nitrobenzylsulfonate acid generators; iminosulfonate acid generators; and disulfone acid generators.

As an onium salt acid generator, a compound represented by general formula (b-1) or (b-2) shown below can be used.

[Chemical Formula 46]

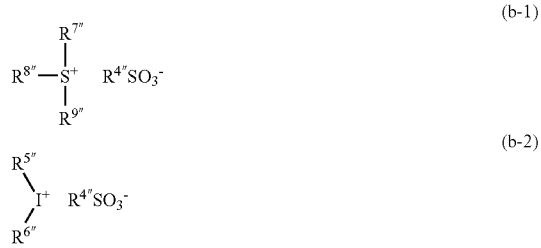

In the formulas, $R^{7"}$ to $R^{9"}$, $R^{5"}$ and $R^{6"}$ each independently represent an aryl group or alkyl group, wherein two of $R^{7"}$ to $R^{9"}$ in formula (b-1) may be bonded to each other to form a ring with the sulfur atom; and $R^{4"}$ represents a linear, branched or cyclic alkyl group or a fluorinated alkyl group, with the provision that at least one of $R^{7"}$ to $R^{9"}$ represents an aryl group, and at least one of $R^{5"}$ and $R^{6"}$ represents an aryl group.

In formula (b-1), $R^{7"}$ to $R^{9"}$ each independently represents an aryl group or an alkyl group. In formula (b-1), two of $R^{7"}$ to $R^{9"}$ may be bonded to each other to form a ring with the sulfur atom.

Further, among $R^{7"}$ to $R^{9"}$, at least one group represents an aryl group. Among $R^{7"}$ to $R^{9"}$, two or more groups are preferably aryl groups, and it is particularly desirable that all of $R^{7"}$ to $R^{9"}$ are aryl groups.

The aryl group for $R^{7"}$ to $R^{9"}$ is not particularly limited. For example, an aryl group having 6 to 20 carbon atoms may be used in which part or all of the hydrogen atoms of the aryl group may or may not be substituted with alkyl groups, alkoxy groups, halogen atoms or hydroxyl groups. The aryl group is preferably an aryl group having 6 to 10 carbon atoms because it can be synthesized at a low cost. Specific examples thereof include a phenyl group and a naphthyl group.

The alkyl group, with which hydrogen atoms of the aryl group may be substituted, is preferably an alkyl group having 1 to 5 carbon atoms, and most preferably a methyl group, an ethyl group, a propyl group, an n-butyl group, or a tert-butyl group.

The alkoxy group, with which hydrogen atoms of the aryl group may be substituted, is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

The alkoxy group, with which hydrogen atoms of the aryl group may be substituted, is preferably an alkoxy group having 1 to 5 carbon atoms, and is most preferably a methoxy group or an ethoxy group.

The halogen atom, with which hydrogen atoms of the aryl group may be substituted, is preferably a fluorine atom.

The alkyl group for $R^{7"}$ to $R^{9"}$ is not particularly limited and includes, for example, a linear, branched or cyclic alkyl group having 1 to 10 carbon atoms. In terms of achieving excellent resolution, the alkyl group preferably has 1 to 5 carbon atoms. Specific examples thereof include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decanyl group, and a methyl group is most preferable because it is excellent in resolution and can be synthesized at a low cost.

It is particularly desirable that each of $R^{7"}$ to $R^{9"}$ independently represent a phenyl group or a naphthyl group.

When two of $R^{7"}$ to $R^{9"}$ in formula (b-1) are bonded to each other to form a ring with the sulfur atom, it is preferable that the two of $R^{7"}$ to $R^{9"}$ form a 3 to 10-membered ring including the sulfur atom, and it is particularly desirable that the two of $R^{7"}$ to $R^{9"}$ form a 5 to 7-membered ring including the sulfur atom.

When two of $R^{7"}$ to $R^{9"}$ in formula (b-1) are bonded to each other to form a ring with the sulfur atom, the remaining one of $R^{7"}$ to $R^{9"}$ is preferably an aryl group. As examples of the aryl group, the same as the above-mentioned aryl groups for $R^{7"}$ to $R^{9"}$ can be given.

$R^{4"}$ represents a linear, branched or cyclic alkyl group or a fluorinated alkyl group.

The linear or branched alkyl group preferably has 1 to 10 carbon atoms, more preferably 1 to 8 carbon atoms, and most preferably 1 to 4 carbon atoms.

The cyclic alkyl group is preferably a cyclic group, as described for $R^{7\prime\prime}$, having 4 to 15 carbon atoms, more preferably 4 to 10 carbon atoms, and most preferably 6 to 10 carbon atoms.

The fluorinated alkyl group preferably has 1 to 10 carbon atoms, more preferably 1 to 8 carbon atoms, and most preferably 1 to 4 carbon atoms.

Further, the fluorination ratio of the fluorinated alkyl group (percentage of fluorine atoms within the alkyl group) is preferably from 10 to 100%, more preferably from 50 to 100%, and it is particularly desirable that all hydrogen atoms are substituted with fluorine atoms (namely, the fluorinated alkyl group is a perfluoroalkyl group) because the acid strength increases.

$R^{4\prime\prime}$ is most preferably a linear or cyclic alkyl group or a fluorinated alkyl group.

In formula (b-2), $R^{5\prime\prime}$ and $R^{6\prime\prime}$ each independently represent an aryl group or alkyl group. At least one of $R^{5\prime\prime}$ and $R^{6\prime\prime}$ represents an aryl group. It is preferable that both of $R^{5\prime\prime}$ and $R^{6\prime\prime}$ represent an aryl group.

As the aryl group for $R^{5\prime\prime}$ and $R^{6\prime\prime}$, the same as the aryl groups for $R^{7\prime\prime}$ to $R^{9\prime\prime}$ can be used.

As the alkyl group for $R^{5\prime\prime}$ and $R^{6\prime\prime}$, the same as the alkyl groups for $R^{7\prime\prime}$ to $R^{9\prime\prime}$ can be used.

It is particularly desirable that both of $R^{5\prime\prime}$ and $R^{6\prime\prime}$ represents a phenyl group.

As $R^{4\prime\prime}$ in formula (b-2), the same groups as those mentioned above for $R^{4\prime\prime}$ in formula (b-1) can be used.

Specific examples of suitable onium salt acid generators represented by formula (b-1) or (b-2) include diphenyliodonium trifluoromethanesulfonate or nonafluorobutanesulfonate; bis(4-tert-butylphenyl)iodonium trifluoromethanesulfonate or nonafluorobutanesulfonate; triphenylsulfonium trifluoromethanesulfonate, heptafluoropropanesulfonate or nonafluorobutanesulfonate; tri(4-methylphenyl)sulfonium trifluoromethanesulfonate, heptafluoropropanesulfonate or nonafluorobutanesulfonate; dimethyl(4-hydroxynaphthyl)sulfonium trifluoromethanesulfonate, heptafluoropropanesulfonate or nonafluorobutanesulfonate; monophenyldimethylsulfonium trifluoromethanesulfonate, heptafluoropropanesulfonate or nonafluorobutanesulfonate; diphenylmonomethylsulfonium trifluoromethanesulfonate, heptafluoropropanesulfonate or nonafluorobutanesulfonate; (4-methylphenyl)diphenylsulfonium trifluoromethanesulfonate, heptafluoropropanesulfonate or nonafluorobutanesulfonate; (4-methoxyphenyl)diphenylsulfonium trifluoromethanesulfonate, heptafluoropropanesulfonate or nonafluorobutanesulfonate; tri(4-tert-butyl)phenylsulfonium trifluoromethanesulfonate, heptafluoropropanesulfonate or nonafluorobutanesulfonate; diphenyl(1-(4-methoxy)naphthyl)sulfonium trifluoromethanesulfonate, heptafluoropropanesulfonate or nonafluorobutanesulfonate; di(1-naphthyl)phenylsulfonium trifluoromethanesulfonate, heptafluoropropanesulfonate or nonafluorobutanesulfonate; 1-phenyltetrahydrothiophenium trifluoromethanesulfonate, heptafluoropropanesulfonate or nonafluorobutanesulfonate; 1-(4-methylphenyl)tetrahydrothiophenium trifluoromethanesulfonate, heptafluoropropanesulfonate or nonafluorobutanesulfonate; 1-(3,5-dimethyl-4-hydroxyphenyl)tetrahydrothiophenium trifluoromethanesulfonate, heptafluoropropanesulfonate or nonafluorobutanesulfonate; 1-(4-methoxynaphthalene-1-yl)tetrahydrothiophenium trifluoromethanesulfonate, heptafluoropropanesulfonate or nonafluorobutanesulfonate; 1-(4-ethoxynaphthalene-1-yl)tetrahydrothiophenium trifluoromethanesulfonate, heptafluoropropanesulfonate or nonafluorobutanesulfonate; 1-(4-n-butoxynaphthalene-1-yl)tetrahydrothiophenium trifluoromethanesulfonate, heptafluoropropanesulfonate or nonafluorobutanesulfonate; 1-phenyltetrahydrothiopyranium trifluoromethanesulfonate, heptafluoropropanesulfonate or nonafluorobutanesulfonate; 1-(4-hydroxyphenyl)tetrahydrothiopyranium trifluoromethanesulfonate, heptafluoropropanesulfonate or nonafluorobutanesulfonate; 1-(3,5-dimethyl-4-hydroxyphenyl)tetrahydrothiopyranium trifluoromethanesulfonate, heptafluoropropanesulfonate or nonafluorobutanesulfonate; and 1-(4-methylphenyl)tetrahydrothiopyranium trifluoromethanesulfonate, heptafluoropropanesulfonate or nonafluorobutanesulfonate.

It is also possible to use onium salts in which the anion moiety of these onium salts are replaced by methanesulfonate, n-propanesulfonate, n-butanesulfonate, or n-octanesulfonate.

Further, onium salt-based acid generators in which the anion moiety in general formula (b-1) or (b-2) is replaced by an anion moiety represented by general formula (b-3) or (b-4) shown below (the cation moiety is the same as (b-1) or (b-2)) may also be used.

[Chemical Formula 47]

In formulas (b-3) and (b-4) above, X" represents an alkylene group of 2 to 6 carbon atoms in which at least one hydrogen atom has been substituted with a fluorine atom; and each of Y" and Z" independently represents an alkyl group of 1 to 10 carbon atoms in which at least one hydrogen atom has been substituted with a fluorine atom.

X" represents a linear or branched alkylene group in which at least one hydrogen atom has been substituted with a fluorine atom, and the alkylene group has 2 to 6 carbon atoms, preferably 3 to 5 carbon atoms, and most preferably 3 carbon atoms.

Each of Y" and Z" independently represents a linear or branched alkyl group in which at least one hydrogen atom has been substituted with a fluorine atom, and the alkyl group has 1 to 10 carbon atoms, preferably 1 to 7 carbon atoms, and most preferably 1 to 3 carbon atoms.

The smaller the number of carbon atoms of the alkylene group for X" or those of the alkyl group for Y" and Z" within the above-mentioned range of the number of carbon atoms, the more the solubility in a resist solvent is improved.

Further, in the alkylene group for X" or the alkyl group for Y" and Z", it is preferable that the number of hydrogen atoms substituted with fluorine atoms is as large as possible because the acid strength increases and the transparency to high energy radiation of 200 nm or less or electron beam is improved.

The fluorination ratio of the alkylene group or alkyl group is preferably from 70 to 100%, more preferably from 90 to 100%, and it is particularly desirable that the alkylene group or alkyl group be a perfluoroalkylene group or perfluoroalkyl group in which all hydrogen atoms are substituted with fluorine atoms.

Furthermore, as an onium salt-based acid generator, a sulfonium salt having a cation moiety represented by general formula (b-5) or (b-6) shown below may be used.

[Chemical Formula 48]

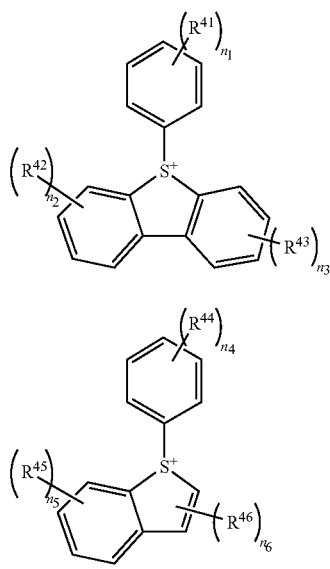

In formulas (b-5) and (b-6) above, each of $R^{41}$ to $R^{46}$ independently represents an alkyl group, an acetyl group, an alkoxy group, a carboxy group, a hydroxyl group or a hydroxyalkyl group; each of $n_1$ to $n_5$ independently represents an integer of 0 to 3; and $n_6$ represents an integer of 0 to 2.

With respect to $R^{41}$ to $R^{46}$, the alkyl group is preferably an alkyl group of 1 to 5 carbon atoms, more preferably a linear or branched alkyl group, and most preferably a methyl group, ethyl group, propyl group, isopropyl group, n-butyl group or tert butyl group.

The alkoxy group is preferably an alkoxy group of 1 to 5 carbon atoms, more preferably a linear or branched alkoxy group, and most preferably a methoxy group or ethoxy group.

The hydroxyalkyl group is preferably the aforementioned alkyl group in which one or more hydrogen atoms have been substituted with hydroxy groups, and examples thereof include a hydroxymethyl group, a hydroxyethyl group and a hydroxypropyl group.

If there are two or more of an individual $R^{41}$ to $R^{46}$ group, as indicated by the corresponding value of $n_1$ to $n_6$, then the two or more of the individual $R^{41}$ to $R^{46}$ group may be the same or different from each other.

$n_1$ is preferably 0 to 2, more preferably 0 or 1, and still more preferably 0.

It is preferable that $n_2$ and $n_3$ each independently represent 0 or 1, and more preferably 0.

$n_4$ is preferably 0 to 2, and more preferably 0 or 1.

$n_5$ is preferably 0 or 1, and more preferably 0.

$n_6$ is preferably 0 or 1, and more preferably 1.

The anion moiety of the sulfonium salt having a cation moiety represented by general formula (b-5) or (b-6) is not particularly limited, and the same anion moieties for onium salt-based acid generators which have been proposed may be used.

Examples of such anion moieties include fluorinated alkylsulfonic acid ions such as anion moieties ($R^{4'''}SO_3^-$) for onium salt-based acid generators represented by general formula (b-1) or (b-2) shown above; and anion moieties represented by general formula (b-3) or (b-4) shown above.

Among these, a fluorinated alkylsulfonate ion is preferable, a fluorinated alkylsulfonate ion of 1 to 4 carbon atoms is more preferable, and a linear perfluoroalkylsulfonate ion of 1 to 4 carbon atoms is particularly desirable. Specific examples thereof include a trifluoromethylsulfonate ion, a heptafluoro-n-propanesulfonate ion and a nonafluoro-n-butanesulfonate ion.

In the present description, an oximesulfonate-based acid generator is a compound having at least one group represented by general formula (B-1) shown below, and has a feature of generating acid by irradiation. Such oximesulfonate acid generators are widely used for a chemically amplified resist composition, and can be appropriately selected.

[Chemical Formula 49]

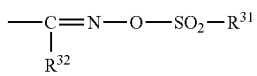

(B-1)

In the formula, each of $R^{31}$ and $R^{32}$ independently represents an organic group.

The organic group for $R^{31}$ and $R^{32}$ refers to a group containing a carbon atom, and may include atoms other than carbon atoms (e.g., a hydrogen atom, an oxygen atom, a nitrogen atom, a sulfur atom, a halogen atom (such as a fluorine atom and a chlorine atom) and the like).

As the organic group for $R^{31}$, a linear, branched, or cyclic alkyl group or aryl group is preferable. The alkyl group or the aryl group may have a substituent. The substituent is not particularly limited, and examples thereof include a fluorine atom and a linear, branched, or cyclic alkyl group having 1 to 6 carbon atoms. The alkyl group or the aryl group "has a substituent" means that part or all of the hydrogen atoms of the alkyl group or the aryl group is substituted with a substituent.

The alkyl group preferably has 1 to 20 carbon atoms, more preferably 1 to 10 carbon atoms, still more preferably 1 to 8 carbon atoms, still more preferably 1 to 6 carbon atoms, and most preferably 1 to 4 carbon atoms. As the alkyl group, a partially or completely halogenated alkyl group (hereinafter, sometimes referred to as a "halogenated alkyl group") is particularly desirable. The "partially halogenated alkyl group" refers to an alkyl group in which part of the hydrogen atoms are substituted with halogen atoms and the "completely halogenated alkyl group" refers to an alkyl group in which all of the hydrogen atoms are substituted with halogen atoms. Examples of halogen atoms include fluorine atoms, chlorine atoms, bromine atoms and iodine atoms, and fluorine atoms are particularly desirable. In other words, the halogenated alkyl group is preferably a fluorinated alkyl group.

The aryl group preferably has 4 to 20 carbon atoms, more preferably 4 to 10 carbon atoms, and most preferably 6 to 10 carbon atoms. As the aryl group, partially or completely halogenated aryl group is particularly desirable. The "partially halogenated aryl group" refers to an aryl group in which some of the hydrogen atoms are substituted with halogen atoms and the "completely halogenated aryl group" refers to an aryl group in which all of hydrogen atoms are substituted with halogen atoms.

As $R^{31}$, an alkyl group of 1 to 4 carbon atoms which has no substituent or a fluorinated alkyl group of 1 to 4 carbon atoms is particularly desirable.

As the organic group for $R^{32}$, a linear, branched, or cyclic alkyl group, aryl group, or cyano group is preferable. Examples of the alkyl group and the aryl group for $R^{32}$ include the same alkyl groups and aryl groups as those described above for $R^{31}$.

As $R^{32}$, a cyano group, an alkyl group of 1 to 8 carbon atoms having no substituent or a fluorinated alkyl group of 1 to 8 carbon atoms is particularly desirable.

Preferred examples of the oxime sulfonate acid generator include compounds represented by general formula (B-2) or (B-3) shown below.

[Chemical Formula 50]

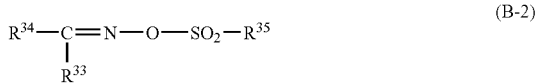

(B-2)

In the formula, $R^{33}$ represents a cyano group, an alkyl group having no substituent or a halogenated alkyl group; $R^{34}$ represents an aryl group; and $R^{35}$ represents an alkyl group having no substituent or a halogenated alkyl group.

[Chemical Formula 51]

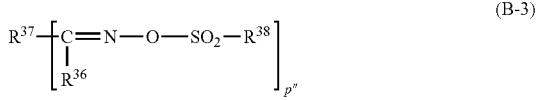

(B-3)

In the formula, $R^{36}$ represents a cyano group, an alkyl group having no substituent or a halogenated alkyl group; $R^{37}$ represents a divalent or trivalent aromatic hydrocarbon group; $R^{38}$ represents an alkyl group having no substituent or a halogenated alkyl group; and p" represents 2 or 3.

In general formula (B-2), the alkyl group having no substituent or the halogenated alkyl group for $R^{33}$ preferably has 1 to 10 carbon atoms, more preferably 1 to 8 carbon atoms, and most preferably 1 to 6 carbon atoms.

As $R^{33}$, a halogenated alkyl group is preferable, and a fluorinated alkyl group is more preferable.

The fluorinated alkyl group for $R^{33}$ preferably has 50% or more of the hydrogen atoms thereof fluorinated, more preferably 70% or more, and most preferably 90% or more.

Examples of the aryl group for $R^{34}$ include groups in which one hydrogen atom has been removed from an aromatic hydrocarbon ring, such as a phenyl group, a biphenyl group, a fluorenyl group, a naphthyl group, an anthryl group, and a phenanthryl group, and heteroaryl groups in which some of the carbon atoms constituting the ring(s) of these groups are substituted with hetero atoms such as an oxygen atom, a sulfur atom, and a nitrogen atom. Of these, a fluorenyl group is preferable.

The aryl group for $R^{34}$ may have a substituent such as an alkyl group of 1 to 10 carbon atoms, a halogenated alkyl group, or an alkoxy group. The alkyl group and halogenated alkyl group as the substituent preferably has 1 to 8 carbon atoms, and more preferably 1 to 4 carbon atoms. Further, the halogenated alkyl group is preferably a fluorinated alkyl group.

The alkyl group having no substituent or the halogenated alkyl group for $R^{35}$ preferably has 1 to 10 carbon atoms, more preferably 1 to 8 carbon atoms, and most preferably 1 to 6 carbon atoms.

As $R^{35}$, a halogenated alkyl group is preferable, and a fluorinated alkyl group is more preferable.

In terms of enhancing the strength of the acid generated, the fluorinated alkyl group for $R^{35}$ preferably has 50% or more of the hydrogen atoms fluorinated, more preferably 70% or more, still more preferably 90% or more. A completely fluorinated alkyl group in which 100% of the hydrogen atoms are substituted with fluorine atoms is particularly desirable.

In general formula (B-3), as the alkyl group having no substituent and the halogenated alkyl group for $R^{36}$, the same alkyl group having no substituent and the halogenated alkyl group described above for $R^{33}$ can be used.

Examples of the divalent or trivalent aromatic hydrocarbon group for $R^{37}$ include groups in which one or two hydrogen atoms have been removed from the aryl group for $R^{34}$.

As the alkyl group having no substituent or the halogenated alkyl group for $R^{38}$, the same one as the alkyl group having no substituent or the halogenated alkyl group for $R^{35}$ can be used.

p" is preferably 2.

Specific examples of suitable oxime sulfonate acid generators include α-(p-toluenesulfonyloxyimino)-benzyl cyanide, α-(p-chlorobenzenesulfonyloxyimino)-benzyl cyanide, α-(4-nitrobenzenesulfonyloxyimino)-benzyl cyanide, α-(4-nitro-2-trifluoromethylbenzenesulfonyloxyimino)-benzyl cyanide, α-(benzenesulfonyloxyimino)-4-chlorobenzyl cyanide, α-(benzenesulfonyloxyimino)-2,4-dichlorobenzyl cyanide, α-(benzenesulfonyloxyimino)-2,6-dichlorobenzyl cyanide, α-(benzenesulfonyloxyimino)-4-methoxybenzyl cyanide, α-(2-chlorobenzenesulfonyloxyimino)-4-methoxybenzyl cyanide, α-(benzenesulfonyloxyimino)-thien-2-yl acetonitrile, α-(4-dodecylbenzenesulfonyloxyimino)benzyl cyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenyl acetonitrile, α-(trifluoromethylsulfonyloxyimino)-1-cyclopentenyl acetonitrile, α-(trifluoromethylsulfonyloxyimino)-cyclohexyl acetonitrile, α-(ethylsulfonyloxyimino)-ethyl acetonitrile, α-(propylsulfonyloxyimino)-propyl acetonitrile, α-(cyclohexylsulfonyloxyimino)-cyclopentyl acetonitrile, α-(cyclohexylsulfonyloxyimino)-cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p-methoxyphenyl acetonitrile, α-(trifluoromethylsulfonyloxyimino)-phenyl acetonitrile, α-(trifluoromethylsulfonyloxyimino)-p-methoxyphenyl acetonitrile, α-(ethylsulfonyloxyimino)-p-methoxyphenyl acetonitrile, α-(propylsulfonyloxyimino)-p-methylphenyl acetonitrile, and α-(methylsulfonyloxyimino)-p-bromophenyl acetonitrile.

Further, oxime sulfonate acid generators disclosed in Japanese Unexamined Patent Application, First Publication No. Hei 9-208554 (Chemical Formulas 18 and 19 shown in paragraphs [0012] to [0014]) and oxime sulfonate acid generators disclosed in WO 2004/074242A2 (Examples 1 to 40 described at pages 65 to 85) may be preferably used.

Furthermore, as preferable examples, the following can be used.

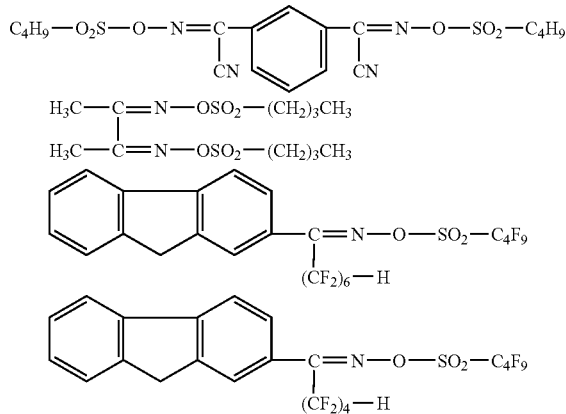

[Chemical Formula 52]

Of the aforementioned diazomethane acid generators, specific examples of suitable bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Further, diazomethane acid generators disclosed in Japanese Unexamined Patent Application, First Publication No. Hei 11-035551, Japanese Unexamined Patent Application, First Publication No. Hei 11-035552 and Japanese Unexamined Patent Application, First Publication No. Hei 11-035573 may be preferably used.

Furthermore, as examples of poly(bis-sulfonyl)diazomethanes, those disclosed in Japanese Unexamined Patent Application, First Publication No. Hei 11-322707, including 1,3-bis(phenylsulfonyldiazomethylsulfonyl)propane, 1,4-bis(phenylsulfonyldiazomethylsulfonyl)butane, 1,6-bis(phenylsulfonyldiazomethylsulfonyl)hexane, 1,10-bis(phenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, and 1,10-bis(cyclohexylsulfonyldiazomethylsulfonyl)decane, may be given.

As the component (B2), one type of acid generator may be used, or two or more types of acid generators may be used in combination.

In the resist composition of the present invention, the amount of the component (B), relative to 100 parts by weight of the component (A) is preferably 0.5 to 60 parts by weight, and more preferably 1 to 40 parts by weight. When the amount of the component (B) is within the above-mentioned range, formation of a resist pattern can be satisfactorily performed. Further, by virtue of the above-mentioned range, a uniform solution can be obtained and the storage stability becomes satisfactory.

<Optional Components>
[Component (D)]

It is preferable that the resist composition of the present invention further includes a nitrogen-containing organic compound (D) (hereafter referred to as the component (D)) as an optional component.

As the component (D), there is no particular limitation as long as it functions as an acid diffusion control agent, i.e., a quencher which traps the acid generated from the component (B) upon exposure. A multitude of these components (D) have already been proposed, and any of these known compounds may be used, although an aliphatic amine, and particularly a secondary aliphatic amine or tertiary aliphatic amine is preferable.

An aliphatic amine is an amine having one or more aliphatic groups, and the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group of no more than 12 carbon atoms (i.e., alkylamines or alkylalcoholamines), and cyclic amines.

Specific examples of alkylamines and alkylalcoholamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine, and tri-n-dodecylamine; and alkyl alcohol amines such as diethanolamine, triethanolamine, diisopropanolamine, triisopropanolamine, di-n-octanolamine, and tri-n-octanolamine. Among these, trialkylamines of 5 to 10 carbon atoms are preferable, and tri-n-pentylamine and tri-n-octylamine are particularly desirable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

These compounds can be used either alone, or in combinations of two or more different compounds.

In the present invention, among the aforementioned examples, it is preferable to use a trialkylamine of 5 to 10 carbon atoms as the component (D).

The component (D) is typically used in an amount within a range from 0.01 to 5.0 parts by weight, relative to 100 parts by weight of the component (A). When the amount of the component (D) is within the above-mentioned range, the shape of the resist pattern and the post exposure stability of the latent image formed by the pattern-wise exposure of the resist layer are improved.

[Component (E)]

Furthermore, in the resist composition of the present invention, for preventing any deterioration in sensitivity, and improving the resist pattern shape and the post exposure stability of the latent image formed by the pattern-wise exposure of the resist layer, at least one compound (E) (hereafter referred to as "component (E)") selected from the group consisting of an organic carboxylic acid, or a phosphorus oxo acid or derivative thereof can be added.

Examples of suitable organic carboxylic acids include acetic acid, malonic acid, citric acid, malic acid, succinic acid, benzoic acid, and salicylic acid.

Examples of phosphorus oxo acids include phosphoric acid, phosphonic acid and phosphinic acid. Among these, phosphonic acid is particularly desirable.

Examples of oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phosphinic acid esters such as phenylphosphinic acid.

As the component (E), one type may be used alone, or two or more types may be used in combination.

As the component (E), an organic carboxylic acid is preferable, and salicylic acid is particularly desirable.

The component (E) is typically used in an amount within a range from 0.01 to 5.0 parts by weight, relative to 100 parts by weight of the component (A).

If desired, other miscible additives can also be added to the resist composition of the present invention. Examples of such miscible additives include additive resins for improving the performance of the resist film, surfactants for improving the applicability, dissolution inhibitors, plasticizers, stabilizers, colorants, halation prevention agents, and dyes.

[Component (S)]

The resist composition of the present invention can be prepared by dissolving the materials for the resist composition in an organic solvent (hereafter, referred to as "component (S)").

The component (S) may be any organic solvent which can dissolve the respective components to give a uniform solution, and one or more kinds of any organic solvent can be appropriately selected from those which have been conventionally known as solvents for a chemically amplified resist.

Examples thereof include lactones such as γ-butyrolactone; ketones such as acetone, methyl ethyl ketone, cyclohexanone, methyl-n-pentyl ketone, methyl isopentyl ketone, and 2-heptanone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; and aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene.

These solvents can be used individually, or in combination as a mixed solvent.

Among these, γ-butyrolactone, propylene glycol monomethyl ether acetate (PGMEA), propylene glycol monomethyl ether (PGME) and ethyl lactate (EL) are preferable.

Further, among the mixed solvents, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, more preferably from 2:8 to 8:2.

Specifically, when EL is mixed as the polar solvent, the PGMEA:EL weight ratio is preferably from 1:9 to 9:1, and more preferably from 2:8 to 8:2. Alternatively, when PGME is mixed as the polar solvent, the PGMEA:PGME is preferably from 1:9 to 9:1, more preferably from 2:8 to 8:2, and still more preferably 3:7 to 7:3.

Further, as the component (S), a mixed solvent of at least one of PGMEA and EL with γ-butyrolactone is also preferable. The mixing ratio (former:latter) of such a mixed solvent is preferably from 70:30 to 95:5.

The amount of the component (S) is not particularly limited, and is appropriately adjusted to a concentration which enables coating of a coating solution to a substrate, depending on the thickness of the coating film. In general, the organic solvent is used in an amount such that the solid content of the resist composition becomes within the range from 1 to 20% by weight, and preferably from 1.5 to 15% by weight.

The resist composition of the present invention described above is a novel composition essentially unknown in the art.

According to the resist composition of the present invention, in the formation of an extremely fine resist pattern, a resist pattern exhibiting an excellent lithography property such as excellent exposure margin (EL margin) and having an excellent pattern shape can be formed. The reason why these effects can be achieved has not been elucidated yet, but is presumed as follows.

In the resist composition of the present invention, the aforementioned component (B1-0), i.e., at least one member selected from the group consisting of an acid generator (B1) including a compound represented by general formula (b 1-1), an acid generator (B1') including a compound represented by general formula (b1-1') and an acid generator (B1") including a compound represented by general formula (b1-1"), is used as an acid generator.

In the anion moiety of the component (B1), the skeleton "—$(CF_2)_p$—$SO_3^-$" has a structure in which a hydrocarbon group of 3 to 30 carbon atoms which may have a substituent (X) is bonded thereto through a divalent linking group containing a carbonyl group (-$Q^1$-). Therefore, the anion moiety of the component (B1) exhibits a high polarity and has a three-dimensionally bulky structure, as compared to a fluorinated alkylsulfonate ion which has conventionally been used as an anion moiety of an onium salt-based acid generator. By virtue of the interaction between molecules due to such high polarity and the three-dimensionally bulky structure, it is presumed that diffusion of the anion moiety within a resist film can be chemically and physically suppressed, as compared to a conventional anion moiety of an acid generator such as nonafluorobutanesulfonate. Hence, it is presumed that by using the component (B1), acid generated in exposed regions can be suppressed from diffusing into unexposed regions, and as a result, the difference in alkali solubility between unexposed portions and exposed portions (i.e., dissolution contrast) can be improved, thereby improving the resist pattern shape or the exposure margin (EL margin).

The "EL margin" is the range of the exposure dose in which a resist pattern can be formed with a size within a predetermined range of variation from a target size, when exposure is conducted by changing the exposure dose, i.e., the range of the exposure dose in which a resist pattern faithful to the mask pattern can be formed. The larger the EL margin, the smaller the variation in the pattern size depending on the change in the exposure dose, thereby resulting in favorable improvement in the process margin.

Further, the compound represented by general formula (b1-1') (i.e., the component (B1')) has an anion moiety in which the skeleton "$Y^{11}$—$SO_2$—" has "$X^{10}$-$Q^3$-$Y^{10}$—$N^-$—" bonded thereto.

Therefore, the compound (B1') exhibits high lipophilicity and has a three-dimensionally bulky structure, as compared to a fluorinated alkylsulfonate ion which has conventionally been used as an anion moiety for an acid generator. By virtue of the three-dimensionally bulky structure, it is presumed that diffusion of the anion moiety (acid) within a resist film can be chemically and physically suppressed, as compared to a conventional anion moiety of an acid generator such as nonafluorobutanesulfonate. Further, by virtue of the high lipophilicity, it is presumed that uniformity within a resist film is improved. Therefore, in the resist composition of the present invention, acid generated in exposed regions can be suppressed from diffusing to the unexposed regions, and as a result, a satisfactory level in the difference in alkali solubility between unexposed portions and exposed portions (i.e., dissolution contrast) can be achieved. Thus, according to the resist composition of the present invention, it is presumed that the resist pattern shape or the exposure margin (EL margin) can be improved.

Further, in the anion moiety of the component (B1"), the skeleton "—O—$(CF_2)_p$—$SO_3^-$" has a structure in which a hydrocarbon group of 3 to 30 carbon atoms which may have a substituent (X) is bonded thereto through a single bond or an alkylene group (-$Q^2$-). Therefore, the anion moiety of the component (B1") has a three-dimensionally bulky structure, as compared to a fluorinated alkylsulfonate ion which has conventionally been used as an anion moiety of an onium salt-based acid generator. By virtue of the three-dimensionally bulky structure, it is presumed that diffusion of the anion moiety (acid) within a resist film can be chemically and physically suppressed, as compared to a conventional anion moiety of an acid generator such as nonafluorobutanesulfonate. Hence, it is presumed that by using the component (B1"), acid generated in exposed regions can be suppressed from diffusing into unexposed regions, and as a result, the difference in alkali solubility between unexposed portions and exposed portions (i.e., dissolution contrast) can be improved, thereby improving the resist pattern shape. Furthermore, even when the exposure dose is fluctuated, sufficient amount of acid for dissociating the acid dissociable, dissolution inhibiting group within, for example, the aforementioned structural unit (a1) can be generated, thereby improving the exposure margin (EL margin).

In addition, according to the resist composition of the present invention, the shape of the resist pattern formed is improved, e.g., the circularity and the uniformity of a hole pattern, line width roughness (LWR) and line edge roughness (LER) of a line pattern. The reason for this has not been elucidated yet, but is presumed to be the same as the aforementioned reason for the improvement in the EL margin. "LWR" refers to the heterogeneity of the line width of a line pattern, and "LER" refers to the heterogeneity in the side wall of a line pattern, and improvement in these characteristics becomes more important as the pattern becomes smaller.

<<Method of Forming a Resist Pattern>>

The method of forming a resist pattern according to the second aspect of the present invention includes: using a resist composition according to the first aspect of the present invention to form a resist film on a substrate; conducting exposure of the resist film; and alkali-developing the resist film to form a resist pattern.

More specifically, the method for forming a resist pattern according to the present invention can be performed, for example, as follows.

Firstly, a resist composition of the present invention is applied onto a substrate using a spinner or the like, and a prebake (post applied bake (PAB)) is conducted under temperature conditions of 80 to 150° C. for 40 to 120 seconds, preferably 60 to 90 seconds to form a resist film. Then, for example, using an ArF exposure apparatus or the like, the resist film is selectively exposed to an ArF excimer laser beam through a desired mask pattern, followed by post exposure bake (PEB) under temperature conditions of 80 to 150° C. for 40 to 120 seconds, preferably 60 to 90 seconds. Subsequently, alkali developing is conducted using an alkali developing solution such as a 0.1 to 10% by weight aqueous solution of tetramethylammonium hydroxide (TMAH), preferably followed by rinsing with pure water, and drying. If desired, bake treatment (post bake) can be conducted following the alkali developing. In this manner, a resist pattern that is faithful to the mask pattern can be obtained.

The substrate is not specifically limited and a conventionally known substrate can be used. For example, substrates for electronic components, and such substrates having wiring patterns formed thereon can be used. Specific examples of the material of the substrate include metals such as silicon wafer, copper, chromium, iron and aluminum; and glass Suitable materials for the wiring pattern include copper, aluminum, nickel, and gold.

Further, as the substrate, any one of the above-mentioned substrates provided with an inorganic and/or organic film on the surface thereof may be used. As the inorganic film, an inorganic antireflection film (inorganic BARC) can be used. As the organic film, an organic antireflection film (organic BARC) can be used.

The wavelength to be used for exposure is not particularly limited and the exposure can be conducted using radiation such as ArF excimer laser, KrF excimer laser, $F_2$ excimer laser, extreme ultraviolet rays (EUV), vacuum ultraviolet rays (VUV), electron beam (EB), X-rays, and soft X-rays.

The resist composition of the present invention is effective to KrF excimer laser, ArF excimer laser, EB and EUV, and particularly effective to ArF excimer laser.

The exposure of the resist film can be either a general exposure (dry exposure) conducted in air or an inert gas such as nitrogen, or immersion exposure (immersion lithography).

In immersion lithography, exposure (immersion exposure) is conducted in a state where the region between the lens and the resist layer formed on a wafer (which was conventionally filled with air or an inert gas such as nitrogen) is filled with a solvent (a immersion medium) that has a larger refractive index than the refractive index of air.

More specifically, in immersion lithography, the region between the resist film formed in the above-described manner and lens at the lowermost portion of the exposure apparatus is filled with a solvent (a immersion medium) that has a larger refractive index than the refractive index of air, and in this state, the resist film is subjected to exposure (immersion exposure) through a desired mask pattern.

The immersion medium preferably exhibits a refractive index larger than the refractive index of air but smaller than the refractive index of the resist film to be subjected to immersion exposure. The refractive index of the immersion medium is not particularly limited as long at it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point within a range from 70 to 180° C. and preferably from 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point 102° C.), and an example of a suitable perfluoroalkylamine compound is perfluorotributylamine (boiling point 174° C.).

<<Compound>>

The compound according to a third aspect of the present invention is a compound including at least one member selected from the group consisting of a compound (B1) represented by general formula (b 1-1) shown below, a compound (B1') represented by general formula (b1-1') shown below and a compound (B1") represented by general formula (b1-1") shown below. The compound is the same as the component (B1-0) included in the component (B) of the resist composition according to the first aspect of the present invention.

[Chemical Formula 53]

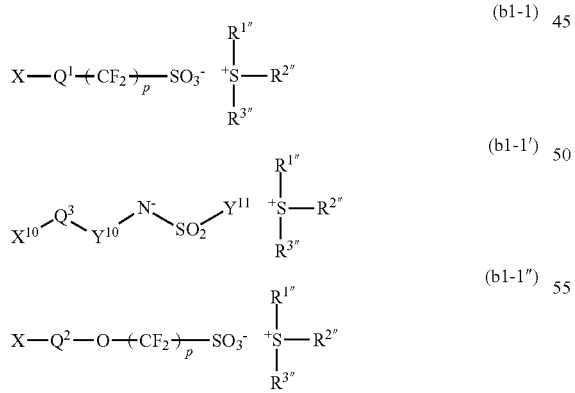

(b1-1)

(b1-1')

(b1-1")

In the formulas, each of $R^{1\prime\prime}$ to $R^{3\prime\prime}$ independently represents an aryl group which may have a substituent or an alkyl group which may have a substituent, with the provision that at least one of $R^{1\prime\prime}$ to $R^{3\prime\prime}$ represents a substituted aryl group having part of the hydrogen atoms substituted with a group represented by general formula (b1-1-0) shown below, and two of $R^{1\prime\prime}$ to $R^{3\prime\prime}$ may be bonded to each other to form a ring with the sulfur atom; X represents a hydrocarbon group of 3 to 30 carbon atoms which may have a substituent; $Q^1$ represents a divalent linking group containing a carbonyl group; p represents an integer of 1 to 3; $X^{10}$ represents a hydrocarbon group of 1 to 30 carbon atoms which may have a substituent; $Q^3$ represents a single bond or a divalent linking group; $Y^{10}$ represents —C(=O)— or —$SO_2$—; $Y^{11}$ represents an alkyl group of 1 to 10 carbon atoms which may have a substituent or a fluorinated alkyl group which may have a substituent: and $Q^2$ represents a single bond or an alkylene group.

[Chemical Formula 54]

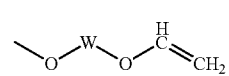

(b1-1-0)

In formula (b1-1-0), W represents a linear or branched alkylene group of 2 to 10 carbon atoms.

The explanation of the compound of the present invention is the same as the explanation of the aforementioned component (B1-0).

(Production Method of Compound)

Each of the compound (B1) represented by general formula (b 1-1) (component (B1)), the compound (B1') represented by general formula (b1-1) (component (B1')), and the compound (B1") represented by general formula (b1-1") (component (B1")) can be produced by a conventional method.

(Production Method of Compound (B1))

As the compound (B1), a compound having an anion represented by general formula (b1-3-10) as the anion moiety, a compound having an anion represented by general formula (b1-3-20) as the anion moiety, a compound having an anion represented by general formula (b1-3-31) as the anion moiety, or a compound having an anion represented by general formula (b1-3-41) as the anion moiety can be produced as follows.

[Production Method of Compound Having an Anion Moiety Represented by General Formula (b1-3-10)]

A compound (b1-1-1) having an anion moiety represented by general formula (b1-3-10) can be produced by reacting a compound (b0-1) represented by general formula (b0-1) shown below with a compound (b0-2) represented by general formula (b0-2) shown below.

[Chemical Formula 55]

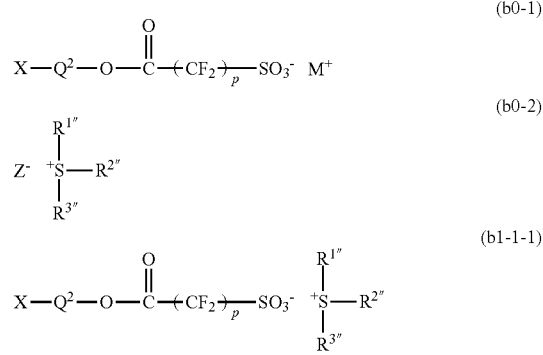

(b0-1)

(b0-2)

(b1-1-1)

In formulas (b0-1) and (b0-2), X, $Q^2$ and p are respectively the same as defined for X, $Q^2$ and p in general formula (b1-3-10).

In formula (b0-2), $R^{1'''}$ to $R^{3'''}$ are respectively the same as defined for $R^{1'''}$ to $R^{3'''}$ in general formula (b1-1).

$M^+$ represents an alkali metal ion, or an ammonium ion which may have a substituent.

Examples of alkali metal ions include a sodium ion, a lithium ion and a potassium ion, and a sodium ion or a lithium ion is preferable.

As an example of the ammonium ion which may have a substituent, a group represented by general formula (b1-3-2) shown below can be given.

[Chemical Formula 56]

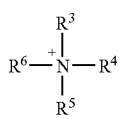

(b1-2-2)

In the formula, each of $R^3$ to $R^6$ independently represents a hydrogen atom or a hydrocarbon group which may have a substituent, with the provision that at least one of $R^3$ to $R^6$ represents a hydrocarbon group; and at least two of $R^3$ to $R^6$ may be mutually bonded to form a ring.

In formula (b1-2-2), each of $R^3$ to $R^6$ independently represents a hydrogen atom or a hydrocarbon group which may have a substituent, provided that at least one of $R^3$ to $R^6$ represents a hydrocarbon group.

As the hydrocarbon group for $R^3$ to $R^6$, the same groups as those described above for X can be mentioned.

The hydrocarbon group may be either an aliphatic hydrocarbon group or an aromatic hydrocarbon group. When the hydrocarbon group is an aliphatic hydrocarbon group, it is particularly desirable that the hydrocarbon group is an alkyl group of 1 to 12 carbon atoms which may have a substituent.

At least one of $R^3$ to $R^6$ is a hydrocarbon group, and it is preferable that two or three groups are hydrocarbon groups.

At least two of $R^3$ to $R^6$ may be mutually bonded to form a ring. For example, two of $R^3$ to $R^6$ may be bonded to form a ring, three of $R^3$ to $R^6$ may be bonded to form a ring, or two of $R^3$ to $R^6$ may be bonded to form a ring, and the remaining two may be bonded to form another ring.

The ring which is formed by at least two of $R^3$ to $R^6$ bonded together with the nitrogen atom (i.e., the hetero ring containing nitrogen as a hetero atom) may be either an aliphatic hetero ring, or an aromatic hetero ring. Further, the hetero ring may be either a monocyclic group or a polycyclic group.

Specific examples of the ammonium ion represented by general formula (b1-3-2) include ammonium ions derived from an amine.

Here, an "ammonium ion derived from an amine" refers to an amine having a hydrogen atom bonded to the nitrogen atom to become a cation, and a tertiary ammonium ion in which a substituent has been bonded to the nitrogen atom of an amine.

The amine from which the ammonium ion is derived may be either an aliphatic amine or an aromatic amine.

As the aliphatic amine, an amine in which at least one hydrogen atom of ammonia ($NH_3$) has been substituted with an alkyl group or hydroxyalkyl group of no more than 12 carbon atoms (i.e., alkylamines or alkylalcoholamines), or a cyclic amine is particularly desirable.

Specific examples of alkylamines and alkylalcoholamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine, and tri-n-dodecylamine; and alkyl alcohol amines such as diethanolamine, triethanolamine, diisopropanolamine, triisopropanolamine, di-n-octanolamine, and tri-n-octanolamine.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Examples of aromatic amines include aniline, pyridine, 4-dimethylaminopyridine (DMAP), pyrrole, indole, pyrazole, and imidazole.

Examples of the tertiary ammonium ion include a tetramethylammonium ion, a tetraethylammonium ion and a tetrabutylammonium ion.

As the ammonium ion represented by general formula (b1-2-2), a group in which at least one of $R^3$ to $R^6$ is an alkyl group and at least one is a hydrogen atom is particularly desirable.

Especially, a group in which three of $R^3$ to $R^6$ are alkyl groups, and the remaining one is a hydrogen atom (i.e., a trialkylammonium ion), or a group in which two of $R^3$ to $R^6$ are alkyl groups, and the remaining two are hydrogen atoms (i.e., dialkylammonium ion) is preferable.

It is preferable that each of the alkyl groups within the trialkylammonium ion or the dialkylammonium ion independently has 1 to 10 carbon atoms, more preferably 1 to 8, and most preferably 1 to 5. Specific examples include a methyl group, an ethyl group, a propyl group, a butyl group, a pentyl group, a hexyl group, a heptyl group, an octyl group, a nonyl group and a decanyl group. Among these, an ethyl group is particularly desirable.

In formula (b0-2), $Z^-$ represents a non-nucleophilic ion.

Examples of non-nucleophilic ions include a halogen ion such as a bromine ion or a chlorine ion; an ion capable of forming an acid exhibiting a lower acidity than the compound (b0-1); $BF_4^-$, $AsF_6^-$, $SbF_6^-$, $PF_6^-$ and $ClO_4^-$.

Examples of ions for $Z^-$ which are capable of forming an acid exhibiting a lower acidity than the compound (b0-1) include sulfonic acid ions such as a p-toluenesulfonate ion, a methanesulfonate ion, and a benzenesulfonate ion.

As the compound (b0-1) and the compound (b0-2), commercially available compounds may be used, or the compounds may be synthesized by a conventional method.

The method of producing the compound (b0-1) is not particularly limited. For example, a compound represented by general formula (b1-1-11) shown below can be dissolved in a solvent such a tetrahydrofuran or water, and the resulting solution can be subjected to a reaction in an aqueous solution of an ammonium compound or an alkali metal hydroxide such as sodium hydroxide or lithium hydroxide, thereby obtaining a compound represented by general formula (b1-1-12) shown below. Then, the compound represented by general formula (b1-1-12) can be subjected to a dehydration/condensation reaction with an alcohol represented by general formula (b1-1-13) shown below in an organic solvent such as benzene or dichloroethane in the presence of an acidic catalyst, thereby obtaining a compound represented by general formula (b0-1).

[Chemical Formula 57]

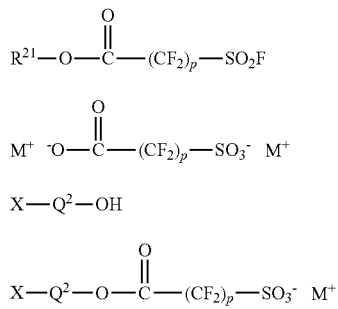

In the formulas, $R^{21}$ represents an alkyl group of 1 to 5 carbon atoms; and X, $Q^2$, p and $M^+$ are respectively the same as X, $Q^2$, p and $M^+$ defined in general formula (b0-1).

The aforementioned compound (b0-2) can be produced as follows.

Firstly, for example, a compound represented by general formula (b1-15-01) shown below and a compound represented by general formula (b1-15-02) shown below are added to and reacted in a solution of an organic acid $H^+B^-$ ($B^-$ represents an anion moiety of an organic acid, such as a methanesulfonate ion). Then, pure water and an organic solvent (e.g., dichloromethane, tetrahydrofuran, or the like) are added thereto, and the organic phase is collected. From the organic phase, a compound represented by general formula (b1-15-03) is obtained.

[Chemical Formula 58]

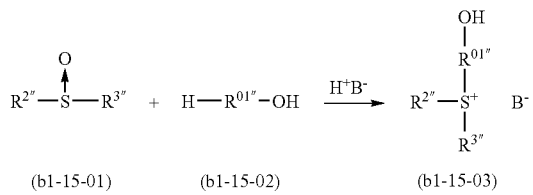

In the formulas, $R^{2\prime\prime}$ and $R^{3\prime\prime}$ are the same as defined above; $R^{01\prime\prime}$ represents a group in which one hydrogen atom has been removed from the $R^{1\prime\prime}$ group in general formula (b1-1), provided that the hydrogen atom has not been removed from a substituent; and $B^-$ represents an anion moiety of an organic acid.

In the formulas, $R^{2\prime\prime}$ and $R^{3\prime\prime}$ are respectively the same as defined for $R^{2\prime\prime}$ and $R^{3\prime\prime}$ in general formula (b1-1).

$R^{01\prime\prime}$ represents a group in which one hydrogen atom has been removed from the $R^{1\prime\prime}$ group in general formula (b1-1), provided that the hydrogen atom has not been removed from a substituent. For example, when $R^{1\prime\prime}$ represents an aryl group, $R^{01\prime\prime}$ represents an arylene group. Alternatively, when $R^{1\prime\prime}$ represents an alkyl group, $R^{01\prime\prime}$ represents an alkylene group.

Subsequently, the compound represented by general formula (b1-15-03) is added to an organic solvent (e.g., acetonitrile, dichloromethane, tetrahydrofuran, or the like), followed by stirring. Then, in the presence of a basic catalyst such as potassium carbonate, a compound represented by general formula (b1-0-1) shown below is added thereto and reacted, followed by liquid separation and washing with water. From the resulting organic phase, a compound represented by general formula (b1-3-04) shown below is obtained.

[Chemical Formula 59]

In the formulas, $R^{2\prime\prime}$, $R^{3\prime\prime}$, $R^{01\prime\prime}$, $B^-$ and W are the same as defined above; Ha represents a halogen atom; and $Ha^-$ represents a halogen ion.

In the formulas, $R^{2\prime\prime}$, $R^{3\prime\prime}$, $R^{01\prime\prime}$ and $B^-$ are the same as defined above, and W is the same as defined for W in general formula (b1-1-0).

Ha represents a halogen atom, and $Ha^-$ represents a halogen ion.

Further, in general formula (b1-15-04), the group represented by the formula "—$R^{01\prime\prime}$—O—W—O—CH=CH$_2$" is the same as the "—$R^{1\prime\prime\prime}$" group in which one hydrogen has been substituted by the group represented by general formula (b1-1-0).

The compound represented by general formula (b1-15-04) is a mixture of a compound having an organic acid ($B^-$) as the anion moiety and a compound having a halogen ion ($Ha^-$) as the anion moiety.

The reaction between the compound (b0-1) and the compound (b0-2) can be effected by dissolving the compounds in a solvent such as water, dichloromethane, acetonitrile, methanol, chloroform or methylene chloride, followed by stirring.

The reaction temperature is preferably 0 to 150° C., and more preferably 0 to 100° C. The reaction time varies depending on the reactivity of the compound (b0-1) and the compound (b0-2), the reaction temperature, and the like. However, in general, the reaction temperature is preferably 0.5 to 10 hours, and more preferably 1 to 5 hours.

In general, the amount of the compound (b0-2) used in the reaction is preferably 0.5 to 2 moles, per 1 mole of the compound (b0-1).

After the reaction, the compound (b1-1-1) within the reaction mixture may be separated and purified. The separation and purification can be conducted by a conventional method. For example, any one of concentration, solvent extraction, distillation, crystallization, recrystallization and chromatography can be used alone, or two or more of these methods may be used in combination.

[Production Method of Compound Having an Anion Moiety Represented by General Formula (b1-3-20)]

A compound (b1-1-2) having an anion moiety represented by general formula (b1-3-20) can be produced by reacting a compound (b0-01) represented by general formula (b0-01) shown below with a compound (b0-02) represented by general formula (b0-02) shown below.

In the formula, examples of the non-nucleophilic ion represented by $Z'^-$ include a halogen ion such as a bromine ion or a chlorine ion; an ion capable of forming an acid exhibiting a lower acidity than the compound (b0-01); $BF_4^-$, $AsF_6^-$, $SbF_6^-$, $PF_6^-$ and $ClO_4^-$.

Examples of ions for $Z'^-$ which are capable of forming an acid exhibiting a lower acidity than the compound (b0-01) include sulfonic acid ions such as a p-toluenesulfonate ion, a methanesulfonate ion, and a benzenesulfonate ion.

[Chemical Formula 60]

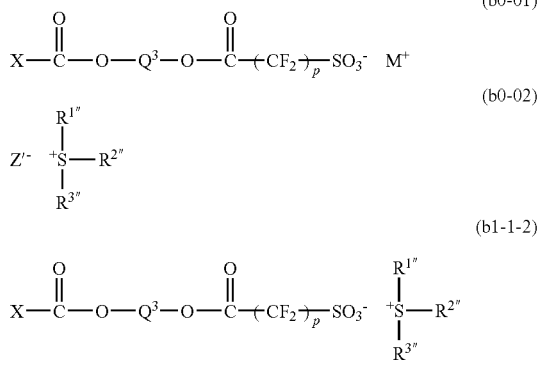

In the formulas, X, $Q^3$, p and $M^+$ are the same as defined above; $Z'^-$ represents a non-nucleophilic ion. $R^{1''}$ to $R^{3''}$ are respectively the same as defined for $R^{1''}$ to $R^{3''}$ in general formula (b1-1).

The aforementioned compound (b0-01) can be synthesized, for example, by reacting a compound (1-3) represented by general formula (1-3) shown below with a compound (2-1) represented by general formula (2-1) shown below.

[Chemical Formula 61]

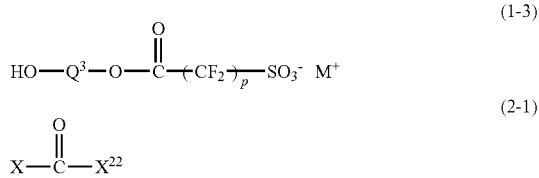

In the formulas, X, $Q^3$, p and $M^+$ are the same as defined above, and $X^{22}$ represents a halogen atom.

Examples of the halogen atom represented by $X^{22}$ include a bromine atom, a chlorine atom, an iodine atom and a fluorine atom. In terms of reactivity, a bromine atom or a chlorine atom is preferable, and a chlorine atom is particularly desirable.

As the compounds (1-3) and (2-1), commercially available compounds may be used, or the compounds may be synthesized.

A preferable method of synthesizing the compound (1-3) includes reacting a compound (1-1) represented by general formula (1-1) shown below with a compound (1-2) represented by general formula (1-2) shown below, thereby obtaining a compound (1-3).

[Chemical Formula 62]

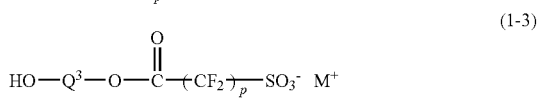

In the formulas, $Q^3$, p and $M^+$ are the same as defined above; and $R^9$ represents an aliphatic group which may have an aromatic group as a substituent.

In formula (1-1), $R^9$ represents an aliphatic group which may have an aromatic group as a substituent.

The aliphatic group may be either a saturated aliphatic group, or an unsaturated aliphatic group. Further, the aliphatic group may be linear, branched or cyclic, or a combination thereof.

The aliphatic group may be either an aliphatic hydrocarbon group consisting of carbon atoms and hydrogen atoms, a group in which part of the carbon atoms constituting the aforementioned aliphatic hydrocarbon group have been substituted with a hetero atom-containing substituent, or a group in which part or all of the hydrogen atoms constituting the aforementioned aliphatic hydrocarbon group have been substituted with a hetero atom-containing substituent.

As the hetero atom, there is no particular limitation as long as it is an atom other than a carbon atom and a hydrogen atom. Examples of halogen atoms include a fluorine atom, a chlorine atom, an iodine atom and a bromine atom.

The hetero atom-containing substituent may consist of a hetero atom, or may be a group containing a group or atom other than a hetero atom.

Specific examples of the substituent group for substituting part of the carbon atoms include —O—, —C(=O)—O—, —C(=O)—, —O—C(=O)—, —C(=O)—NH—, —NH— (the H may be replaced with a substituent such as an alkyl group or an acyl group), —S—, —S(=O)$_2$— and —S(=O)$_2$—O—. When the aliphatic hydrocarbon group contains a cyclic group, the aliphatic hydrocarbon group may contain these substituent groups in the ring structure of the cyclic group.

Examples of the substituent group for substituting part or all of the hydrogen atoms include an alkoxy group, a halogen atom, a halogenated alkyl group, a hydroxyl group, an oxygen atom (=O), —COOR$^{96}$, —OC(=O)R$^{97}$ and a cyano group.

The aforementioned alkoxy group is preferably an alkoxy group having 1 to 5 carbon atoms, more preferably a methoxy group, ethoxy group, n-propoxy group, iso-propoxy group, n-butoxy group or tert-butoxy group, and most preferably a methoxy group or an ethoxy group.

Examples of the aforementioned halogen atom include a fluorine atom, a chlorine atom, a bromine atom and an iodine atom, and a fluorine atom is preferable.

Example of the aforementioned halogenated alkyl group includes a group in which part or all of the hydrogen atoms within an alkyl group of 1 to 5 carbon atoms (e.g., a methyl group, an ethyl group, a propyl group, an n-butyl group or a tert-butyl group) have been substituted with the aforementioned halogen atoms.

Each of $R^{96}$ and $R^{97}$ independently represents a hydrogen atom or a linear, branched or cyclic alkyl group of 1 to 15 carbon atoms.

When the alkyl group for $R^{96}$ and $R^{97}$ is a linear or branched alkyl group, it preferably has 1 to 10 carbon atoms, more preferably 1 to 5, and still more preferably 1 or 2. Specific examples of alkyl groups include the same groups as those for the linear or branched monovalent saturated hydrocarbon group described below.

When the alkyl group for $R^{96}$ and $R^{97}$ is a cyclic group, it may be either a monocyclic group or a polycyclic group. The cyclic group preferably has 3 to 15 carbon atoms, more preferably 4 to 12, and still more preferably 5 to 10. Specific examples of cyclic groups include the same groups as those for the cyclic monovalent saturated hydrocarbon group described below.

As the aliphatic hydrocarbon group, a linear or branched saturated hydrocarbon group of 1 to 30 carbon atoms, a linear or branched unsaturated hydrocarbon group of 2 to 10 carbon atoms, or a cyclic aliphatic hydrocarbon group (aliphatic cyclic group) of 3 to 30 carbon atoms is preferable.

The linear saturated hydrocarbon group preferably has 1 to 20 carbon atoms, more preferably 1 to 15, and most preferably 1 to 10. Specific examples include a methyl group, an ethyl group, a propyl group, a butyl group, a pentyl group, a hexyl group, a heptyl group, an octyl group, a nonyl group, a decanyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched saturated hydrocarbon group preferably has 3 to 20 carbon atoms, more preferably 3 to 15, and most preferably 3 to 10. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

The unsaturated hydrocarbon group preferably has 2 to 5 carbon atoms, more preferably 2 to 4, and most preferably 3. Examples of linear monovalent unsaturated hydrocarbon groups include a vinyl group, a propenyl group (an allyl group) and a butynyl group. Examples of branched monovalent unsaturated hydrocarbon groups include a 1-methylpropenyl group and a 2-methylpropenyl group.

Among the above-mentioned examples, as the unsaturated hydrocarbon group, a propenyl group is particularly desirable.

The aliphatic cyclic group may be either a monocyclic group or a polycyclic group. The aliphatic cyclic group preferably has 3 to 30 carbon atoms, more preferably 5 to 30, still more preferably 5 to 20, still more preferably 6 to 15, and most preferably 6 to 12. As the aliphatic cyclic group, a group in which one or more hydrogen atoms have been removed from a monocycloalkane or a polycycloalkane such as a bicycloalkane, tricycloalkane or tetracycloalkane can be used. Specific examples include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

The aliphatic group for $R^9$ in formula (1-1) may have an aromatic group as a substituent.

Examples of aromatic groups include an aryl group which is an aromatic hydrocarbon ring having one hydrogen atom removed therefrom, such as a phenyl group, a biphenyl group, a fluorenyl group, a naphthyl group, an anthryl group or a phenanthryl group; and a heteroaryl group in which a part of the carbon atoms constituting the aforementioned aryl group has been substituted with a hetero atom such as an oxygen atom, a sulfur atom or a nitrogen atom.

The aromatic group may have a substituent such as an alkyl group of 1 to 10 carbon atoms, a halogenated alkyl group, an alkoxy group, a hydroxyl group or a halogen atom. The alkyl group or halogenated alkyl group as a substituent preferably has 1 to 8 carbon atoms, and more preferably 1 to 4 carbon atoms. Further, the halogenated alkyl group is preferably a fluorinated alkyl group. Examples halogen atoms include a fluorine atom, a chlorine atom, an iodine atom and a bromine atom, and a fluorine atom is preferable.

If the $R^9$ group in the compound (1-1) represents an aromatic group, i.e., when the oxygen atom adjacent to the $R^9$ group is directly bonded to an aromatic ring without interposing an aliphatic group, the reaction between the compound (1-1) and the compound (1-2) does not proceed, such that the compound (1-3) cannot be obtained.

As the compounds (1-1) and (1-2), commercially available compounds may be used, or the compounds may be synthesized by a conventional method.

For example, a method including heating a compound (0-1) represented by general formula (0-1) shown below in the presence of an alkali, and neutralizing the resultant, thereby obtaining a compound (0-2) represented by general formula (0-2) shown below (hereafter, this step is referred to as "salt-formation step", and heating the compound (0-2) in the presence of an acid having an acid strength stronger than that of the compound (1-2), thereby obtaining the compound (1-2) (hereafter, this step is referred to as "carboxylic acid-generation step".

[Chemical Formula 63]

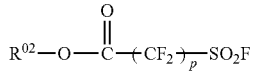

(0-1)

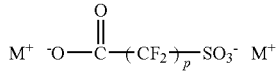

(0-2)

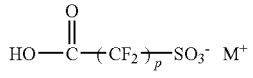

(1-2)

In the formulas, $R^{02}$ represents an alkyl group; and p and $M^+$ are the same as defined above.

As the alkyl group for $R^{02}$, a linear or branched alkyl group is preferable, and specific examples include a methyl group, an ethyl group, a propyl group, an isopropyl group, an n-butyl group, an isobutyl group, a tert-butyl group, a pentyl group, an isopentyl group and a neopentyl group.

Among these, an alkyl group of 1 to 4 carbon atoms is preferable, and a methyl group is particularly desirable.

As the compound (0-1), a commercially available compound can be used.

The salt-formation step can be performed, for example, by dissolving the compound (0-1) in a solvent, and adding an alkali to the resulting solution, followed by heating.

As the solvent, any solvent which is capable of dissolving the compound (0-1) can be used. Examples of such a solvent include water and tetrahydrofuran.

As the alkali, an alkali corresponding to M in formula (0-2) is used. Examples of such an alkali include alkali metal hydroxides such as sodium hydroxide, potassium hydroxide and lithium hydroxide.

The amount of the alkali used is preferably 1 to 5 moles, more preferably 2 to 4 moles, per 1 mole of the compound (0-1).

The heating temperature is preferably 20 to 120° C., and more preferably about 50 to 100° C. The heating time depends on the heating temperature, but in general, the heating time is preferably 0.5 to 12 hours, and more preferably 1 to 5 hours.

The neutralization following the heating can be conducted by adding an acid such as hydrochloric acid, sulfuric acid or p-toluenesulfonic acid to the reaction mixture following the heating.

It is preferable to conduct the neutralization so that the pH of the reaction mixture (25° C.) after addition of an acid falls within the range of 6 to 8. Further, the temperature of the reaction mixture during the neutralization is preferably 20 to 30° C., and more preferably 23 to 27° C.

After the reaction, the compound (0-2) within the reaction mixture may be separated and purified. The separation and purification can be conducted by a conventional method. For example, any one of concentration, solvent extraction, distillation, crystallization, recrystallization and chromatography can be used alone, or two or more of these methods may be used in combination.

In the carboxylic acid-generation step, the compound (0-2) obtained in the salt-formation step is heated in the presence of an acid having an acid strength stronger than that of the compound (1-2), thereby obtaining the compound (1-2).

"An acid having an acid strength stronger than that of the compound (1-2)" (hereafter, frequently referred to simply as "strong acid") refers to an acid having a pKa value (25° C.) smaller than that of —COOH within the compound (1-2). By using such a strong acid, —COO$^-$M$^+$ within the compound (0-2) can be converted into —COOH, thereby obtaining the compound (1-2).

The strong acid can be appropriately selected from any conventional acids which exhibit a pKa value smaller than that of —COOH within the compound (1-2). The pKa value of —COOH within the compound (1-2) can be determined by a conventional titration method.

Specific examples of strong acids include a sulfonic acid, such as an arylsulfonic acid or an alkylsulfonic acid; sulfuric acid; and hydrochloric acid. An example of an arylsulfonic acid includes p-toluenesulfonic acid. Examples of alkylsulfonic acids include methanesulfonic acid and trifluoromethane sulfonic acid. In consideration of solubility in an organic solvent and ease in purification, p-toluenesulfonic acid is particularly desirable as the strong acid.

The carboxylic acid-generation step can be performed, for example, by dissolving the compound (0-2) in a solvent, and adding an acid to the resulting solution, followed by heating.

As the solvent, any solvent which is capable of dissolving the compound (0-2) can be used. Examples of such solvents include acetonitrile and methyl ethyl ketone.

The amount of the strong acid used is preferably 0.5 to 3 moles, and more preferably 1 to 2 moles, per 1 mole of the compound (0-2).

The heating temperature is preferably 20 to 150° C., and more preferably about 50 to 120° C. The heating time depends on the heating temperature, but in general, the heating time is preferably 0.5 to 12 hours, and more preferably 1 to 5 hours.

After the reaction, the compound (0-2) within the reaction mixture may be separated and purified. The separation and purification can be conducted by a conventional method. For example, any one of concentration, solvent extraction, distillation, crystallization, recrystallization and chromatography can be used alone, or two or more of these methods may be used in combination.

The method of reacting the compound (1-3) with the compound (2-1) is not particularly limited, and can be performed, for example, by allowing the compound (1-3) to come in contact with the compound (2-1) in a reaction solvent. Such a method can be performed, for example, by adding the compound (2-1) to a solution obtained by dissolving the compound (1-3) in a reaction solvent, in the presence of a base.

As the reaction solvent, any solvent which is capable of dissolving the compound (1-3) and the compound (2-1) as the raw materials can be used. Specific examples of such solvents include tetrahydrofuran (THF), acetone, dimethylformamide (DMF), dimethylacetamide, dimethylsulfoxide (DMSO) and acetonitrile.

Examples of the base include organic bases such as triethylamine, 4-dimethylaminopyridine (DMAP) and pyridine; and inorganic bases such as sodium hydride, $K_2CO_3$ and $Cs_2CO_3$.

The amount of the compound (2-1) is preferably 1 to 3 equivalents, and more preferably 1 to 2 equivalents, based on the amount of the compound (1-3).

The reaction temperature is preferably −20 to 40° C., more preferably 0 to 30° C. The reaction time depends on the reactivity of the compounds (1-3) and (2-1), the reaction temperature or the like. However, in general, the reaction time is preferably 1 to 120 hours, and more preferably 1 to 48 hours.

The reaction between the compound (b0-01) and the compound (b0-02) can be conducted by a conventional salt substitution method. For example, the reaction may be conducted by dissolving the compound (b0-01) and the compound (b0-02) in a solvent such as water, dichloromethane, acetonitrile, methanol or chlororform, followed by stirring or the like.

The reaction temperature is preferably 0 to 150° C., and more preferably 0 to 100° C. The reaction time varies depending on the reactivity of the compound (b0-1) and the compound (b0-2), the reaction temperature, and the like. However, in general, the reaction temperature is preferably 0.5 to 10 hours, and more preferably 1 to 5 hours.

After the reaction, the compound (b1-1-2) within the reaction mixture may be separated and purified. The separation and purification can be conducted by a conventional method. For example, any one of concentration, solvent extraction, distillation, crystallization, recrystallization and chromatography can be used alone, or two or more of these methods may be used in combination.

[Production Method of Compound Having an Anion Moiety Represented by General Formula (b1-3-31)]

A compound (b1-1-3) having an anion moiety represented by general formula (b1-3-31) can be produced by reacting a compound (I-5) represented by general formula (I-5) shown below with a compound (b0-2) represented by general formula (b0-2) shown below.

[Chemical Formula 64]

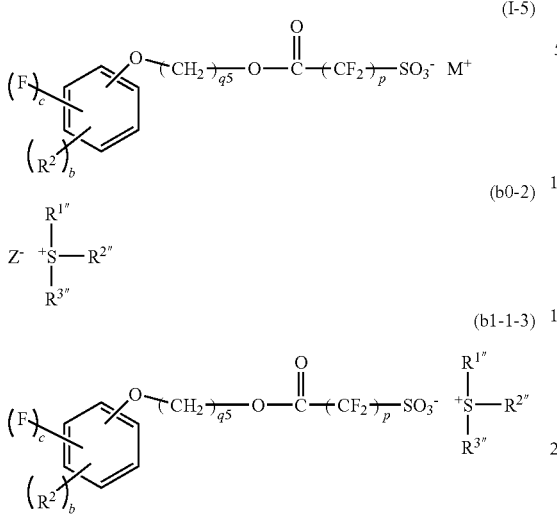

In the formulas, $R^2$, b, c, q5 and p are respectively the same as defined for $R^2$, b, c, q5 and p in general formula (b1-3-31). $M^+$ is the same as defined above. $Z^-$ is the same as defined for $Z^-$ in general formula (b0-2). $R^{1''}$ to $R^{3''}$ are respectively the same as defined for $R^{1''}$ to $R^{3''}$ in general formula (b1-1).

As the compound (I-5) and the compound (b0-2), commercially available compounds may be used, or the compounds may be synthesized by a conventional method.

The production method of the compound (I-5) is not particularly limited. For example, the compound (I-5) can be produced by conducting dehydration/condensation between a compound (1-2) represented by general formula (1-2) shown below and a compound (I-4) represented by general formula (I-4) shown below in the presence of an acidic catalyst.

[Chemical Formula 65]

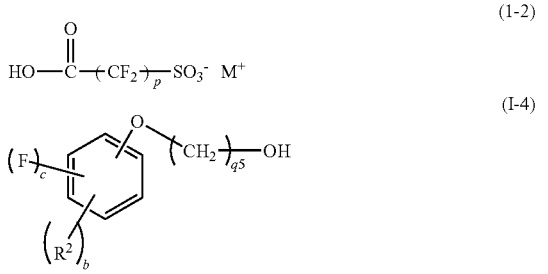

The compound (1-2) is the same as the compound (1-2) used in the synthesis of the aforementioned compound (1-3).

In general formula (I-4), $R^2$, b, c and q5 are respectively the same as defined for $R^2$, b, c, q5 and p in general formula (b1-3-31).

As the compound (1-2) and the compound (I-4), commercially available compounds may be used, or the compounds may be synthesized.

The dehydration/condensation reaction between the compound (1-2) and the compound (I-4) can be performed by dissolving the compound (1-2) and the compound (I-4) in an aprotic organic solvent such as dichloroethane, benzene, toluene, ethylbenzene, chlorobenzene, acetonitrile or N,N-dimethylformamide, followed by stirring in the presence of an acidic catalyst.

In the dehydration/condensation reaction, in terms of improving the yield, purity and the like of the obtained compound (I), it is particularly desirable to use an aromatic organic solvent (e.g., toluene, xylene or chlorobenzene) as the organic solvent.

The reaction temperature of the dehydration/condensation reaction is preferably about 20 to 200° C., and more preferably 50 to 150° C. The reaction time depends on the reactivity of the compounds (1-2) and (I-4), the reaction temperature or the like. However, in general, the reaction time is preferably 1 to 30 hours, and more preferably 3 to 30 hours.

The amount of the compound (1-2) used in the dehydration/condensation reaction is not particularly limited, but in general, the amount of the compound (1-2) is preferably about 0.2 to 3 moles, more preferably about 0.5 to 2 moles, and more preferably about 0.75 to 1.5 mole, per mole of the compound (I-4).

Examples of the acidic catalyst include an organic acid such as p-toluenesulfonic acid, and an organic acid such as sulfuric acid or hydrochloric acid. These acidic catalysts may be used individually or in a combination of two or more.

In the dehydration/condensation reaction, the acidic catalyst may be used in a catalyst amount. In general, the amount of the acidic catalyst used is about 0.001 to 5 moles, per mole of the compound (I-4).

The dehydration/condensation reaction may be conducted while removing water by using a Dean-Stark apparatus. In this manner, the reaction time can be shortened.

Further, in the dehydration/condensation reaction, a dehydrating agent such as 1,1'-carbonyldiimidazole or N,N'-dicyclohexylcarbodiimide may also be used.

When a dehydrating agent is used, in general, the amount of the dehydrating agent is preferably 0.2 to 5 moles, more preferably 0.5 to 3 moles, per 1 mole of the compound (I-4).

The reaction between the compound (I-5) and the compound (b0-2) can be effected by dissolving the compounds in a solvent such as water, dichloromethane, acetonitrile, methanol, chloroform or methylene chloride, followed by stirring.

The reaction temperature is preferably 0 to 150° C., and more preferably 0 to 100° C. The reaction time varies depending on the reactivity of the compound (I-5) and the compound (b0-2), the reaction temperature, and the like. However, in general, the reaction temperature is preferably 0.5 to 10 hours, and more preferably 1 to 5 hours.

In general, the amount of the compound (b0-2) used in the reaction is preferably 0.5 to 2 moles, per 1 mole of the compound (I-5).

After the reaction, the compound (b1-1-3) within the reaction mixture may be separated and purified. The separation and purification can be conducted by a conventional method. For example, any one of concentration, solvent extraction, distillation, crystallization, recrystallization and chromatography can be used alone, or two or more of these methods may be used in combination.

[Production Method of Compound Having an Anion Moiety Represented by General Formula (b1-3-41)]

A compound (b1-1-4) having an anion moiety represented by general formula (b1-3-41) can be produced by reacting a compound (I-6) represented by general formula (I-6) shown below with a compound (b0-2) represented by general formula (b0-2) shown below.

[Chemical Formula 66]

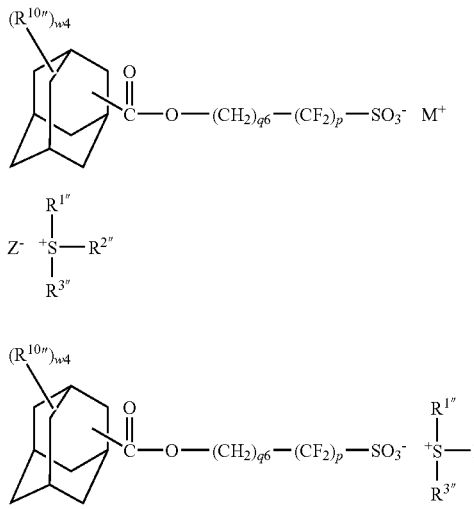

(I-6)

(b0-2)

(b1-1-4)

In the formulas, p, q6, w4 and $R^{10\prime\prime}$ are respectively the same as defined for p, q6, w4 and $R^{10\prime\prime}$ in general formula (b1-3-41). $M^+$ is the same as defined above. $Z^-$ is the same as defined for $Z^-$ in general formula (b0-2). $R^{1\prime\prime\prime}$ to $R^{3\prime\prime\prime}$ are respectively the same as defined for $R^{1\prime\prime\prime}$ to $R^{3\prime\prime\prime}$ in general formula (b1-1).

As the compound (I-6) and the compound (b0-2), commercially available compounds may be used, or the compounds may be synthesized by a conventional method.

The production method of the compound (I-6) is not particularly limited, and the compound (I-6) can be produced by a conventional method.

The reaction between the compound (I-6) and the compound (b0-2) can be effected by dissolving the compounds in a solvent such as water, dichloromethane, acetonitrile, methanol, chloroform or methylene chloride, followed by stirring.

The reaction temperature is preferably 0 to 150° C., and more preferably 0 to 100° C. The reaction time varies depending on the reactivity of the compound (I-6) and the compound (b0-2), the reaction temperature, and the like. However, in general, the reaction temperature is preferably 0.5 to 10 hours, and more preferably 1 to 5 hours.

In general, the amount of the compound (b0-2) used in the reaction is preferably 0.5 to 2 moles, per 1 mole of the compound (I-6).

After the reaction, the compound (b1-1-4) within the reaction mixture may be separated and purified. The separation and purification can be conducted by a conventional method. For example, any one of concentration, solvent extraction, distillation, crystallization, recrystallization and chromatography can be used alone, or two or more of these methods may be used in combination.

(Production Method of Compound (B1'))

The compound (B1'), i.e., the compound represented by general formula (b1-1') above can be produced, for example, by reacting a compound (b0-1') represented by general formula (b0-1') shown below with a compound (b0-2') represented by general formula (b0-2') shown below.

[Chemical Formula 67]

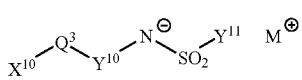

(b0-1')

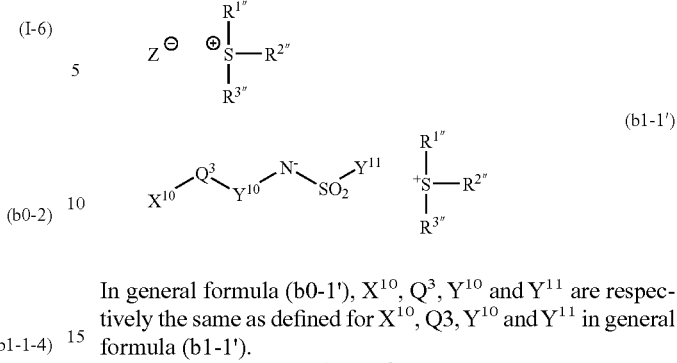

In general formula (b0-1'), $X^{10}$, $Q^3$, $Y^{10}$ and $Y^{11}$ are respectively the same as defined for $X^{10}$, Q3, $Y^{10}$ and $Y^{11}$ in general formula (b1-1').

In formula (b0-2'), $R^{1\prime\prime\prime}$ to $R^{3\prime\prime\prime}$ are respectively the same as defined for $R^{1\prime\prime\prime}$ to $R^{3\prime\prime\prime}$ in general formula (b1-1').

In formula (b0-1'), $M^+$ represents an alkali metal ion or an ammonium ion which may have a substituent, and is the same as defined for $M^+$ in formula (b0-1).

In formula (b0-2'), $Z^-$ represents a non-nucleophilic ion, and is the same as defined for $Z^-$ in formula (b0-2).

The reaction between the compound (b0-1') and the compound (b0-2') can be effected by dissolving the compounds in a solvent such as water, dichloromethane, acetonitrile, methanol, chloroform or methylene chloride, followed by stirring.

The reaction temperature is preferably 0 to 150° C., and more preferably 0 to 100° C.

The reaction time varies depending on the reactivity of the compound (b0-1') and the compound (b0-2'), the reaction temperature, and the like. However, in general, the reaction temperature is preferably 0.5 to 30 hours, and more preferably 1 to 20 hours.

In general, the amount of the compound (b0-2') used in the reaction is preferably 0.5 to 2 moles, per 1 mole of the compound (b0-1').

The structure of the compound of the present invention obtained in the manner described above can be confirmed by a general organic analysis method such as $^1$H-nuclear magnetic resonance (NMR) spectrometry, $^{13}$C-NMR spectrometry, $^{19}$F-NMR spectrometry, infrared absorption (IR) spectrometry, mass spectrometry (MS), elementary analysis and X-ray diffraction analysis.

The method of producing the compound (b0-1') is not particularly limited. For example, a method in which a compound (b0-1-1) represented by general formula (b0-1-1) shown below is reacted with a compound (b0-1-2) represented by general formula (b1-1-2) in the presence of a base and an organic solvent to thereby obtain the compound (b0-1') can be preferably used.

[Chemical Formula 68]

$X^{10}$—$Q^3$—$Y^{10}$—$X_h$ (b0-1-1)

$H_2N$—$SO_2$—$Y^{11}$ (b0-1-2)

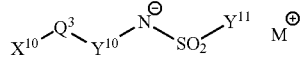

(b0-1')

In general formulas (b0-11-1) and (b0-1-2), $X^{10}$, $Q^3$, $Y^{10}$ and $Y^{11}$ are respectively the same as defined for $X^{10}$, $Q^3$, $Y^{10}$ and $Y^{11}$ in general formula (b0-1').

$X_h$ represents a halogen atom, and examples thereof include a fluorine atom, a chlorine atom, a bromine atom and an iodine atom.

As the compound (b0-1-1) and the compound (b0-1-2), commercially available compounds may be used, or the compounds may be synthesized.

The reaction of the compound (b0-1-1) with the compound (b0-1-2) can be performed as follows. Firstly, the compound (b0-1-2) is dissolved in an appropriate organic solvent, followed by stirring in the presence of an appropriate base.

In the above reaction, in terms of improving the yield, the purity and the like of the obtained compound (b0-1'), it is particularly desirable to use acetone, tetrahydrofuran (THF), methanol, ethanol or dichloromethane as the organic solvent.

Thereafter, the reaction solution is cooled with ice, and the compound (b0-1-1) is added thereto, followed by stirring. Then, the reaction mixture is subjected to filtration, and the filtrate is dried.

Finally, the resultant is washed with an organic solvent or the like such as tert-butylmethylether (TBME).

The reaction temperature is preferably 20 to 200° C., and more preferably 20 to 150° C.

The reaction time varies depending on the reactivity of the compound (b0-1-1) and the compound (b0-1-2), the reaction temperature, and the like. However, in general, the reaction temperature is preferably 1 to 80 hours, and more preferably 3 to 70 hours.

The amount of the compounds used in the reaction is not particularly limited, but in general, the amount of the compound (b0-1-2) is preferably 0.5 to 5 moles, and more preferably 1 to 5 moles, per 1 mole of the compound (b0-1-1).

Examples of the base include sodium carbonate, potassium carbonate, triethylamine and sodium hydride. These bases may be used individually or in a combination of two or more.

The base may be used in a catalyst amount, or in an amount corresponding to the solvent. In general, the amount of the base is about 0.001 to 5 moles, per 1 mole of the compound (b0-1-1).

The compound (b0-2') can be produced in the same manner as the aforementioned compound (b0-2).

(Production Method of Compound (B1''))

The compound (B1''), i.e., the compound represented by general formula (b1-1'') above can be produced, as follows. For example, a compound (b0-1-11'') represented by general formula (b0-1-11'') is reacted with an aqueous solution of an alkali metal compound (e.g., sodium hydroxide, lithium hydroxide, or the like) or an ammonium compound in an organic solvent (e.g., tetrahydrofuran, acetone, methyl ethyl ketone, or the like) or water, thereby obtaining a compound (b0-1'') represented by general formula (b0-1'') shown below.

Then, for example, the compound (b0-1'') is reacted with a compound (b0-2'') represented by general formula (b0-2'') shown below in an aqueous solution.

[Chemical Formula 69]

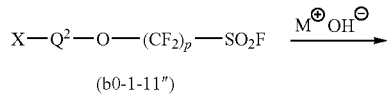

(b0-1-11'')

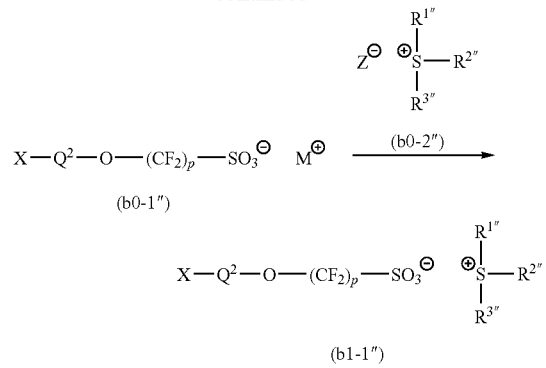

In formulas (b0-1-11''), (b0-1'') and (b0-2''), X, $Q^2$ and p are respectively the same as defined for X, $Q^2$ and p in general formula (b1-1'').

In formula (b0-2''), $R^{1''}$ to $R^{3''}$ are respectively the same as defined for $R^{1''}$ to $R^{3''}$ in general formula (b1-1'').

In formula (b0-1''), M$^+$ represents an alkali metal ion or an ammonium ion which may have a substituent, and is the same as defined for M$^+$ in formula (b0-1).

In formula (b0-2''), Z$^-$ represents a non-nucleophilic ion, and is the same as defined for Z$^-$ in formula (b0-2).

As the compound (b0-1-11''), commercially available compounds may be used, or the compounds may be synthesized by a conventional method.

The method of producing the compound (b0-1-11'') is not particularly limited. For example, referring to the method described in Example 1 of Published Japanese Translation No. Hei 11-502543 of the PCT International Publication, silver fluoride (AgF), a compound represented by general formula (b0-1-02) shown below and a compound represented by general formula (b0-1-02) shown below can be reacted in an organic solvent such as diglyme anhydride.

In general formula (b0-1-02), as the halogen atom for $X_h$, a bromine atom or a chlorine atom is preferable.

[Chemical Formula 70]

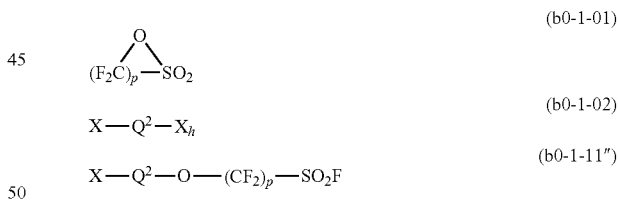

In the formulas, X, $Q^2$ and p are respectively the same as defined for X, $Q^2$ and p in general formula (b0-1''); and $X_h$ represents a halogen atom.

The compound represented by general formula (b1-3-01) can be produced, for example, by a method described in Japanese Unexamined Patent Application, First Publication No. 2006-348382 or U.S. Pat. No. 6,624,328 B1.

The compound (b0-2'') can be produced in the same manner as the aforementioned compound (b0-2).

The structure of the compound obtained in the manner described above can be confirmed by a general organic analysis method such as $^1$H-1-nuclear magnetic resonance (NMR) spectrometry, $^{13}$C-NMR spectrometry, $^{19}$F-NMR spectrometry, infrared absorption (IR) spectrometry, mass spectrometry (MS), elementary analysis and X-ray diffraction analysis.

The compound of the present invention described above is a novel compound useful as an acid generator for a resist composition, and can be blended in a resist composition as an acid generator.

Further, since the fluorinated alkylene group "—$(CF_2)_p$—" in the anion moiety exhibits excellent decomposability as compared to a perfluoroalkyl chain of 6 to 10 carbon atoms which is hardly decomposable, the compound of the present invention is advantageous in that bioaccumulation can be minimized to improve safety in handling.

<<Acid Generator>>

The acid generator according to a fourth aspect of the present invention is an acid generator including the aforementioned compound of the third aspect.

The acid generator is useful for a chemically amplified resist composition, for example, the acid-generator component (B) of the resist composition according to the first aspect of the present invention.

EXAMPLES

As follows is a description of examples of the present invention, although the scope of the present invention is by no way limited by these examples.

<Synthesis of Compound (B1)>

Examples 1 to 8

Novel compounds (B1-1) to (B1-8) were synthesized in accordance with the following synthesis examples.

[Synthesis Example 1

Synthesis of Compound (1)]

[Chemical Formula 71]

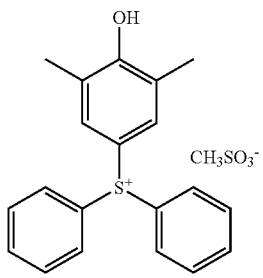

(1)

To 60.75 g of methanesulfonic acid controlled to 20° C. or lower was added 8.53 g of phosphorus oxide, 8.81 g of 2,6-dimethylphenol and 12.2 g of diphenylsulfoxide in small amounts. The resultant was matured for 30 minutes while maintaining the temperature at 15 to 20° C., followed by elevating the temperature to 40° C. and maturing for 2 hours. Then, the reaction mixture was dropwise added to 109.35 g of pure water cooled to 15° C. or lower. Thereafter, 54.68 g of dichloromethane was added and stirred, and the dichloromethane phase was collected. 386.86 g of hexane at a temperature of 20 to 25° C. was added to a separate vessel, and the dichloromethane phase was dropwise added thereto. Then, the resultant was matured at 20 to 25° C. for 30 minutes, followed by filtration, thereby obtaining an intermediate compound (1) as an objective compound (yield: 70.9%).

The obtained intermediate compound (1) was analyzed by $^1$H-NMR.

$^1$H-NMR (DMSO-d6, 600 MHz): δ(ppm)=7.61-7.72 (m, 10H, phenyl), 7.14 (S, 2H, $H^c$), 3.12 (S, 3H, $H^b$), 2.22 (s, 6H, $H^a$)

From the results shown above, it was confirmed that the compound (1) had a structure shown below.

[Chemical Formula 72]

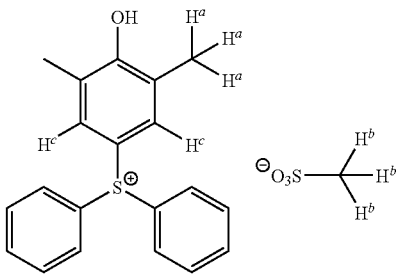

[Synthesis Example 2

Synthesis of Compound (2)]

10.65 g of a compound (1) and 106.46 g of acetonitrile were added to a three-necked flask in a nitrogen atmosphere, followed by stirring. Then, 18.28 g of potassium carbonate was added thereto, and stirring was conducted at room temperature for 10 minutes, followed by dropwise adding 32.1 g of 2-chloroethylvinylether.

Subsequently, the temperature of the resultant was elevated to 80° C., and stirring was conducted for 72 hours. The reaction solution was cooled to room temperature, and subjected to filtration. Then, the filtrate was subjected to concentration and drying using a rotary evaporator. The obtained oil product was dissolved in 52.47 g of water, and washed with 52.47 g of hexane three times. Thereafter, extraction was conducted with 159.69 g of dichloromethane, and the organic solvent phase was washed with 52.47 g of water three times. After the washing, the organic solvent phase was concentrated and solidified, thereby obtaining 5.6 g of a compound (2) as an objective precursor.

The obtained compound (2) was analyzed by NMR.

$^1$H-NMR (CDCl$_3$, 400 MHz): δ(ppm)=7.69-7.81 (m, 10H, Ar), 7.46 (s, 2H, Ar), 6.49-6.55 (m, 1H Vinyl), 4.02-4.27 (m, 6H, CH$_2$+Vinyl), 2.75 (s, 3H, CH$_3$SO$_3$), 2.36 (s, 6H, CH$_3$)

Further, from the results of an ion chromatograph, it was found that the obtained compound was a mixture of compounds having different anion moieties, namely, a mixture of a CH$_3$SO$_3$ compound and a Cl compound with a mixing ratio of CH$_3$SO$_3$:Cl=73.4:26.6 (molar ratio).

From the results shown above, it was confirmed that the compound (2) had a structure shown below.

[Chemical Formula 73]

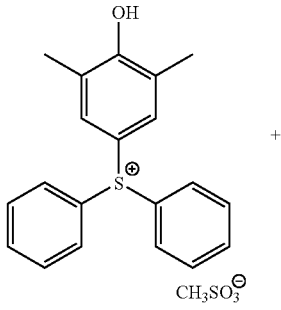

Compound (1)

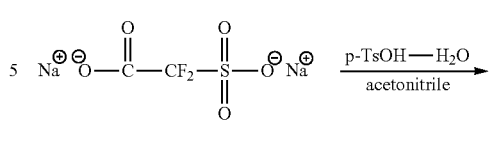

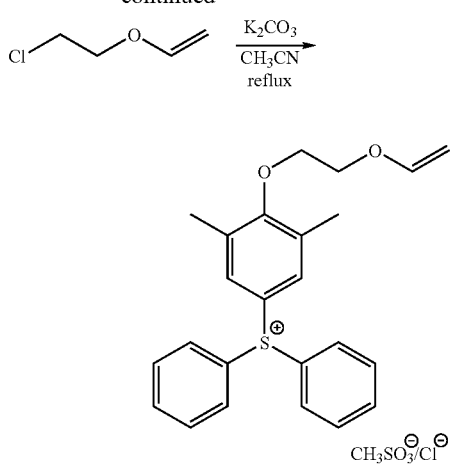

Compound (2)

[Example 1

Synthesis of Compound (B1-1)]

(i) Synthesis Example of Compound (3)

150 g of methyl fluorosulfonyl(difluoro)acetate and 375 g of pure water were maintained at 10° C. or lower in an ice bath, and 343.6 g of a 30% by weight aqueous solution of sodium hydroxide was dropwise added thereto. Then, the resultant was refluxed at 100° C. for 3 hours, followed by cooling and neutralizing with a concentrated hydrochloric acid. The resulting solution was dropwise added to 8,888 g of acetone, and the precipitate was collected by filtration and dried, thereby obtaining 184.5 g of a compound (I) in the form of a white solid (purity: 88.9%, yield: 95.5%).

[Chemical Formula 74]

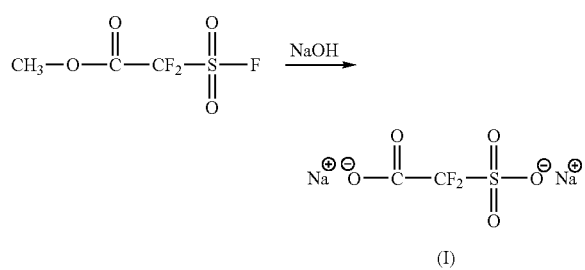

(I)

Subsequently, 56.2 g of the compound (I) and 562.2 g of acetonitrile were prepared, and 77.4 g of p-toluenesulfonic acid monohydrate was added thereto. The resultant was refluxed at 110° C. for 3 hours. Then, the reaction mixture was filtered, and the filtrate was concentrated and dried to obtain a solid. 900 g of t-butyl methyl ether was added to the obtained solid and stirred. Thereafter, the resultant was filtered, and the residue was dried, thereby obtaining 22.2 g of a compound (II) in the form of a white solid (purity: 91.0%, yield: 44.9%).

[Chemical Formula 75]

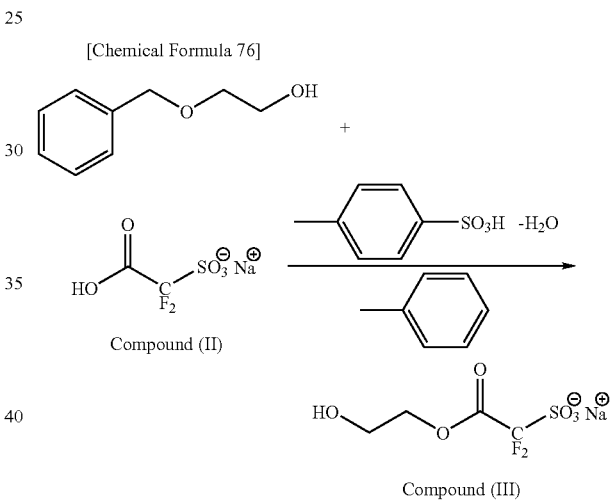

Subsequently, 4.34 g of the compound (II) (purity: 94.1%), 3.14 g of 2-benzyloxyethanol and 43.4 g of toluene were prepared, and 0.47 g of p-toluenesulfonic acid monohydrate was added thereto. The resultant was refluxed at 105° C. for 20 hours. Then, the reaction mixture was filtered, and 20 g of hexane was added to the residue and stirred. Thereafter, the resultant was filtered, and the residue was dried, thereby obtaining 1.41 g of a compound (III) (yield: 43.1%).

[Chemical Formula 76]

The obtained compound (III) was analyzed by NMR.
$^1$H-NMR (DMSO-d6, 400 MHz): δ(ppm)=4.74-4.83 (t, 1H, OH), 4.18-4.22 (t, 2H, H$^a$), 3.59-3.64 (q, 2H, H$^b$)
$^{19}$F-NMR (DMSO-d6, 376 MHz): δ(ppm)=−106.6
From the results shown above, it was confirmed that the compound (III) had a structure shown below.

[Chemical Formula 77]

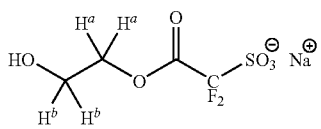

Next, 1.00 g of the compound (III) and 3.00 g of acetonitrile were prepared, and 0.82 g of 1-adamantanecarbonyl chloride and 0.397 g of triethylamine were dropwise added thereto while cooling with ice. Then, the resultant was stirred at room temperature for 20 hours, followed by filtration. The filtrate was concentrated and dried, and dissolved in 30 g of dichloromethane, followed by washing with water three times. Thereafter, the organic phase was concentrated and dried, thereby obtaining 0.82 g of a compound (3) (yield: 41%).

[Chemical Formula 78]

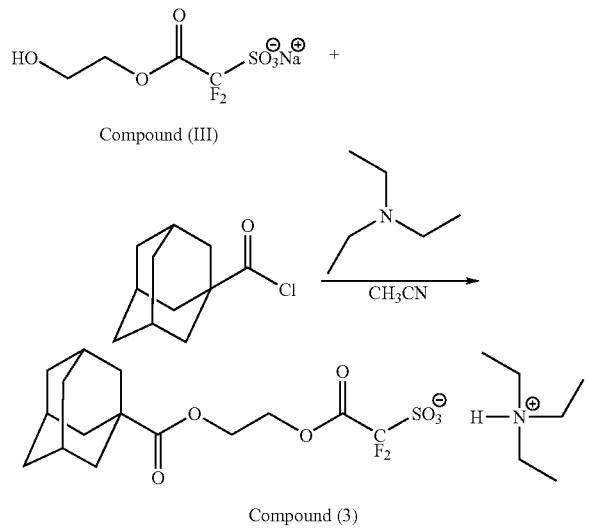

The obtained compound (3) was analyzed by NMR.

$^1$H-NMR (DMSO-d6, 400 MHz): δ(ppm)=8.81 (s, 1H, H$^c$), 4.37-4.44 (t, 2H, H$^d$), 4.17-4.26 (t, 2H, H$^e$), 3.03-3.15 (q, 6H, H$^b$), 1.61-1.98 (m, 15H, Adamantane), 1.10-1.24 (t, 9H, H$^a$)

$^{19}$F-NMR (DMSO-d6, 376 MHz): δ(ppm)=−106.61

From the results shown above, it was confirmed that the compound (3) had a structure shown below.

[Chemical Formula 79]

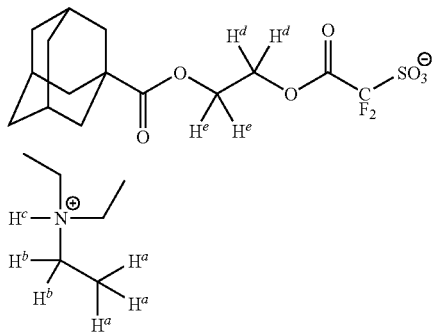

(ii) Synthesis Example of Compound (B1-1)

2 g of the compound (2) was added to 20 g of dichloromethane and 20 g of water, followed by stirring. Then, 2.54 g of a compound (3) was added thereto, followed by stirring for 1 hour. The reaction mixture was subjected to liquid separation, and the resultant was washed four times with 20 g of water. After the washing, the organic solvent phase was concentrated and solidified, thereby obtaining 2.3 g of a compound (B1-1).

The obtained compound (B1-1) was analyzed by NMR.

$^1$H-NMR (DMSO-d6, 400 MHz): δ(ppm)=7.72-7.83 (m, 10H, Ar), 7.72 (s, 2H, Ar), 6.49-6.55 (m, 1H, Vinyl), 4.37-4.44 (t, 2H, CH$_2$), 4.20-4.23 (d, 1H, Vinyl), 4.00-4.26 (m, 7H, CH$_2$+Vinyl), 2.27 (s, 6H, CH$_3$), 1.61-1.98 (m, 15H, Adamantane)

$^{19}$F-NMR (DMSO-d6, 376 MHz): δ(ppm)=−106.61

From the results shown above, it was confirmed that the compound (B1-1) had a structure shown below.

[Chemical Formula 80]

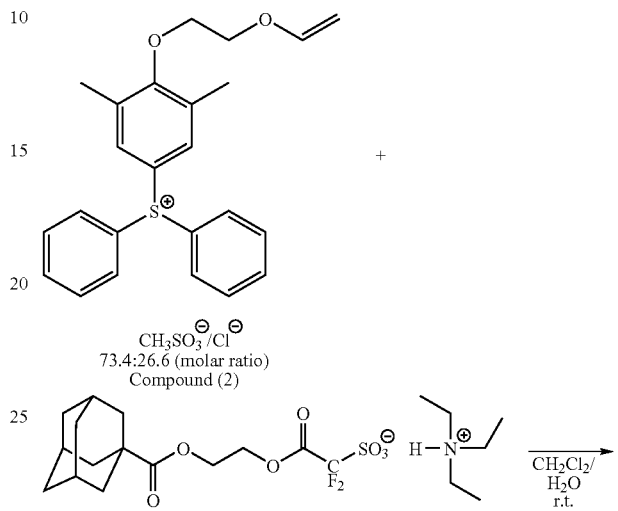

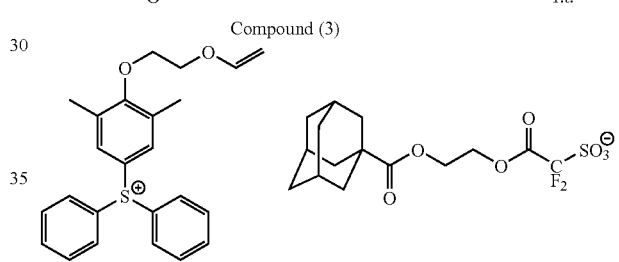

[Example 2

Synthesis of Compound (B1-2)]

(i) Synthesis Example of Compound (4)

5.00 g of the compound (II) obtained in Example 1 (purity: 91.0%), 10.48 g of pentafluorophenoxyethanol and 50.00 g of toluene were prepared, and 0.935 g of p-toluenesulfonic acid monohydrate was added thereto. The resultant was refluxed at 110° C. for 15 hours. Thereafter, the reaction mixture was filtered, and 46.87 g of toluene was added to the residue, followed by stirring at room temperature for 15 minutes. This filtration step was performed twice to obtain a white powder. The white powder was dried under reduced pressure for one night. On the next day, 46.87 g of acetonitrile was added to the white powder, followed by stirring at room temperature for 15 minutes. Then, the resultant was subjected to filtration, and the obtained filtrate was gradually added to 468.7 g of TBME in a dropwise manner. The precipitated solid was collected by filtration and dried, thereby obtaining 6.69 g of a compound (4) in the form of a white powder (purity: 99.5%, yield: 71.0%).

[Chemical Formula 81]

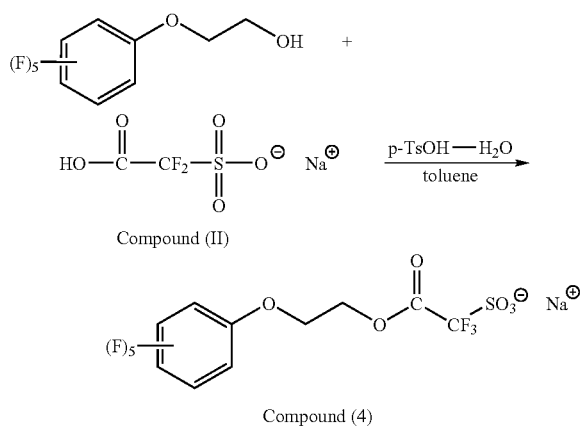

The compound (4) was analyzed by $^1$H-NMR and $^{19}$F-NMR.

$^1$H-NMR (DMSO-d6, 400 MHz): δ(ppm) 4.4-4.5 (t, 4H, Ha, Hb)

$^{19}$F-NMR (DMSO-d6, 400 MHz): δ(ppm)−106.7 (s, 2F, Fa), −154.0 (s, 2F, Fb), −160.0−−161.5 (s, 3F, Fc) (the peak of hexafluorobenzene was regarded as −160 ppm)

From the results shown above, it was confirmed that the compound (4) had a structure shown below.

[Chemical Formula 82]

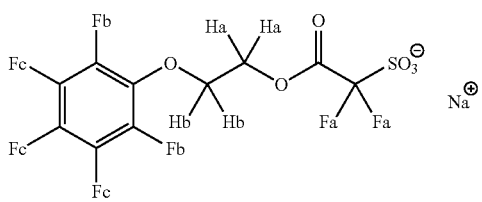

(ii) Synthesis Example of Compound (B1-2)

2 g of the compound (2) was added to 20 g of dichloromethane and 20 g of water, followed by stirring. Then, 2.14 g of a compound (4) was added thereto, followed by stirring for 1 hour. The reaction mixture was subjected to liquid separation, and the resultant was washed four times with 20 g of water. After the washing, the organic solvent phase was concentrated and solidified, thereby obtaining 2.6 g of a compound (B1-2).

The obtained compound (B1-2) was analyzed by NMR.

$^1$H-NMR (DMSO-d6, 400 MHz): δ(ppm)=7.69-7.81 (m, 10H, Ar), 7.46 (s, 2H, Ar), 6.49-6.55 (m, 1H Vinyl), 4.4-4.5 (t, 4H, CH$_2$), 4.02-4.27 (m, 6H, CH$_2$+Vinyl), 2.36 (s, 6H, CH$_3$)

$^{19}$F-NMR (DMSO-d6, 376 MHz): δ(ppm)=−106.7 (s, 2F), −154.0 (s, 2F), −160.0, −161.5 (s, 3F)

From the results shown above, it was confirmed that the compound (B1-2) had a structure shown below.

[Chemical Formula 83]

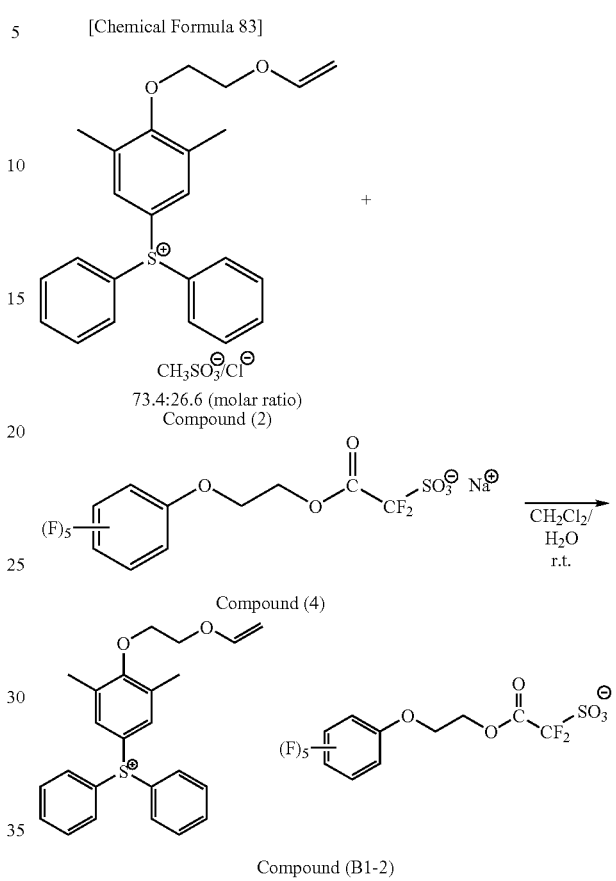

[Example 3

Synthesis of Compound (B1-3)]

(i) Synthesis Example of Compound (5)

To 2.42 g of the compound (III) obtained in Example 1 and 7.26 g of acetonitrile were dropwise added 2.19 g of undecanoylcarbonyl chloride and 1.01 g of triethylamine while cooling with ice.

Then, the resultant was stirred at room temperature for 20 hours, followed by filtration. The filtrate was concentrated and dried, and dissolved in 20 g of dichloromethane, followed by washing with water three times. Thereafter, the organic phase was concentrated and dried, thereby obtaining 3.41 g of a compound (5) (yield: 80.4%).

[Chemical Formula 84]

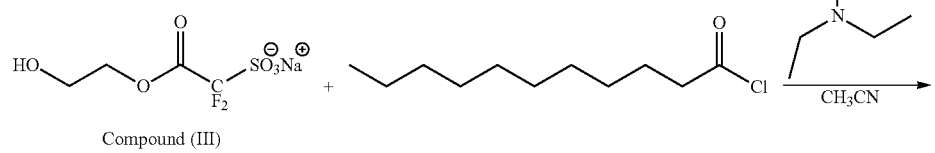

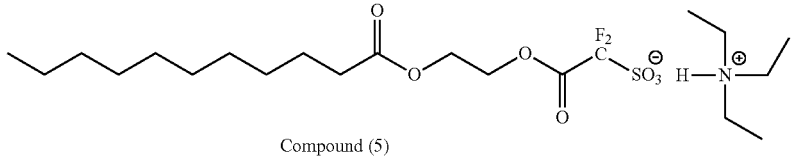

Compound (5)

The obtained compound (5) was analyzed by NMR.

$^1$H-NMR (DMSO-d6, 400 MHz): δ(ppm)=8.81 (s, 1H, H$^f$), 4.39-4.41 (t, 2H, H$^d$), 4.23-4.39 (t, 2H, H$^a$), 3.06-3.10 (q, 6H, H$^h$), 2.24-2.29 (t, 2H, H$^c$), 1.09-1.51 (m, 25H, H$^b$+H$^g$), 0.83-0.89 (t, 3H, H$^a$)

$^{19}$F-NMR (DMSO-d6, 376 MHz): δ(ppm)=−106.8

From the results shown above, it was confirmed that the compound (5) had a structure shown below.

[Chemical Formula 85]

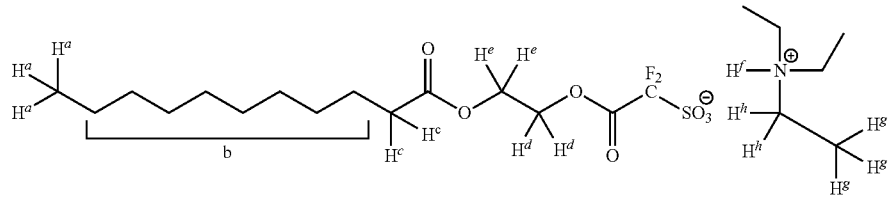

(ii) Synthesis Example of Compound (B1-3)

The same procedure as in Example 1 was performed, except that the compound (3) was changed to a compound (5) in the synthesis example (ii), thereby obtaining a compound (B1-3).

The obtained compound (B1-3) was analyzed by NMR.

$^1$H-NMR (DMSO-d6, 400 MHz): δ(ppm)=7.69-7.81 (m, 10H, Ar), 7.46 (s, 2H, Ar), 6.49-6.55 (m, 1H Vinyl), 4.39-4.42 (t, 2H, CH$_2$), 4.02-4.27 (m, 8H, CH$_2$+Vinyl), 2.36 (s, 6H, CH$_3$), 2.25-2.89 (t, 3H, CH$_3$), 1.17-1.50 (m, 15H, CH$_2$), 0.79-0.88 (t, 3H, CH$_3$)

$^{19}$F-NMR (DMSO-d6, 376 MHz): δ(ppm)=−106.8

From the results shown above, it was confirmed that the compound (B1-3) had a structure shown below.

[Chemical Formula 86]

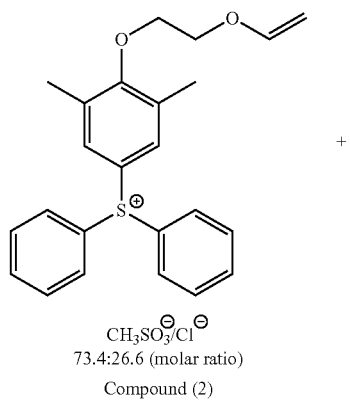

CH$_3$SO$_3^\ominus$/Cl$^\ominus$
73.4:26.6 (molar ratio)
Compound (2)

+

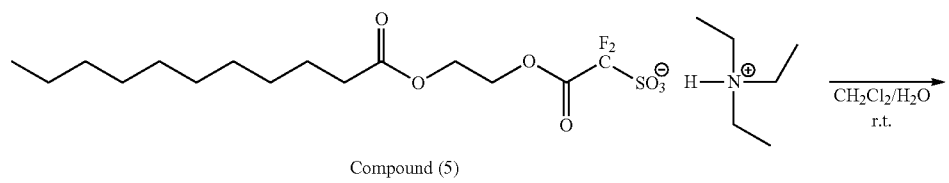

Compound (5)

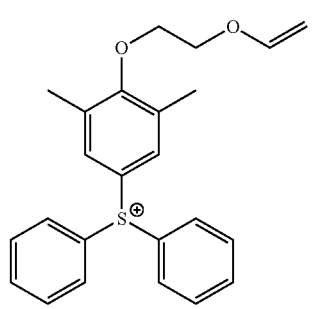
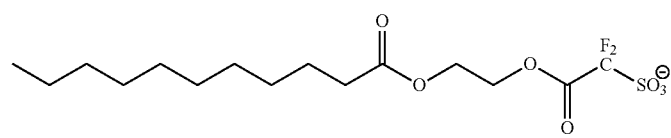

Compound (B1-3)

[Example 4]

Synthesis of Compound (B1-4)]

(i) Synthesis Example of Compound (6)

5.00 g of the compound (II) obtained in Example 1 (purity: 91.0%), 4.80 g of sultone-OH (3) and 25.0 g of toluene were prepared, and 0.935 g of p-toluenesulfonic acid monohydrate was added thereto. The resultant was refluxed at 110° C. for 26 hours. Thereafter, the reaction mixture was filtered, and 25.0 g of toluene was added to the residue, followed by stirring at room temperature for 10 minutes. This filtration step was performed twice to obtain a white powder.

The white powder was dried under reduced pressure for one night. On the next day, 5 g of acetone was added to the white powder, followed by stirring at room temperature for 15 minutes. Then, the resultant was subjected to filtration, and the obtained filtrate was gradually added to 25.0 g of TBME and 25.0 g of methylene chloride in a dropwise manner. The precipitated solid was collected by filtration and dried, thereby obtaining 5.89 g of a compound (6) in the form of a white powder (purity: 98.4%, yield: 68.1%).

[Chemical Formula 87]

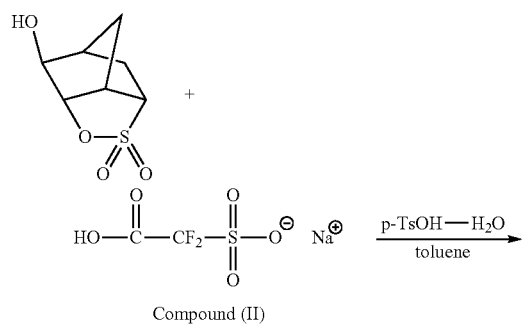

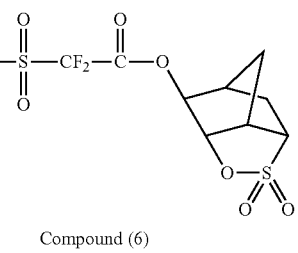

Compound (6)

The compound (6) was analyzed by $^1$H-NMR and $^{19}$F-NMR.

$^1$H-NMR (DMSO-d6, 400 MHz): δ(ppm) 1.73-2.49 (m, 4H, Ha, Hb), 2.49 (m, 1H, Hc), 3.34 (m, 1H, Hd), 3.88 (t, 1H, He), 4.66 (t, 1H, Hf), 4.78 (m, 1H, Hg)

$^{19}$F-NMR (DMSO-d6, 400 MHz): δ(ppm)±107.7 (m, 2F, Fa) (the peak of hexafluorobenzene was regarded as −160 ppm)

From the results shown above, it was confirmed that the compound (6) had a structure shown below.

[Chemical Formula 88]

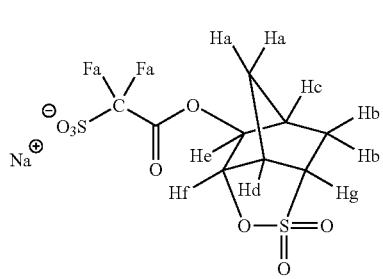

Compound (6)

(ii) Synthesis Example of Compound (B1-4)

The same procedure as in Example 2 was performed, except that the compound (4) was changed to a compound (6) in the synthesis example (ii), thereby obtaining a compound (B1-4).

The obtained compound (B1-4) was analyzed by NMR.

$^1$H-NMR (DMSO-d6, 400 MHz): δ(ppm)=7.69-7.81 (m, 10H, Ar), 7.46 (s, 2H, Ar), 6.49-6.55 (m, 1H Vinyl), 4.78 (m, 1H, CH), 4.66 (t, 1H, CH), 4.02-4.27 (m, 6H, CH$_2$+Vinyl), 3.88 (t, 1H, CH), 3.34 (m, 1H, CH), 2.49 (m, 1H, CH), 1.73-2.49 (m, 10H, sultone)

$^{19}$F-NMR (DMSO-d6, 376 MHz): δ(ppm)=−107.7

From the results shown above, it was confirmed that the compound (B1-4) had a structure shown below.

[Chemical Formula 89]

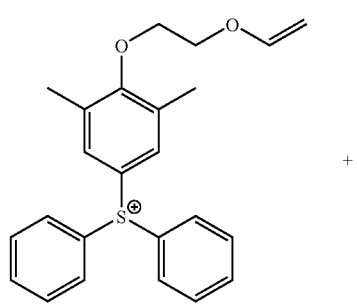

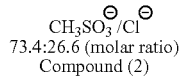

CH$_3$SO$_3^\ominus$/Cl$^\ominus$
73.4:26.6 (molar ratio)
Compound (2)

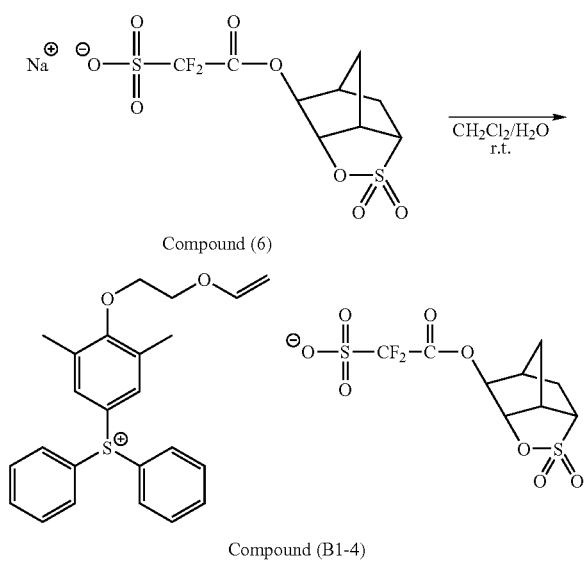

Compound (6)

Compound (B1-4)

[Example 5]

Synthesis of Compound (B1-5)]

(i) Synthesis Example of Compound (7)

10.0 g of the compound (III) obtained in Example 1 and 50 g of acetonitrile were added to a three-necked flask, and 7.35 g of isonicotinoyl chloride hydrochloride was added thereto. The resulting suspension was cooled with ice, and 8.36 g of triethylamine was gradually added thereto in a dropwise manner. After the dropwise addition, the ice cooling was stopped, followed by stirring at room temperature for 1.5 hours. Thereafter, the reaction mixture was filtered, and the filtrate was concentrated under reduced pressure. The obtained crude product was dissolved in 130.2 g of dichloromethane, and the resultant was washed with 37.2 g of water. The organic phase was concentrated and dried under reduced pressure, thereby obtaining 10.7 g of a compound (7).

[Chemical Formula 90]

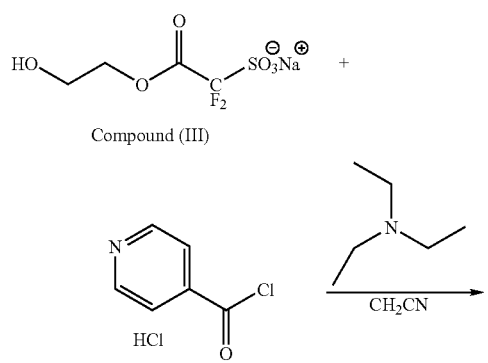

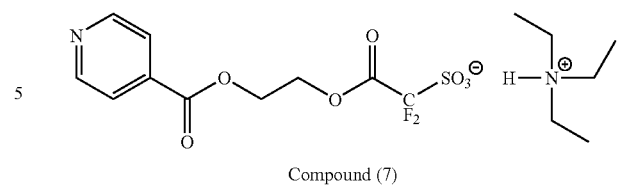

Compound (7)

The obtained compound (7) was analyzed by NMR.

$^1$H-NMR (DMSO-d6, 400 MHz): δ(ppm)=8.74-8.82 (m, 3H, Pyridyl and H$^c$), 7.84 (dd, 2H, Pyridyl), 4.54-4.61 (m, 4H, H$^d$), 3.08 (q, 6H, H$^b$), 1.16 (t, 9H, H$^a$)

$^{19}$F-NMR (DMSO-d6, 376 MHz): δ(ppm)=−106.5

From the results shown above, it was confirmed that the compound (7) had a structure shown below.

[Chemical Formula 91]

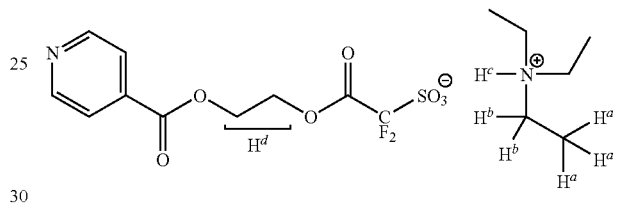

(ii) Synthesis Example of Compound (B1-5)

The same procedure as in Example 1 was performed, except that the compound (3) was changed to a compound (7) in the synthesis example (ii), thereby obtaining a compound (B1-5).

The obtained compound (B1-5) was analyzed by NMR.

$^1$H-NMR (DMSO-d6, 400 MHz): δ(ppm)=8.74-8.82 (m, 2H, Py-H), 7.84 (dd, 2H, Py-H), 7.69-7.81 (m, 10H, Ar), 7.46 (s, 2H, Ar), 6.49-6.55 (m, 1H, Vinyl), 4.54-4.61 (m, 4H, CH$_2$CH$_2$), 4.02-4.27 (m, 6H, CH$_2$+Vinyl), 2.36 (s, 6H, CH$_3$)

$^{19}$F-NMR (DMSO-d6, 376 MHz): δ(ppm)=−106.5

From the results shown above, it was confirmed that the compound (B1-5) had a structure shown below.

[Chemical Formula 92]

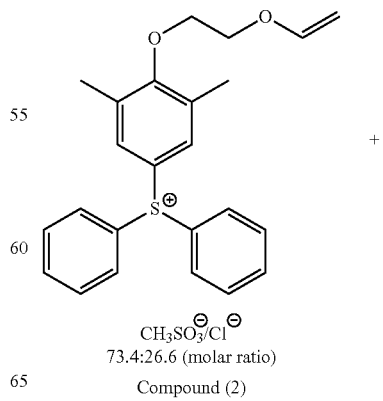

CH$_3$SO$_3^\ominus$/Cl$^\ominus$
73.4:26.6 (molar ratio)

Compound (2)

-continued

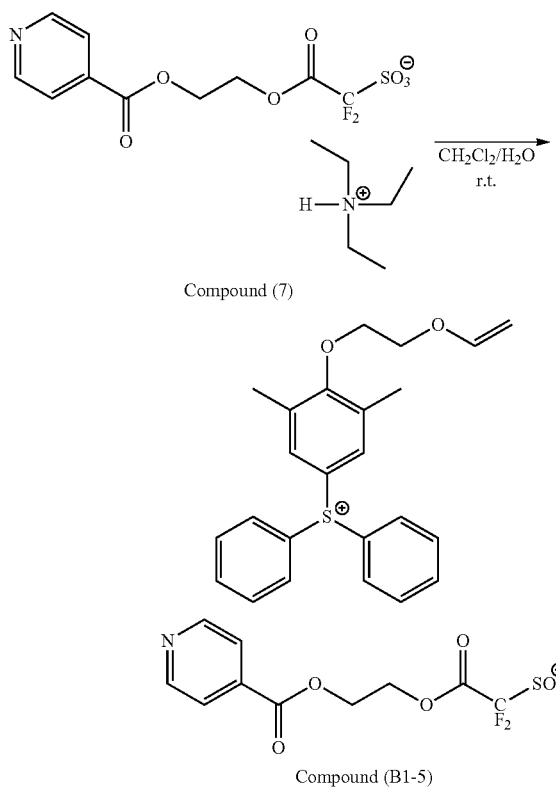

Compound (7)

Compound (B1-5)

[Example 6

Synthesis of Compound (B1-6)]

(i) Synthesis Example of Compound (8)

3.23 g of the compound (II) obtained in Example 1 (purity: 91.0%), 5.00 g of a compound (II') represented by formula (II') shown below and 32.2 g of dichloromethane were prepared, and 0.328 g of p-toluenesulfonic acid monohydrate was added thereto. The resultant was refluxed at 110° C. for 21 hours.

Then, the reaction mixture was filtered, and 49.4 g of methyl ethyl ketone was added to the residue, followed by stirring. Thereafter, the resultant was filtered, and the residue was dried, thereby obtaining 2.62 g of a compound (8) in the form of a brownish white solid (purity: 43.8%, yield: 21.3%).

[Chemical Formula 93]

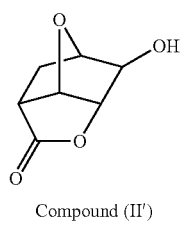

Compound (II')

-continued

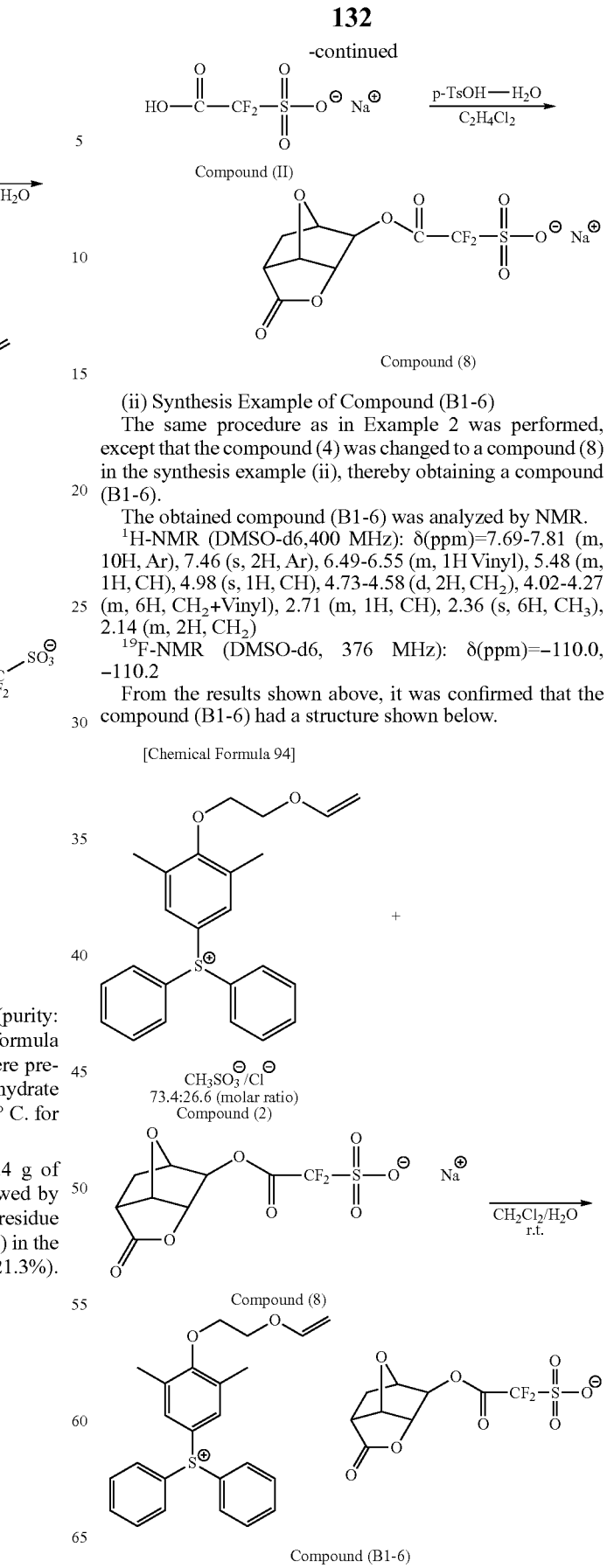

Compound (II)

Compound (8)

(ii) Synthesis Example of Compound (B1-6)

The same procedure as in Example 2 was performed, except that the compound (4) was changed to a compound (8) in the synthesis example (ii), thereby obtaining a compound (B1-6).

The obtained compound (B1-6) was analyzed by NMR.

$^1$H-NMR (DMSO-d6, 400 MHz): δ(ppm)=7.69-7.81 (m, 10H, Ar), 7.46 (s, 2H, Ar), 6.49-6.55 (m, 1H Vinyl), 5.48 (m, 1H, CH), 4.98 (s, 1H, CH), 4.73-4.58 (d, 2H, CH$_2$), 4.02-4.27 (m, 6H, CH$_2$+Vinyl), 2.71 (m, 1H, CH), 2.36 (s, 6H, CH$_3$), 2.14 (m, 2H, CH$_2$)

$^{19}$F-NMR (DMSO-d6, 376 MHz): δ(ppm)=−110.0, −110.2

From the results shown above, it was confirmed that the compound (B1-6) had a structure shown below.

[Chemical Formula 94]

Compound (2)
CH$_3$SO$_3^-$/Cl$^-$
73.4:26.6 (molar ratio)

Compound (8)

Compound (B1-6)

[Example 7]

Synthesis of Compound (B1-7)]

The same procedure as in Example 2 was performed, except that the compound (4) was changed to a compound (9) in the synthesis example (ii), thereby obtaining a compound (B1-7).

The obtained compound (B1-7) was analyzed by NMR.
$^1$H-NMR (DMSO-d6, 400 MHz): δ(ppm)=7.69-7.81 (m, 10H, Ar), 7.46 (s, 2H, Ar), 6.49-6.55 (m, 1H Vinyl), 4.55 (t, 2H, CF$_2$CH$_2$), 4.02-4.27 (m, 6H, CH$_2$+Vinyl), 2.36 (s, 6H, CH$_3$), 1.94 (m, 3H, Ad), 1.82 (m, 6H, Ad), 1.64 (m, 6H, Ad)
$^{19}$F-NMR (DMSO-d6, 376 MHz): δ(ppm)=−111.2

From the results shown above, it was confirmed that the compound (B1-7) had a structure shown below.

[Chemical Formula 95]

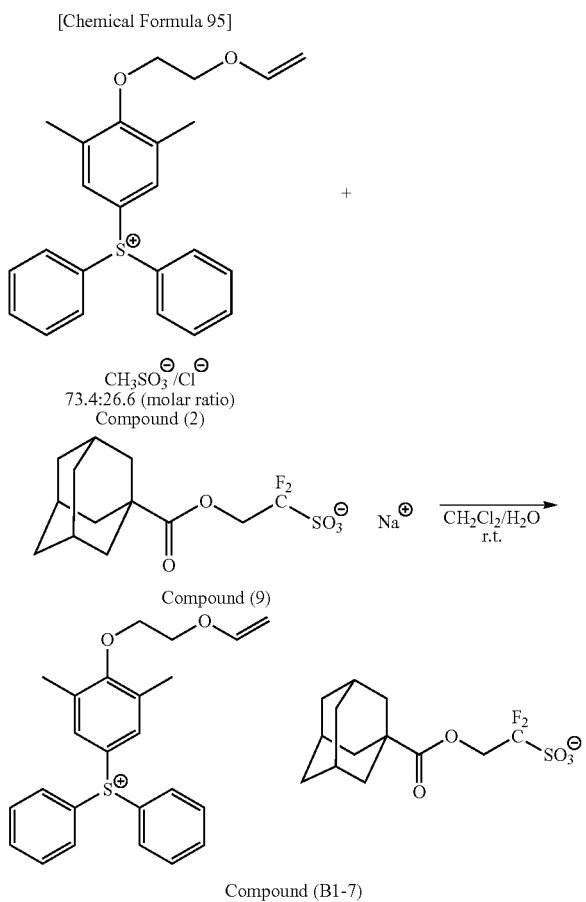

was concentrated and dried, thereby obtaining 14.90 g of a compound (10) (purity: 88.0%).

[Chemical Formula 96]

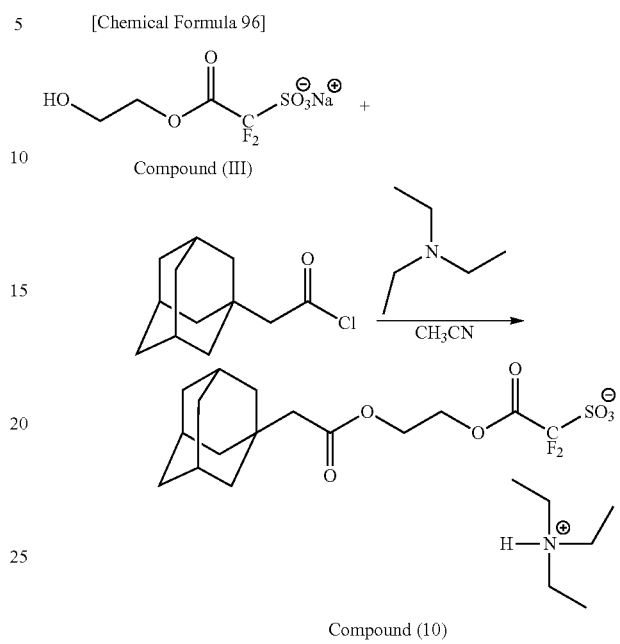

The obtained compound (10) was analyzed by NMR.
$^1$H-NMR (DMSO, 400 MHz): δ(ppm)=8.81 (br s, 1H, H$^c$), 4.40 (t, 2H, H$^d$), 4.20 (t, 2H, H$^e$), 3.08 (q, 6H, H$^b$), 2.05 (s, 2H, H$^f$), 1.53-1.95 (m, 15H, Adamantane), 1.17 (t, 9H, H$^a$)
$^{19}$F-NMR (DMSO, 376 MHz): δ(ppm)=−106.90

From the results shown above, it was confirmed that the compound (10) had a structure shown below.

[Chemical Formula 97]

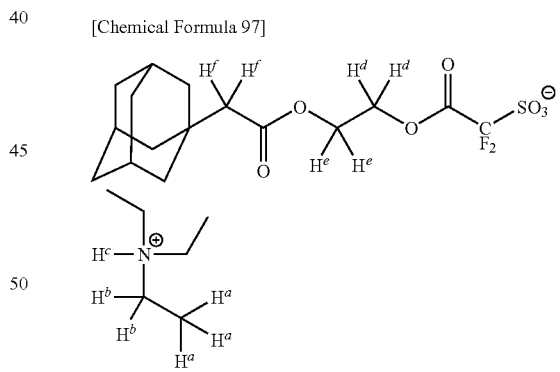

(ii) Synthesis Example of Compound (B1-8)

The same procedure as in Example 1 was performed, except that the compound (3) was changed to a compound (10) in the synthesis example (ii), thereby obtaining a compound (B1-8).

The obtained compound (B1-8) was analyzed by NMR.
$^1$H-NMR (DMSO-d6, 400 MHz): δ(ppm)=7.69-7.81 (m, 10H, Ar), 7.46 (s, 2H, Ar), 6.49-6.55 (m, 1H Vinyl), 4.40 (t, 2H, CH$_2$), 4.02-4.27 (m, 8H, CH$_2$+CH$_2$+Vinyl), 2.36 (s, 6H, CH$_3$), 2.05 (s, 2H, CH$_2$), 1.53-1.95 (m, 15H, Adamantane)
$^{19}$F-NMR (DMSO-d6, 376 MHz): δ(ppm)=−106.90

[Example 8]

Synthesis of Compound (B1-8)]

(i) Synthesis Example of Compound (10)

To 8.00 g of the compound (III) obtained in Example 1 and 150.00 g of dichloromethane were added 7.02 g of 1-adamantaneacetyl chloride and 3.18 g of triethylamine while cooling with ice. Then, the resultant was stirred at room temperature for 20 hours, followed by filtration. The filtrate was washed with 54.6 g of pure water three times, and the organic phase From the results shown above, it was confirmed that the compound (B1-8) had a structure shown below.

[Chemical Formula 98]

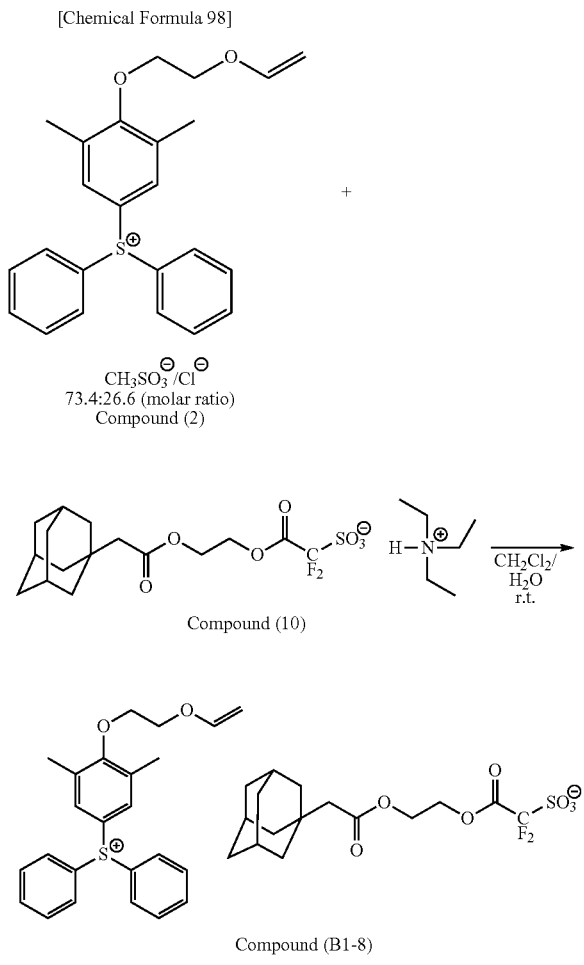

Compound (B1-8)

<Production of Resist Composition>

Example 9, Comparative Example 1

The components shown in Table 1 were mixed together and dissolved to obtain positive resist compositions.

[Chemical Formula 99]

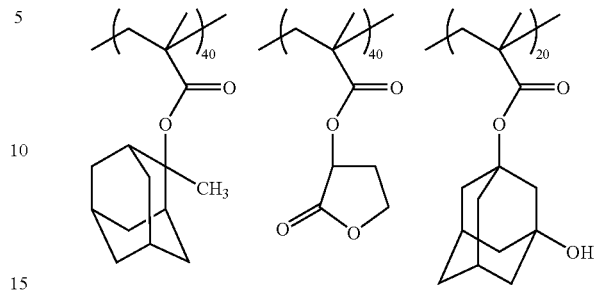

(A1-11-1)

(B)-1: the aforementioned compound (B1-6)
(B)-2: (4-methylphenyl)diphenylsulfonium nonafluoro-n-butanesulfonate
(D)-1: tri-n-pentylamine
(E)-1: salicylic acid
(S)-1: a mixed solvent of PGMEA/PGME=6/4 (weight ratio)
(S)-2: γ-butyrolactone <Evaluation of Lithographic Properties—(1)>

Using the obtained resist compositions, resist patterns were formed in the following manner, and the lithography properties were evaluated.

[Formation of Resist Pattern (1)]

An organic anti-reflection film composition (product name: ARC29A, manufactured by Brewer Science Ltd.) was applied onto an 8-inch silicon wafer using a spinner, and the composition was then baked at 205° C. for 60 seconds, thereby forming an organic anti-reflection film having a film thickness of 82 nm.

Then, each of the resist compositions obtained above was applied onto the anti-reflection film using a spinner, and was then prebaked (PAB) on a hotplate at 110° C. for 60 seconds and dried, thereby forming a resist film having a film thickness of 150 nm.

Subsequently, the resist film was selectively irradiated with an ArF excimer laser (193 nm) through a mask pattern (6% half tone), using an ArF exposure apparatus NSR-5302 (manufactured by Nikon Corporation, NA (numerical aperture)=0.60, ⅔ annular illumination).

TABLE 1

| | Component (A) | Component (B) | Component (D) | Component (E) | Component (S) | |
|---|---|---|---|---|---|---|
| Ex. 9 | (A)-1 [100] | (B)-1 [9.59] | (D)-1 [1.20] | (E)-1 [1.32] | (S)-1 [2700] | (S)-2 [10] |
| Comp. Ex. 1 | (A)-1 [100] | (B)-2 [8.00] | (D)-1 [1.20] | (E)-1 [1.32] | (S)-1 [2700] | (S)-2 [10] |

In Table 1, the reference characters indicate the following. Further, the values in brackets [ ] indicate the amount (in terms of parts by weight) of the component added.

(A)-1: a copolymer represented by chemical formula (a1-11-1) shown below with Mw=10,000 and Mw/Mn=1.5. In the formula, the subscript numerals shown to the bottom right of the parentheses ( ) indicate the percentage (mol %) of the respective structural units within the copolymer.

Thereafter, a post exposure bake (PEB) treatment was conducted at 110° C. for 60 seconds, followed by alkali development for 30 seconds at 23° C. in a 2.38% by weight aqueous solution of tetramethylammonium hydroxide (TMAH) (product name: NMD-3; manufactured by Tokyo Ohka Kogyo Co., Ltd.). Then, the resist was washed for 30 seconds with pure water, followed by drying by shaking.

As a result, in each of the examples, a line and space pattern (hereafter, referred to as "L/S pattern") having a line width of 120 nm and a pitch of 240 nm was formed on the resist film.

[Sensitivity—(1)]

The optimum exposure dose Eop (mJ/cm$^2$; sensitivity) with which the L/S pattern having a line width of 120 nm and a pitch of 240 nm was determined. The results are shown in Table 2.

[Evaluation of Exposure Margin (EL Margin)]

The exposure dose with which an L/S pattern having a dimension of the target dimension (line width: 120 nm)±5% (i.e., 114 nm to 126 nm) was determined, and the EL margin (unit: %) was determined by the following formula. The results are shown in Table 2.

EL margin (%)=(|E1−E2|/Eop)×100

E1: Exposure dose (mJ/cm$^2$) with which an L/S pattern having a line width of 114 nm was formed
E2: Exposure dose (mJ/cm$^2$) with which an L/S pattern having a line width of 126 nm was formed

TABLE 2

|  | Ex. 9 | Comp. Ex. 1 |
| --- | --- | --- |
| PAB/PEB (° C.) | 110/110 | 110/110 |
| Eop (mJ/cm$^2$) | 46.2 | 31.8 |
| EL margin (%) | 6.72 | 6.21 |

As seen from the results shown in Table 2, it was confirmed that the resist composition of Example 9 which contained an acid generator consisting of the compound (B1-6) according to the present invention exhibited an excellent EL margin, as compared to the resist composition of Comparative Example 1.

[Evaluation of Resist Pattern Shape—(1)]

Each of the L/S patterns obtained in the "formation of resist pattern" was observed from the upper side thereof using an electron scanning microscope (SEM) to evaluate the shape of the resist pattern.

As a result, it was confirmed that the L/S pattern of Example 9 had an excellent shape with reduced surface roughness and line edge roughness, as compared to the L/S pattern of Comparative Example 1.

<Synthesis of Compound (B1')>

Examples 10 to 13

Novel compounds (B1-1') to (B1-4') were synthesized in accordance with the following synthesis examples.

[Example 10

Synthesis of Compound (B1-1')]

2 g of the compound (2) was added to 20 g of dichloromethane and 20 g of water, followed by stirring. Then, 2.16 g of a compound (3') was added thereto, followed by stirring for 1 hour. The reaction mixture was subjected to liquid separation, and the resultant was washed four times with 20 g of water. After the washing, the organic solvent phase was concentrated and solidified, thereby obtaining 2.1 g of a compound (B1-1').

The obtained compound (B1-1') was analyzed by NMR.
$^1$H-NMR (DMSO-d6, 400 MHz): δ(ppm)=7.69-7.81 (m, 10H, Ar), 7.46 (s, 2H, Ar), 6.49-6.55 (m, 1H Vinyl), 4.02-4.27 (m, 6H, CH$_2$+Vinyl), 2.36 (s, 6H, CH$_3$), 1.55-1.87 (m, 17H, adamantane+CH$_2$)
$^{19}$F-NMR (DMSO-d6, 376 MHz): δ(ppm)=−77.7

From the results shown above, it was confirmed that the compound (B1-1') had a structure shown below.

[Chemical Formula 100]

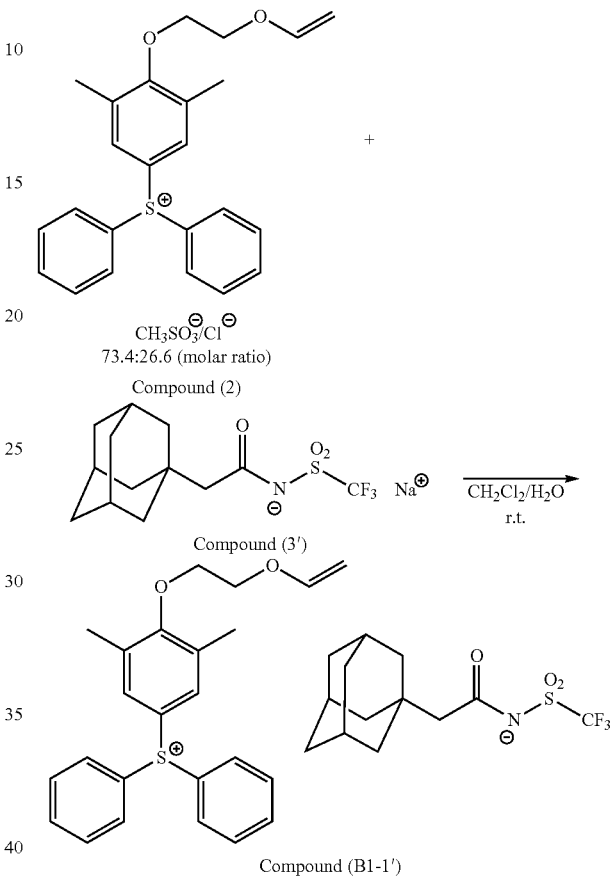

Compound (B1-1')

[Example 11

Synthesis of Compound (B1-2')]

(i) Synthesis Example of Compound (4')

2.35 g of trifluoromethanesulfoneamide and 11.75 g of acetone were added to and dissolved in a three-necked flask equipped with a stirrer and a thermometer, and 3.34 g of sodium carbonate was added thereto, followed by stirring at room temperature for 10 minutes. The reaction mixture was cooled with ice, and 3.20 g of cyclohexylsulfonyl chloride was gradually added thereto. Then, the resultant was stirred at room temperature for 60 hours, and the reaction mixture was filtered, followed by drying the filtrate. Finally, washing was conducted using tert-butylmethylether (TBME), thereby obtaining 1.94 g of a compound (4') shown below.

The obtained compound (4') was analyzed by NMR.
$^1$H-NMR (DMSO-d6, 400 MHz): δ(ppm)=1.04-1.41 (m, 5H, a), 1.58 (d, 1H, a), 1.73 (d, 2H, b), 2.07 (d, 2H, b), 2.98 (tt, 1H, c)
$^{19}$F-NMR (DMSO-d6, 376 MHz): δ(ppm)=−78.2

From the results shown above, it was confirmed that the compound (4') had a structure shown below.

[Chemical Formula 101]

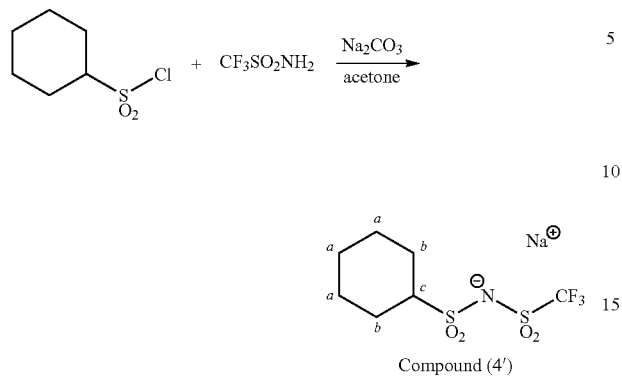

Compound (4')

(ii) Synthesis Example of Compound (B1-2')

2 g of the compound (2) was added to 20 g of dichloromethane and 20 g of water, followed by stirring. Then, 1.64 g of a compound (4') was added thereto, followed by stirring for 1 hour. The reaction mixture was subjected to liquid separation, and the resultant was washed four times with 20 g of water. After the washing, the organic solvent phase was concentrated and solidified, thereby obtaining 2.2 g of a compound (B1-2').

The obtained compound (B1-2') was analyzed by NMR.

$^1$H-NMR (DMSO-d6, 400 MHz): δ(ppm)=7.69-7.81 (m, 10H, Ar), 7.46 (s, 2H, Ar), 6.49-6.55 (m, 1H Vinyl), 4.02-4.27 (m, 6H, CH$_2$+Vinyl), 2.77-2.81 (m, 1H, Cyclohexyl), 2.36 (s, 6H, CH$_3$), 2.04-2.08 (m, 2H, Cyclohexyl), 1.73-1.75 (m, 2H, Cyclohexyl), 1.56-1.59 (m, 1H, Cyclohexyl), 1.07-1.33 (m, 5H, Cyclohexyl)

$^{19}$F-NMR (DMSO-d6, 376 MHz): δ(ppm)=−74.7

From the results shown above, it was confirmed that the compound (B1-2') had a structure shown below.

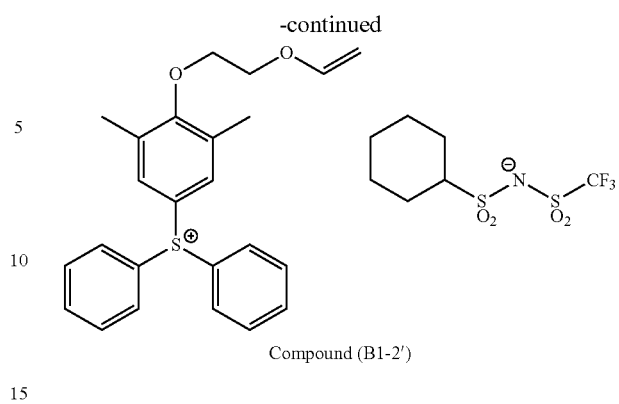

Compound (B1-2')

[Example 12

Synthesis of Compound (B1-3')]

2 g of the compound (2) was added to 20 g of dichloromethane and 20 g of water, followed by stirring. Then, 2.07 g of a compound (5') was added thereto, followed by stirring for 1 hour. The reaction mixture was subjected to liquid separation, and the resultant was washed four times with 20 g of water. After the washing, the organic solvent phase was concentrated and solidified, thereby obtaining 2.1 g of a compound (B1-3').

The obtained compound (B1-3') was analyzed by NMR.

$^1$H-NMR (DMSO-d6, 400 MHz): δ(ppm)=7.69-7.81 (m, 10H, Ar), 7.46 (s, 2H, Ar), 6.49-6.55 (m, 1H Vinyl), 4.02-4.27 (m, 6H, CH$_2$+Vinyl), 2.36 (s, 6H, CH$_3$), 1.55-1.88 (m, 15H, Adamantane)

$^{19}$F-NMR (DMSO-d6, 376 MHz): δ(ppm)=−74.5

From the results shown above, it was confirmed that the compound (B1-3') had a structure shown below.

[Chemical Formula 102]

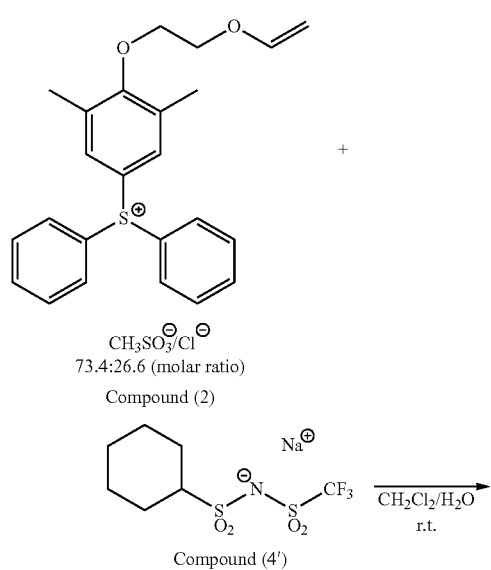

[Chemical Formula 103]

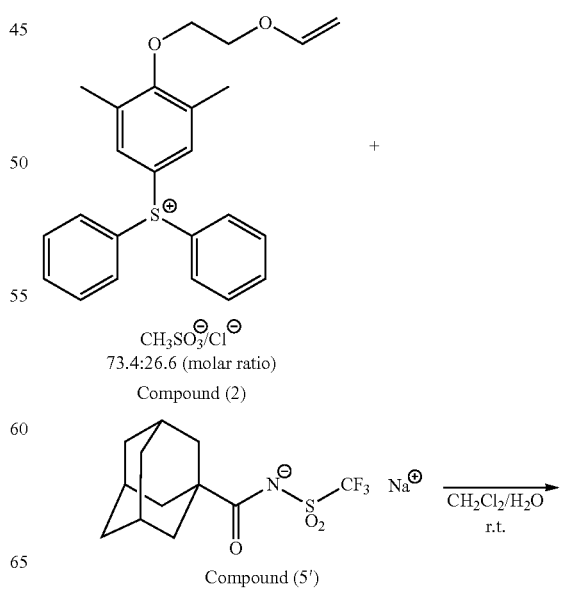

-continued

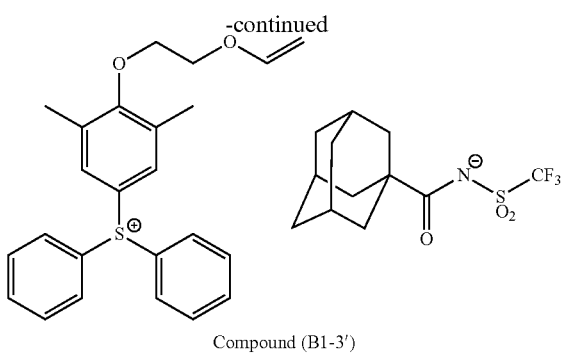

Compound (B1-3')

[Example 13

Synthesis of Compound (B1-4')]

(i) Synthesis Example of Compound (6')

1.71 g of trifluoromethanesulfoneamide and 17.1 g of THF were stirred while cooling with ice, and 0.45 g of sodium hydride was added thereto. Then, a mixture containing 3.62 g of a compound (I') and 7.24 g of THF was added thereto while maintaining the temperature of the mixture at 10° C. or lower, and a reaction was performed under reflux for 20 hours. Thereafter, 22 ml of water and 44 g of t-butylmethylether (TBME) were added to the resultant in this order and stirred, followed by collecting the TBME phase. The collected phase was dried and purified, thereby obtaining 1.2 g of a compound (6') in the form of a transparent liquid (purity: %, yield: 24%).

The obtained compound (6') was analyzed by NMR.

$^1$H-NMR (acetone, 400 MHz): δ(ppm)=1.60 (m, 6H, adamantane), 2.08 (m, 6H, adamantane), 2.17 (m, 3H, adamantane)

$^{19}$F-NMR (acetone, 376 MHz): δ(ppm)=−68.4 (s, 2F, c), −75.3 (s, 3F, a), −112.0 (s, 2F, b)

From the results shown above, it was confirmed that the compound (6') had a structure shown below.

[Chemical Formula 104]

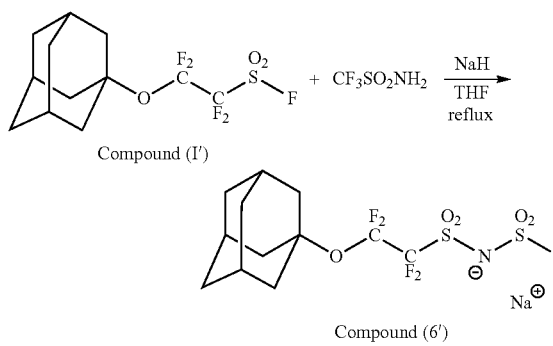

(ii) Synthesis Example of Compound (B1-4')

2 g of the compound (2) was added to 20 g of dichloromethane and 20 g of water, followed by stirring. Then, 2.57 g of a compound (6') was added thereto, followed by stirring for 1 hour. The reaction mixture was subjected to liquid separation, and the resultant was washed four times with 20 g of water. After the washing, the organic solvent phase was concentrated and solidified, thereby obtaining 2.7 g of a compound (B1-4').

The obtained compound (B1-4') was analyzed by NMR.

$^1$H-NMR (DMSO-d6, 400 MHz): δ(ppm)=7.69-7.81 (m, 10H, Ar), 7.46 (s, 2H, Ar), 6.49-6.55 (m, 1H Vinyl), 4.02-4.27 (m, 6H, CH$_2$+Vinyl), 2.36 (s, 6H, CH$_3$), 2.13 (m, 3H, adamantane), 1.99 (m, 6H, adamantane), 1.59 (s, 6H, adamantane)

$^{19}$F-NMR (DMSO-d6, 376 MHz): δ(ppm)=−69.2, −76.0, −112.9

From the results shown above, it was confirmed that the compound (B1-4') had a structure shown below.

[Chemical Formula 105]

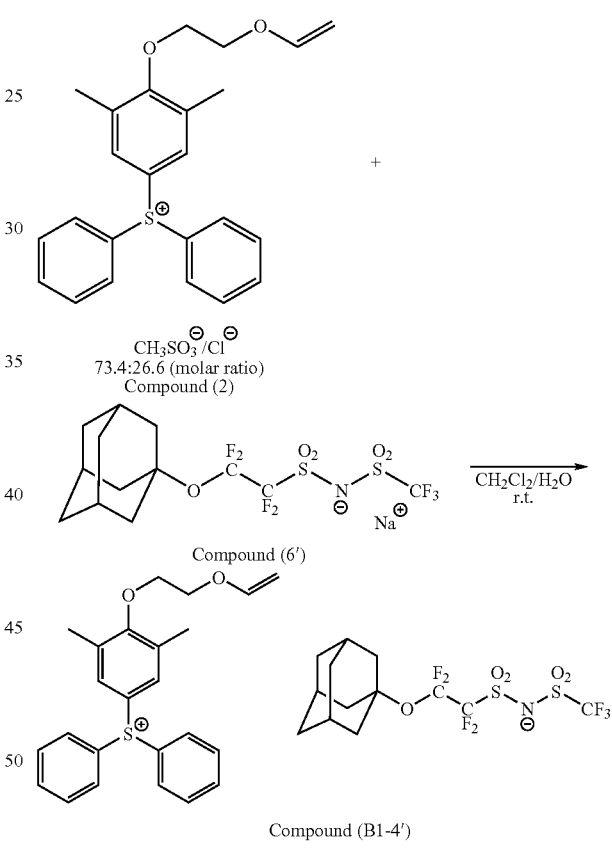

<Production of Resist Composition>

Example 14, Comparative Example 2

The components shown in Table 3 were mixed together and dissolved to obtain positive resist compositions.

TABLE 3

| | Component (A) | Component (B) | Component (D) | Component (E) | Component (S) | | Eop (mJ/cm$^2$) |
|---|---|---|---|---|---|---|---|
| Ex. 14 | (A)-1 [100] | (B)-1' [11.7] | (D)-1 [1.20] | (E)-1 [1.32] | (S)-1 [2700] | (S)-2 [10] | 47.0 |

TABLE 3-continued

|  | Component (A) | Component (B) | Component (D) | Component (E) | Component (S) | | Eop (mJ/cm$^2$) |
|---|---|---|---|---|---|---|---|
| Comp. Ex. 2 | (A)-1 [100] | (B)-2 [8.00] | (D)-1 [1.20] | (E)-1 [1.32] | (S)-1 [2700] | (S)-2 [10] | 31.8 |

In Table 3, the reference characters indicate the following. Further, the values in brackets [ ] indicate the amount (in terms of parts by weight) of the component added.

(A)-1: a copolymer represented by chemical formula (a1-0-1) shown below with Mw=10,000 and Mw/Mn=1.5.

(B)-1': the aforementioned compound (B1-4')

(B)-2: (4-methylphenyl)diphenylsulfonium nonafluoro-n-butanesulfonate (D)-1: tri-n-pentylamine (E)-1: salicylic acid (S)-1: a mixed solvent of PGMEA/PGME=6/4 (weight ratio)

(S)-2: γ-butyrolactone

<Evaluation of Lithographic Properties—(2)>

Using the obtained resist compositions, resist patterns were formed in the following manner, and the lithography properties were evaluated.

[Formation of Resist Pattern (2)]

Resist patterns were formed in the same manner as in the aforementioned [Formation of resist pattern—(1)].

As a result, in each of the examples, an L/S pattern having a line width of 120 nm and a pitch of 240 nm was formed on the resist film.

[Sensitivity—(2)]

The optimum exposure dose Eop (mJ/cm$^2$; sensitivity) with which the L/S pattern having a line width of 120 nm and a pitch of 240 nm was determined. The results are shown in Table 3.

[Evaluation of Resist Pattern Shape—(2)]

Each of the L/S patterns obtained in the "formation of resist pattern" was observed from the upper side thereof using an electron scanning microscope (SEM) to evaluate the shape of the resist pattern.

As a result, it was confirmed that the L/S pattern of Example 14 had an excellent shape with reduced surface roughness and line edge roughness, as compared to the L/S pattern of Comparative Example 2.

<Synthesis of Compound (B1")>

Examples 15 and 16

Novel compounds (B1-1") and (B1-2") were synthesized in accordance with the following synthesis examples.

[Example 15

Synthesis of Compound (B1-1")]

(i) Synthesis Example of Compound (3")

16.7 ml of tetrahydrofuran was added to 5.0 g of 2-naphthylmethyloxytetrafluoroethanesulfonyl fluoride, and an aqueous solution obtained by dissolving 0.98 g of lithium hydroxide in 13.6 ml of pure water was dropwise added to the resulting solution in an ice bath. Then, the solution was stirred in the ice bath. Since no absorption ascribed to —SO$_2$F was observed at −217.6 ppm by $^{19}$F-NMR, it was confirmed that all fluorinated sulfonyl groups were converted to lithium sulfonate.

Thereafter, the reaction mixture was concentrated and dried to obtain a viscous white solid (crude product). The obtained crude product was dissolved in 14.2 ml of acetone, and filtered to remove the by-produced LiF. The filtrate was concentrated, thereby obtaining 5.50 g of a precursor compound (3").

[Chemical Formula 106]

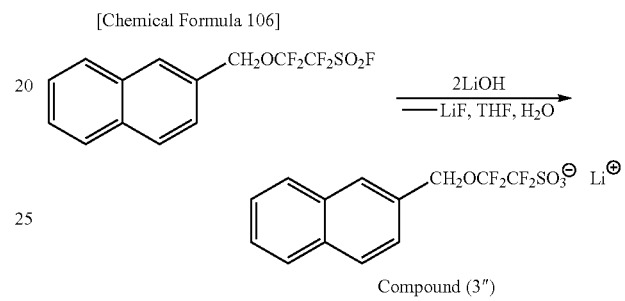

Compound (3")

(ii) Synthesis Example of Compound (B1-1")

2 g of the compound (2) was added to 20 g of dichloromethane and 20 g of water, followed by stirring. Then, 1.87 g of a compound (3") was added thereto, followed by stirring for 1 hour. The reaction mixture was subjected to liquid separation, and the resultant was washed four times with 20 g of water. After the washing, the organic solvent phase was concentrated and solidified, thereby obtaining 2.4 g of a compound (B1-1").

The obtained compound (B1-1") was analyzed by NMR.

$^1$H-NMR (DMSO-d6, 400 MHz): δ(ppm)=7.51-7.96 (m, 17H, Ar), 7.46 (s, 2H, Ar), 6.49-6.55 (m, 1H Vinyl), 5.20 (s, 2H, CH$_2$), 4.02-4.27 (m, 6H, CH$_2$+Vinyl), 2.36 (s, 6H, CH$_3$)

$^{19}$F-NMR (DMSO-d6, 376 MHz): δ(ppm)=−80.5, −113.7

From the results shown above, it was confirmed that the compound (B1-1") had a structure shown below.

[Chemical Formula 107]

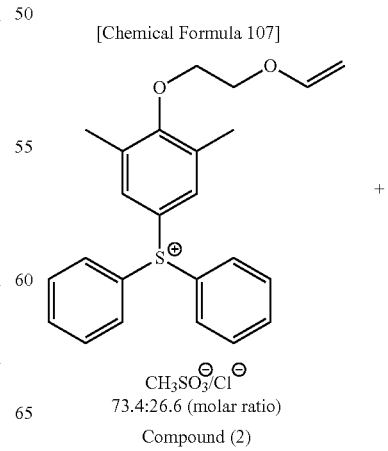

CH$_3$SO$_3^\ominus$/Cl$^\ominus$
73.4:26.6 (molar ratio)
Compound (2)

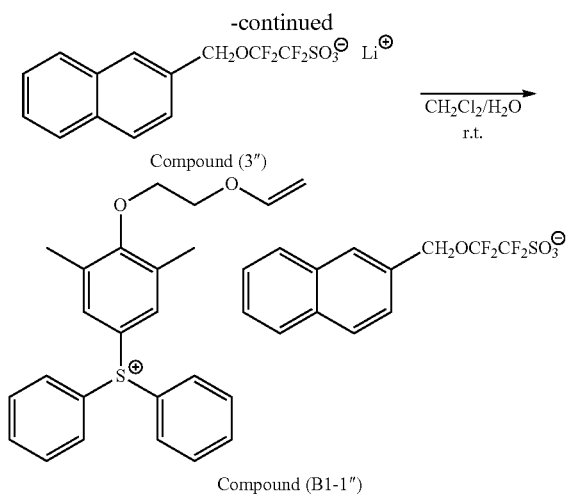

Compound (3″)

Compound (B1-1″)

[Example 16]

Synthesis of Compound (B1-2″)]

(i) Synthesis Example of Compound (4″)

142.35 g of diglyme was added to 28.57 g of silver fluoride and cooled to 0° C. Then, 40.55 g of tetrafluoro-1,2-oxathiethane-2,2-dioxide was dropwise added thereto. The resultant was stirred at room temperature for 1 hour, and the reaction system was cooled to 0° C. again. A diglyme (99.88 g) solution of 1-bromoadamantane (49.94 g) was dropwise added thereto, and stirred at room temperature for 14 hours. 508 ml of hexane was further added, and the reaction system was cooled to 0° C. 127 ml of water was dropwise added thereto at 0° C., and stirred for 10 minutes. Insoluble matter was removed by filtration, and the filtrate was subjected to liquid separation. The obtained organic phase was washed with 169 ml of a saturated saline solution, and dried with magnesium sulfate, followed by concentration under reduced pressure. 254 ml of hexane was added to the residue, and the precipitated crystal was separated by filtration. Then, the filtrate was concentrated under reduced pressure, thereby obtaining 23.30 g of 1-adamantoxytetrafluoroethanesulfonyl fluoride (compound A) (yield: 30%).

The compound A was analyzed by NMR.

$^1$H-NMR (DMSO-d6, 400 MHz): δ(ppm)=2.19 (s, 3H, adamantane), 2.05 (s, 6H, adamantane), 1.62 (s, 6H, adamantane)

$^{19}$F-NMR (DMSO-d6, 376 MHz): δ(ppm)=−69.96, −108.05

From the results shown above, it was confirmed that the compound A had a structure shown below.

[Chemical Formula 108]

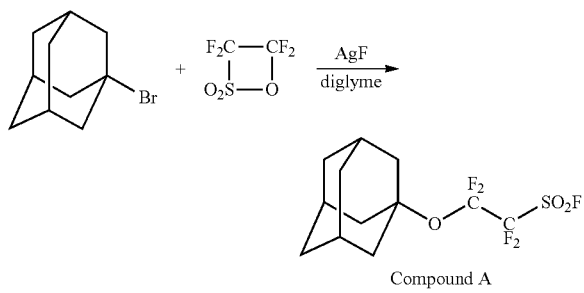

Compound A

Subsequently, 16.7 ml of tetrahydrofuran was added to 10 g of 1-adamantoxytetrafluoroethanesulfonyl fluoride (compound A), and an aqueous solution obtained by dissolving 0.64 g of lithium hydroxide in 13.6 ml of pure water was dropwise added to the resulting solution in an ice bath. Then, the solution was stirred in the ice bath. Thereafter, the reaction mixture was filtered to remove LiF, and the filtrate was washed with 33.4 ml of t-butylmethylether. Then, the aqueous solution was collected by liquid separation, thereby obtaining a 32% by weight aqueous solution of a compound (4″) (yield: 70%).

The obtained compound (4″) was analyzed by NMR.

$^1$H-NMR (DMSO-d6, 400 MHz): δ(ppm)=2.33 (s, 3H, adamantane), 2.21 (s, 6H, adamantane), 1.80 (s, 6H, adamantane)

$^{19}$F-NMR (DMSO-d6, 376 MHz): δ(ppm)=−70.37, −113.70

From the results shown above, it was confirmed that the compound (4″) had a structure shown below.

[Chemical Formula 109]

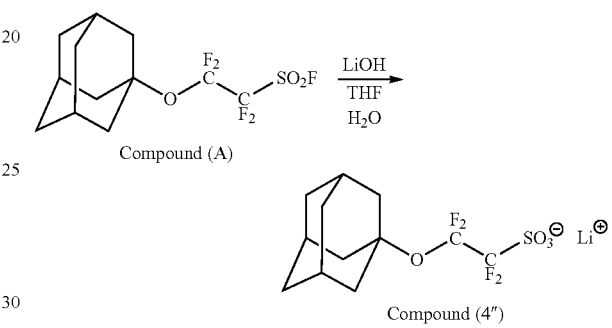

Compound (4″)

(ii) Synthesis Example of Compound (B1-2″)

2 g of the compound (2) was added to 20 g of dichloromethane and 20 g of water, followed by stirring. Then, 1.84 g of a compound (4″) was added thereto, followed by stirring for 1 hour. The reaction mixture was subjected to liquid separation, and the resultant was washed four times with 20 g of water. After the washing, the organic solvent phase was concentrated and solidified, thereby obtaining 2.3 g of a compound (B1-2″).

The obtained compound (B1-2″) was analyzed by NMR.

$^1$H-NMR (DMSO-d6, 400 MHz): δ(ppm)=7.69-7.81 (m, 10H, Ar), 7.46 (s, 2H, Ar), 6.49-6.55 (m, 1H Vinyl), 4.02-4.27 (m, 6H, CH$_2$+Vinyl), 2.36 (s, 6H, CH$_3$), 2.09 (s, 3H, adamantane), 1.96 (s, 6H, adamantane), 1.56 (s, 6H, adamantane)

$^{19}$F-NMR (DMSO-d6, 376 MHz): δ(ppm)=−70.13, −113.36

From the results shown above, it was confirmed that the compound (B1-2″) had a structure shown below.

[Chemical Formula 110]

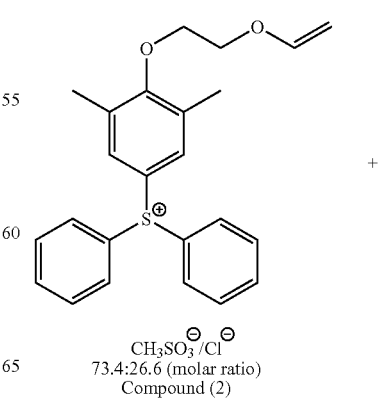

+

CH$_3$SO$_3^\ominus$/Cl$^\ominus$
73.4:26.6 (molar ratio)
Compound (2)

-continued

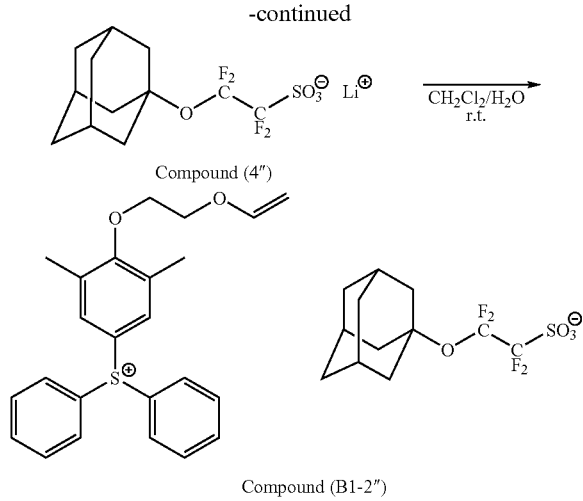

Compound (4″)

Compound (B1-2″)

<Production of Resist Composition>

Example 17 and 18, Comparative Example 3

The components shown in Table 4 were mixed together and dissolved to obtain positive resist compositions.

TABLE 4

|         | Component (A) | Component (B) | Component (D) | Component (E) | Component (S) | | Eop (mJ/cm²) |
|---------|---------------|---------------|---------------|---------------|---------------|---|--------------|
| Ex. 17  | (A)-1 [100]   | (B)-1″ [9.92] | (D)-1 [1.20]  | (E)-1 [1.32]  | (S)-1 [2700]  | (S)-2 [10] | 46.0 |
| Ex. 18  | (A)-1 [100]   | (B)-2″ [9.84] | (D)-1 [1.20]  | (E)-1 [1.32]  | (S)-1 [2700]  | (S)-2 [10] | 46.0 |
| Comp. Ex. 3 | (A)-1 [100] | (B)-2 [8.00] | (D)-1 [1.20]  | (E)-1 [1.32]  | (S)-1 [2700]  | (S)-2 [10] | 31.8 |

In Table 4, the reference characters indicate the following. Further, the values in brackets [ ] indicate the amount (in terms of parts by weight) of the component added.

(A)-1: a copolymer represented by chemical formula (A1-11-1) with Mw=10,000 and Mw/Mn=1.5.

(B)-1″: the aforementioned compound (B1-1″)
(B)-2″: the aforementioned compound (B1-2″)
(B)-2: (4-methylphenyl)diphenylsulfonium nonafluoro-n-butanesulfonate
(D)-1: tri-n-pentylamine
(E)-1: salicylic acid
(S)-1: a mixed solvent of PGMEA/PGME=6/4 (weight ratio)
(S)-2: γ-butyrolactone <Evaluation of Lithographic Properties—(3)>

Using the obtained resist compositions, resist patterns were formed in the following manner, and the lithography properties were evaluated.

[Formation of Resist Pattern (3)]

Resist patterns were formed in the same manner as in the aforementioned [Formation of resist pattern—(1)].

As a result, in each of the examples, an L/S pattern having a line width of 120 nm and a pitch of 240 nm was formed on the resist film.

[Sensitivity—(3)]

The optimum exposure dose Eop (mJ/cm²; sensitivity) with which the L/S pattern having a line width of 120 nm and a pitch of 240 nm was determined. The results are shown in Table 4.

[Evaluation of resist pattern shape—(3)]

Each of the L/S patterns obtained in the "formation of resist pattern" was observed from the upper side thereof using an electron scanning microscope (SEM) to evaluate the shape of the resist pattern.

As a result, it was confirmed that the L/S patterns of Examples 17 and 18 had an excellent shape with reduced surface roughness and line edge roughness, as compared to the L/S pattern of Comparative Example 3.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A resist composition comprising a base component (A) which exhibits changed solubility in an alkali developing solution under action of acid and an acid-generator component (B) which generates acid upon exposure, said component (B) comprising an acid generator (B1) comprised of a compound represented by general formula (b1-1) shown below;

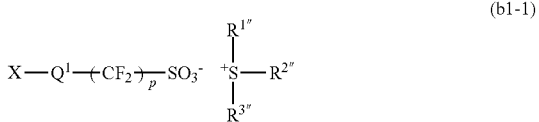

(b1-1)

wherein each of $R^{1''}$ to $R^{3''}$ independently represents an aryl group which may have a substituent or an alkyl group which may have a substituent, with the provision that at least one of $R^{1''}$ to $R^{3''}$ represents a substituted aryl group having part of the hydrogen atoms substituted with a group represented by general formula (b1-1-0) shown below, and two of $R^{1''}$ to $R^{3''}$ may be bonded to each other to form a ring with the sulfur atom; X represents a hydrocarbon group of 3 to 30 carbon atoms which may have a substituent; $Q^1$ represents a divalent linking group containing a carbonyl group; and p represents an integer of 1 to 3:

(b1-1-0)

wherein W represents a linear or branched alkylene group of 2 to 10 carbon atoms.

2. The resist composition according to claim 1, wherein said base component (A) is a base component which exhibits increased solubility in an alkali developing solution under action of acid.

3. The resist composition according to claim 2, wherein said base component (A) comprises a resin component (A1) comprising a structural unit (a1) derived from an acrylate ester containing an acid dissociable, dissolution inhibiting group.

4. The resist composition according to claim 3, wherein said resin component (A1) further comprises a structural unit (a2) derived from an acrylate ester containing a lactone-containing cyclic group.

5. The resist composition according to claim 3, wherein said resin component (A1) further comprises a structural unit (a3) derived from an acrylate ester containing a polar group-containing aliphatic hydrocarbon group.

6. The resist composition according to claim 1, which further comprises a nitrogen-containing organic compound (D).

7. A method of forming a resist pattern, comprising: forming a resist film using a resist composition of claim 1; conducting exposure of said resist film; and alkali-developing said resist film to form a resist pattern.

8. A compound comprising a compound (B1) represented by general formula (b1-1) shown below

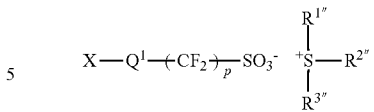
(b1-1)

wherein each of $R^{1''}$ to $R^{3''}$ independently represents an aryl group which may have a substituent or an alkyl group which may have a substituent, with the provision that at least one of $R^{1''}$ to $R^{3''}$ represents a substituted aryl group having part of the hydrogen atoms substituted with a group represented by general formula (b1-1-0) shown below, and two of $R^{1''}$ to $R^{3''}$ may be bonded to each other to form a ring with the sulfur atom; X represents a hydrocarbon group of 3 to 30 carbon atoms which may have a substituent; $Q^1$ represents a divalent linking group containing a carbonyl group; and p represents an integer of 1 to 3:

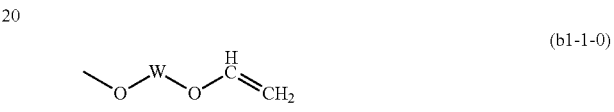
(b1-1-0)

wherein W represents a linear or branched alkylene group of 2 to 10 carbon atoms.

9. An acid generator comprising the compound of claim 8.

* * * * *